United States Patent
Han et al.

(10) Patent No.: US 11,737,357 B2
(45) Date of Patent: Aug. 22, 2023

(54) COMPOUND AND ORGANIC LIGHT-EMITTING DEVICE COMPRISING SAME

(71) Applicant: LG Chem, Ltd., Seoul (KR)

(72) Inventors: Miyeon Han, Daejeon (KR); Dong Hoon Lee, Daejeon (KR); Jungoh Huh, Daejeon (KR); Boonjae Jang, Daejeon (KR); Minyoung Kang, Daejeon (KR); Dong Uk Heo, Daejeon (KR); Min Woo Jung, Daejeon (KR)

(73) Assignee: LG Chem, Ltd.

( * ) Notice: Subject to any disclaimer, the term of this patent is extended or adjusted under 35 U.S.C. 154(b) by 345 days.

(21) Appl. No.: 15/770,633

(22) PCT Filed: Oct. 27, 2016

(86) PCT No.: PCT/KR2016/012157
§ 371 (c)(1),
(2) Date: Apr. 24, 2018

(87) PCT Pub. No.: WO2017/074053
PCT Pub. Date: May 4, 2017

(65) Prior Publication Data
US 2019/0055222 A1   Feb. 21, 2019

(30) Foreign Application Priority Data

Oct. 27, 2015   (KR) ................. 10-2015-0149714

(51) Int. Cl.
*H10K 85/60* (2023.01)
*C07D 235/06* (2006.01)
(Continued)

(52) U.S. Cl.
CPC ......... *H10K 85/654* (2023.02); *C07D 235/06* (2013.01); *C07D 251/12* (2013.01); *C07D 251/24* (2013.01); *C07D 263/52* (2013.01); *C07D 277/60* (2013.01); *C07D 403/10* (2013.01); *C07D 405/10* (2013.01); *C07D 409/10* (2013.01); *C07D 413/10* (2013.01);
(Continued)

(58) Field of Classification Search
CPC .................... H01L 51/0069; H10K 85/654
See application file for complete search history.

(56) References Cited

U.S. PATENT DOCUMENTS

2004/0251816 A1   12/2004   Leo et al.
2013/0240796 A1   9/2013   Parham et al.
(Continued)

FOREIGN PATENT DOCUMENTS

EP   2629346 A2   8/2013
EP   2991128 A1   3/2016
(Continued)

OTHER PUBLICATIONS

STN Registry, "CAS Registry No. 1813573-58-8", STN CAS database, 1 page, Oct. 23, 2015. (Year: 2015).*
(Continued)

*Primary Examiner* — Daniel P Malley, Jr.
(74) *Attorney, Agent, or Firm* — Lerner David LLP

(57) ABSTRACT

The present application relates to a compound of Chemical Formula 1 and an organic light emitting device including the same.

10 Claims, 1 Drawing Sheet

(51) Int. Cl.

| | | |
|---|---|---|
| *C07D 251/12* | (2006.01) | |
| *C07D 263/52* | (2006.01) | |
| *C07D 277/60* | (2006.01) | |
| *C09K 11/06* | (2006.01) | |
| *H10K 50/12* | (2023.01) | |
| *H10K 50/15* | (2023.01) | |
| *H10K 50/16* | (2023.01) | |
| *H10K 50/18* | (2023.01) | |
| *H10K 50/81* | (2023.01) | |
| *H10K 50/82* | (2023.01) | |
| *H10K 50/17* | (2023.01) | |
| *H10K 71/16* | (2023.01) | |
| *C07D 403/10* | (2006.01) | |
| *C07D 251/24* | (2006.01) | |
| *C07D 405/10* | (2006.01) | |
| *C07D 409/10* | (2006.01) | |
| *C07D 413/10* | (2006.01) | |
| *C07D 471/04* | (2006.01) | |

(52) U.S. Cl.
 CPC ............ *C07D 471/04* (2013.01); *C09K 11/06* (2013.01); *H10K 50/12* (2023.02); *H10K 50/15* (2023.02); *H10K 50/16* (2023.02); *H10K 50/171* (2023.02); *H10K 50/18* (2023.02); *H10K 50/81* (2023.02); *H10K 50/82* (2023.02); *H10K 71/164* (2023.02); *H10K 85/615* (2023.02); *H10K 85/626* (2023.02); *H10K 85/6572* (2023.02); *H10K 85/6574* (2023.02); *H10K 85/6576* (2023.02)

(56) References Cited

U.S. PATENT DOCUMENTS

| | | | |
|---|---|---|---|
| 2014/0001456 A1 | 1/2014 | Mizutani et al. | |
| 2014/0299192 A1* | 10/2014 | Lee | C07D 409/14 136/263 |
| 2015/0102321 A1 | 4/2015 | Kwong et al. | |
| 2015/0228908 A1 | 8/2015 | Lee et al. | |
| 2015/0314287 A1 | 11/2015 | Igata | |
| 2015/0337197 A1 | 11/2015 | Jatsch et al. | |
| 2015/0349270 A1 | 12/2015 | Lee et al. | |
| 2016/0020404 A1 | 1/2016 | Ito et al. | |
| 2016/0072078 A1 | 3/2016 | Lee et al. | |
| 2016/0126471 A1* | 5/2016 | Lui | H01L 51/0067 257/40 |
| 2016/0172598 A1 | 6/2016 | Lee et al. | |
| 2016/0181548 A1* | 6/2016 | Parham | H01L 51/0085 548/440 |
| 2016/0248020 A1* | 8/2016 | Ondari | C07D 401/04 |
| 2016/0308147 A1* | 10/2016 | Parham | C07F 9/65517 |
| 2016/0322583 A1 | 11/2016 | Kim et al. | |
| 2016/0351822 A1 | 12/2016 | Lee et al. | |
| 2017/0018718 A1 | 1/2017 | Jang et al. | |
| 2017/0033294 A1 | 2/2017 | Jang et al. | |
| 2017/0062736 A1 | 3/2017 | Parham et al. | |
| 2017/0222158 A1 | 8/2017 | Jung et al. | |
| 2017/0331067 A1* | 11/2017 | Park | C09K 11/06 |
| 2018/0123049 A1* | 5/2018 | Lee | H10K 85/6572 |
| 2018/0127385 A1 | 5/2018 | Jung et al. | |
| 2018/0315930 A1 | 11/2018 | Han et al. | |
| 2020/0295272 A1* | 9/2020 | Lee | H01L 51/0067 |

FOREIGN PATENT DOCUMENTS

| | | | | |
|---|---|---|---|---|
| EP | 3016169 | A1 | 5/2016 | |
| EP | 3137458 | A1 | 3/2017 | |
| EP | 3296293 | A2 | 3/2018 | |
| JP | 2014503502 | A | 2/2014 | |
| JP | 201583566 | A | 4/2015 | |
| JP | 2015509954 | A | 4/2015 | |
| JP | 2015210242 | A | 11/2015 | |
| JP | 2016051901 | A | 4/2016 | |
| JP | 2016092412 | A | 5/2016 | |
| JP | 2017518277 | A | 7/2017 | |
| JP | 2018521957 | A | 8/2018 | |
| JP | 2019501513 | A | 1/2019 | |
| KR | 20120117693 | A * | 10/2012 | |
| KR | 20140101661 | A | 8/2014 | |
| KR | 20140145456 | A | 12/2014 | |
| KR | 20150074603 | A | 7/2015 | |
| KR | 101542714 | B1 | 8/2015 | |
| KR | 20150090836 | A | 8/2015 | |
| KR | 20150104261 | A | 9/2015 | |
| KR | 101560102 | B1 | 10/2015 | |
| KR | 20150115622 | A | 10/2015 | |
| KR | 20150117173 | A | 10/2015 | |
| WO | 2003012890 | A2 | 2/2003 | |
| WO | WO-2010114264 | A2 * | 10/2010 | ......... H01L 51/0067 |
| WO | 2012069121 | A1 | 5/2012 | |
| WO | 2014094963 | A1 | 6/2014 | |
| WO | 2014200148 | A1 | 12/2014 | |
| WO | 2014209028 | A1 | 12/2014 | |
| WO | 2015014434 | A1 | 2/2015 | |
| WO | 2015073343 | A1 | 5/2015 | |
| WO | 2015115744 | A1 | 8/2015 | |
| WO | 2015152650 | A1 | 10/2015 | |
| WO | 2015152651 | A1 | 10/2015 | |

OTHER PUBLICATIONS

STN search conducted by the Examiner, All Pages, 2020. (Year: 2020).*
STN Registry, "1814939-30-4", Oct. 26, 2015, All Pages. (Year: 2015).*
STN Structure search for U.S. Appl. No. 15/770,633, filed 2021, All Pages. (Year: 2021).*
STN Registry "1814939-33-7", Oct. 26, 2015, All Pages. (Year: 2015).*
STN Structure search for U.S. Appl. No. 15/770,633 conducted by the Examiner May 14, 2021, All Pages. (Year: 2021).*
STN Registry Compound "1814939-43-9", Oct. 26, 2015, 1 Page. (Year: 2015).*
STN Registry Compound "1813573-62-4", Oct. 23, 2015, 1 Page. (Year: 2015).*
STN structure search conducted by the Examiner for U.S. Appl. No. 15/770,633, filed Aug. 9, 2021, All Pages. (Year: 2021).*
STN Registry Compound "1814939-42-8", Oct. 26, 2015, 1 Page (Year: 2015).*
STN structure search conducted by the Examiner for U.S. Appl. No. 15/770,633, filed Jan. 6, 2022, All Pages. (Year: 2022).*
STN Registry Compound "1814941-16-6", 2015, Oct. 26, 2015, 1 Page (Year: 2015).*
STN Registry Compound "1814939-63-3", 2015, Oct. 26, 2015, 1 Page (Year: 2015).*
STN Registry Compound "1814941-14-4", 2015, Oct. 26, 2015, 1 Page (Year: 2015).*
STN Structure search conducted by the Examiner for U.S. Appl. No. 15/770,633, filed Apr. 5, 2022, All Pages. (Year: 2022).*
STN Registry "1814941-13-3", Oct. 26, 2015, All Pages. (Year: 2015).*
STN Registry "1644606-38-1", Feb. 5, 2015, All Pages. (Year: 2015).*
STN structure search conducted by the Examiner on Sep. 13, 2022, All Pages. (Year: 2022).*
English machine translation of Tae (KR 20120117693 A) provided by the EPO website, 2022, all pages. (Year: 2022).*
STN Registry "1801999-71-2" Aug. 14, 2015, All Pages. (Year: 2015).*
STN Registry "1814941-08-6" Oct. 26, 2015, All Pages. (Year: 2015).*
STN Registry "1814941-15-5" Oct. 26, 2015, All Pages. (Year: 2015).*
STN structure search conducted by the Examiner on Mar. 24, 2023, All Pages. (Year: 2023).*

(56) References Cited

OTHER PUBLICATIONS

Search report from International Application No. PCT/KR2016/012157, dated Feb. 7, 2017.
Search report from International Application No. PCT/KR2016/012154, dated Jan. 31, 2017.
Extended European Search Report including Written Opinion for Application No. EP16860235.7 dated Sep. 26, 2018.
Extended European Search Report including Written Opinion for Application No. EP16860236.5 dated Sep. 26, 2018.

* cited by examiner

[Figure 1]
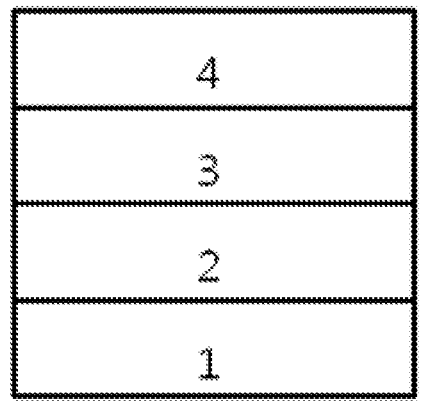
[Figure 2]
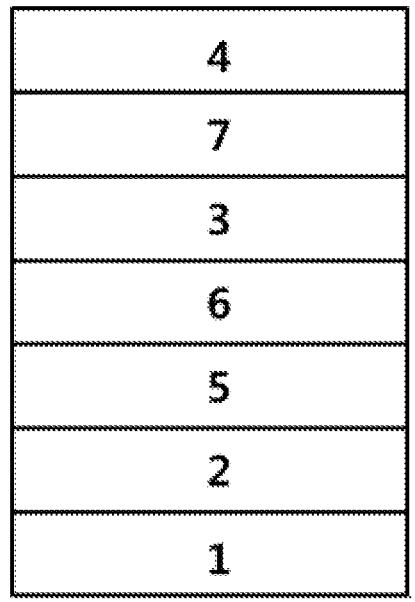

COMPOUND AND ORGANIC LIGHT-EMITTING DEVICE COMPRISING SAME

CROSS-REFERENCE TO RELATED APPLICATIONS

The present application is a national phase entry under 35 U.S.C. § 371 of International Application No. PCT/KR2016/012157 filed Oct. 27, 2016, which claims priority from Korean Patent Application No. 10-2015-0149714 filed in the Korean Intellectual Property Office on Oct. 27, 2015, the entire contents of which are incorporated herein by reference.

TECHNICAL FIELD

The present application relates to a compound and an organic light emitting device including the same.

BACKGROUND ART

In general, an organic light emitting phenomenon refers to a phenomenon in which electric energy is converted into light energy by using an organic material. An organic light emitting device using the organic light emitting phenomenon usually has a structure including a positive electrode, a negative electrode, and an organic material layer interposed therebetween. Here, the organic material layer may have a multi-layered structure composed of different materials in order to improve the efficiency and stability of an organic light emitting device in many cases, and for example, may be composed of a hole injection layer, a hole transport layer, a light emitting layer, an electron transport layer, an electron injection layer, and the like. In the structure of the organic light emitting device, if a voltage is applied between two electrodes, holes are injected from a positive electrode into the organic material layer and electrons are injected from a negative electrode into the organic material layer, and when the injected holes and electrons meet each other, an exciton is formed, and light is emitted when the exciton falls down again to a ground state.

There is a continuous need for developing a new material for the aforementioned organic light emitting device.

DETAILED DESCRIPTION OF THE INVENTION

Technical Problem

The present application provides a novel compound and an organic light emitting device including the same.

Technical Solution

The present application provides a compound represented by the following Chemical Formula 1.

[Chemical Formula 1]

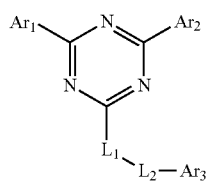

In Chemical Formula 1,
$Ar_1$ and $Ar_2$ are the same as or different from each other, and are each independently a substituted or unsubstituted aryl group; or a substituted or unsubstituted heterocyclic group, and
$L_1$ is represented by any one of the following Chemical Formulae 2 to 5,

[Chemical Formula 2]

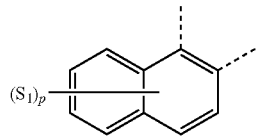

[Chemical Formula 3]

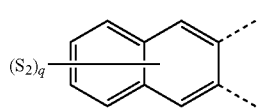

[Chemical Formula 4]

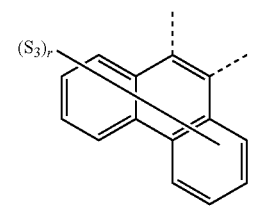

[Chemical Formula 5]

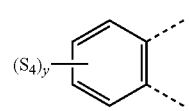

in Chemical Formulae 2 to 5,
a dotted line "------" is each a moiety bonded to a triazine group or $L_2$ of Chemical Formula 1,
$S_1$ to $S_4$ are the same as or different from each other, and are each independently hydrogen; deuterium; a halogen group; a substituted or unsubstituted alkyl group; a substituted or unsubstituted aryl group; or a substituted or unsubstituted heterocyclic group,
p and q are the same as or different from each other, and are each independently an integer of 0 to 6,
r is an integer of 0 to 8,
y is an integer of 0 to 4,
when p, q, r, and y are each an integer of 2 or more, a plurality of $S_1$ to $S_4$ are each the same as or different from each other,
$L_2$ is a direct bond; or a substituted or unsubstituted arylene group,
$Ar_3$ is represented by a substituted or unsubstituted aryl group; a substituted or unsubstituted heterocyclic group including S or O; a substituted or unsubstituted carbazole group; or any one of the following Chemical Formulae 6 to 10, when $L_1$ is Chemical Formulae 2 to 4,
$Ar_3$ is represented by a substituted or unsubstituted aryl group; a substituted or unsubstituted heterocyclic group including S or O; or any one of the following Chemical Formulae 6 to 10, when $L_1$ is Chemical Formula 5,

[Chemical Formula 6]

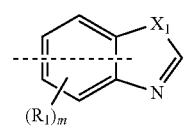

-continued

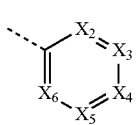
[Chemical Formula 7]

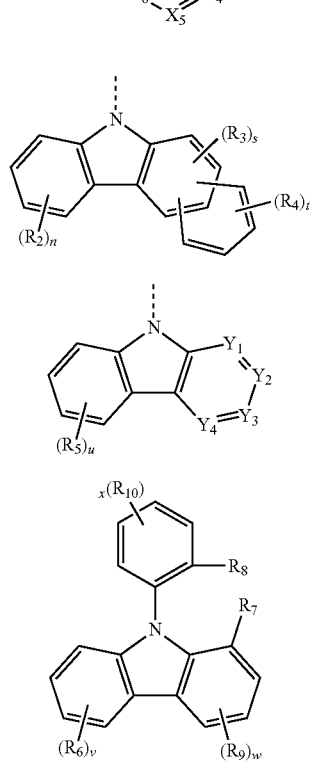
[Chemical Formula 8]

[Chemical Formula 9]

[Chemical Formula 10]

in Chemical Formulae 6 to 10, $X_1$ is O, S, or NR, at least two of $X_2$ to $X_6$ are N, and the others are each independently CR', R and R' are the same as or different from each other, and are each independently hydrogen; deuterium; a halogen group; a substituted or unsubstituted alkyl group; or a substituted or unsubstituted aryl group, $R_1$ to $R_6$, $R_9$, and $R_{10}$ are the same as or different from each other, and are each independently hydrogen; deuterium; a halogen group; a substituted or unsubstituted alkyl group; a substituted or unsubstituted aryl group; or a substituted or unsubstituted heterocyclic group, at least one of $Y_1$ to $Y_4$ is N, and the others are CR", R" is each independently hydrogen or deuterium, $R_7$ and $R_8$ are directly bonded or combine with each other to form a substituted or unsubstituted ring, m, n, t, u, v, and x are each an integer of 0 to 4, w is an integer of 0 to 3, and when m, n, t, u, v, w, and x are each an integer of 2 or more, a plurality of $R_1$ to $R_6$, $R_9$, and $R_{10}$ are each the same as or different from each other, s is an integer of 0 to 2, and when s is 2, two $R_3$s are the same as or different from each other, and " ------ " means a moiety bonded to $L_2$ of Chemical Formula 1, and the bonding moiety of Chemical Formula 10 is bonded to a ring formed by bonding $R_6$, $R_9$, $R_{10}$ or $R_7$, and $R_8$.

Further, the present application provides an organic light emitting device including: a first electrode; a second electrode provided to face the first electrode; and one or more organic material layers provided between the first electrode and the second electrode, in which one or more layers of the organic material layers include the above-described compound.

Advantageous Effects

The compound according to an exemplary embodiment of the present application is used for an organic electronic device including an organic light emitting device, and thus may lower the driving voltage of the organic electronic device and improve the light efficiency, and may enhance lifetime characteristics of the device by thermal stability of the compound.

DESCRIPTION OF DRAWINGS

FIG. 1 illustrates an example of an organic light emitting device in which a substrate 1, a positive electrode 2, a light emitting layer 3, and a negative electrode 4 are sequentially stacked.

FIG. 2 illustrates an example of an organic light emitting device in which a substrate 1, a positive electrode 2, a hole injection layer 5, a hole transport layer 6, a light emitting layer 3, an electron transport layer 7, and a negative electrode 4 are sequentially stacked.

BEST MODE

Hereinafter, the present specification will be described in more detail.

The present specification provides the compound represented by Chemical Formula 1.

Examples of the substituents in the present specification will be described below, but are not limited thereto.

The term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In the present specification, the term "substituted or unsubstituted" means being substituted with one or two or more substituents selected from the group consisting of deuterium; a halogen group; a cyano group; a nitro group; a hydroxy group; an alkyl group; a cycloalkyl group; an alkenyl group; an alkoxy group; an aryl group; and a heterocyclic group, being substituted with a substituent to which two or more substituents among the exemplified substituents are linked, or having no substituent. For example, "the substituent to which two or more substituents are linked" may be a biphenyl group. That is, the biphenyl group may also be an aryl group, and may be interpreted as a substituent to which two phenyl groups are linked.

In the present specification, examples of a halogen group include fluorine, chlorine, bromine or iodine.

In the present specification, the alkyl group may be straight-chained or branch-chained, and the number of carbon atoms thereof is not particularly limited, but is preferably 1 to 50. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tertoctyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, a cycloalkyl group is not particularly limited, but the number of carbon atoms thereof is preferably 3 to 60, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the alkoxy group may be straight-chained, branch-chained, or cyclic. The number of carbon atoms of the alkoxy group is not particularly limited, but is preferably 1 to 20. Specific examples thereof include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present specification, the alkenyl group may be straight-chained or branch-chained, and the number of carbon atoms thereof is not particularly limited, but is preferably 2 to 40. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, when the aryl group is a monocyclic aryl group, the number of carbon atoms thereof is not particularly limited, but is preferably 6 to 25. Specific examples of the monocyclic aryl group include a phenyl group, a biphenyl group, a terphenyl group, and the like, but are not limited thereto.

When the aryl group is a polycyclic aryl group, the number of carbon atoms thereof is not particularly limited, but is preferably 10 to 24. Specific examples of the polycyclic aryl group include a naphthyl group, an anthracenyl group, a phenanthryl group, a pyrenyl group, a perylenyl group, a chrysenyl group, a fluorenyl group, and the like, but are not limited thereto.

In the present specification, the fluorenyl group may be substituted, and adjacent substituents may combine with each other to form a ring.

When the fluorenyl group is substituted, the group may be

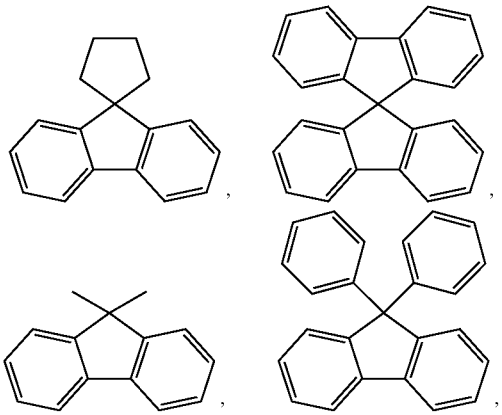

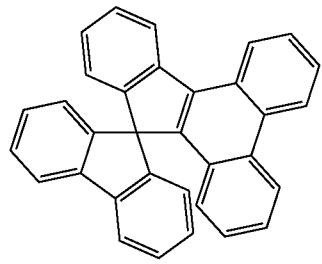

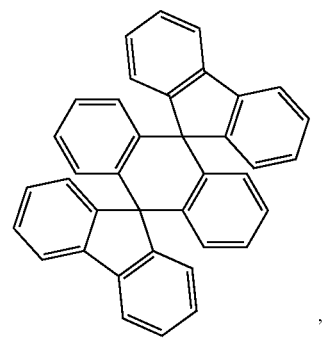

and the like, but is not limited thereto.

In the present specification, a heterocyclic group includes one or more of an atom other than carbon, that is, a heteroatom, and specifically, the heteroatom may include one or more atoms selected from the group consisting of O, N, Se, and S, and the like. The number of carbon atoms of the heterocyclic group is not particularly limited, but is preferably 2 to 60. Examples of the heterocyclic group include a thiophenyl group, a furanyl group, a pyrrole group, an imidazolyl group, a thiazolyl group, an oxazolyl group, an oxadiazolyl group, a triazolyl group, a pyridyl group, a bipyridyl group, a pyrimidyl group, a triazinyl group, an acridyl group, a hydroacridyl group (for example,

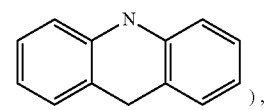), a pyridazinyl group, a pyrazinyl group, a qinolinyl group, a quinazolinyl group, a quinoxalinyl group, a phthalazinyl group, a pyridopyrimidinyl group, a pyridopyrazinyl group, a pyrazinopyrazinyl group, an isoquinolinyl group, an indole group, a carbazolyl group, a benzoxazolyl group, a benzimidazolyl group, a benzothiazolyl group, a benzocarbazolyl group, a dibenzocarbazolyl group, a benzothiophenyl group, a dibenzothiophenyl group, a benzofuranyl group, a dibenzofuranyl group; a benzosilole group; a dibenzosilole group; a phenanthrolinyl group, a thiazolyl group, an isoxazolyl group, an oxadiazolyl group, a thiadiazolyl group, a benzothiazolyl group, a phenothiazinyl group, a phenoxazinyl group, and fused structures thereof, and the like, but are not limited thereto. In addition, examples of the heterocyclic group include a heterocyclic structure including a sulfonyl group, for example,

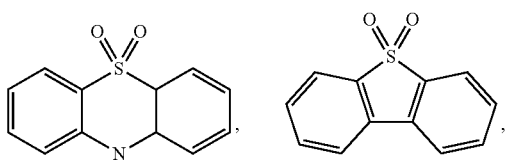

and the like.

In the present specification, the fused structure may be a structure in which an aromatic hydrocarbon ring is fused with the corresponding substituent. Examples of a fused ring of benzimidazole include

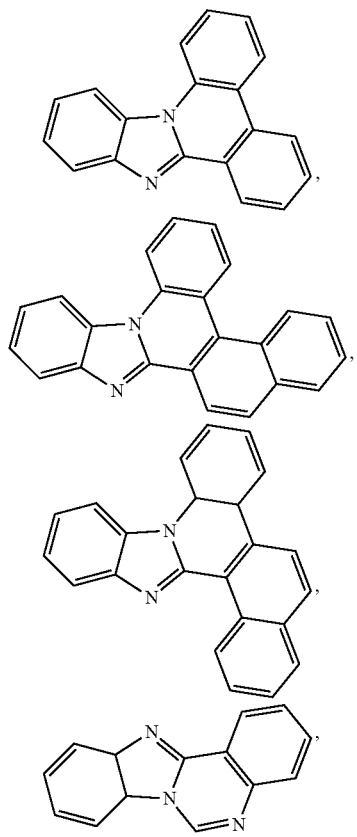

and the like, but are not limited thereto.

In the present specification, the "adjacent" group may mean a substituent substituted with an atom directly linked to an atom in which the corresponding substituent is substituted, or another substituent substituted with an atom in which the corresponding substituent is substituted. For example, two substituents substituted at the ortho position in a benzene ring and two substituents substituted with the same carbon in an aliphatic ring may be interpreted as groups which are "adjacent" to each other.

In the present specification, the case where adjacent groups combine with each other to form a ring means that adjacent groups combine with each other to form a 5-membered to 8-membered hydrocarbon ring or a 5-membered to 8-membered hetero ring as described above, and the ring may be monocyclic or polycyclic, may be an aliphatic ring, an aromatic ring, or a fused form thereof, and is not limited thereto.

According to an exemplary embodiment of the present application, $L_2$ is a direct bond; or a substituted or unsubstituted $C_6$ to $C_{20}$ arylene group.

According to an exemplary embodiment of the present application, $L_2$ is a direct bond.

According to an exemplary embodiment of the present application, $L_2$ is a substituted or unsubstituted phenylene group.

According to an exemplary embodiment of the present application, $L_2$ is a substituted or unsubstituted biphenylene group.

According to an exemplary embodiment of the present application, $L_2$ is a substituted or unsubstituted naphthylene group.

According to an exemplary embodiment of the present application, $Ar_3$ is represented by a substituted phenyl group; a substituted or unsubstituted fluorenyl group; a substituted or unsubstituted benzofluorenyl group; a substituted or unsubstituted spirobifluorenyl group; a substituted or unsubstituted spirofluoreneindenophenanthrene group; a substituted or unsubstituted dispirofluoreneanthracenefluorene group; a substituted or unsubstituted triphenylene group; a $C_4$ to $C_{20}$ heterocyclic group including S or O; a substituted or unsubstituted carbazole group; or any one of Chemical Formulae 6 to 10, when $L_1$ is Chemical Formulae 2 to 4, and $Ar_3$ is represented by a substituted phenyl group; a substituted or unsubstituted fluorenyl group; a substituted or unsubstituted benzofluorenyl group; a substituted or unsubstituted spirobifluorenyl group; a substituted or unsubstituted spirofluoreneindenophenanthrene group; a substituted or unsubstituted dispirofluoreneanthracenefluorene group; a substituted or unsubstituted triphenylene group; a $C_4$ to $C_{20}$ heterocyclic group including S or O; any one of Chemical Formulae 6 to 10, when $L_1$ is Chemical Formula 5.

According to an exemplary embodiment of the present application, $Ar_3$ is a substituted or unsubstituted $C_4$ to $C_{20}$ heteroaryl group including S or O.

According to an exemplary embodiment of the present application, the substituted or unsubstituted heteroaryl group including S or O of $Ar_3$ is a substituted or unsubstituted furan group; or a substituted or unsubstituted thiophene group.

According to an exemplary embodiment of the present application, the substituted or unsubstituted heteroaryl group including S or O of $Ar_3$ is a substituted or unsubstituted dibenzofuran group; or a substituted or unsubstituted dibenzothiophene group.

According to an exemplary embodiment of the present application, $Ar_3$ is a substituted phenyl group; a substituted or unsubstituted fluorenyl group; a substituted or unsubstituted benzofluorenyl group; a substituted or unsubstituted spirobifluorenyl group; a substituted or unsubstituted spirofluoreneindenophenanthrene group; a substituted or unsubstituted dispirofluoreneanthracenefluorene group; a substituted or unsubstituted triphenylene group; a substituted or unsubstituted carbazole group; a substituted or unsubstituted pyrimidyl group; a substituted or unsubstituted pyridazinyl group; a substituted or unsubstituted triazinyl group; a substituted or unsubstituted benzocarbazolyl group; a substituted or unsubstituted benzimidazole group; a substituted or unsubstituted benzoxazole group; a substituted or unsubstituted benzothiazole group; a substituted or unsubstituted dibenzofuran group; a substituted or unsubstituted dibenzothiophene group; a substituted or unsubstituted benzonaphthofuran group; or a substituted or unsubstituted benzonaphthothiophene group, when L1 is Chemical Formulae 2 to 4, Ar$_3$ is a substituted phenyl group; a substituted or unsubstituted fluorenyl group; a substituted or unsubstituted benzofluorenyl group; a substituted or unsubstituted spirobifluorenyl group; a substituted or unsubstituted spirofluoreneindenophenanthrene group; a substituted or unsubstituted dispirofluoreneanthracenefluorene group; a substituted or unsubstituted triphenylene group; a substituted or unsubstituted pyrimidyl group; a substituted or unsubstituted pyridazinyl group; a substituted or unsubstituted triazinyl group; a substituted or unsubstituted benzocarbazolyl group; a substituted or unsubstituted benzimidazole group; a substituted or unsubstituted benzoxazole group; a substituted or unsubstituted benzothiazole group; a substituted or unsubstituted dibenzofuran group; a substituted or unsubstituted dibenzothiophene group; a substituted or unsubstituted benzonaphthofuran group; or a substituted or unsubstituted benzonaphthothiophene group, when L$_1$ is Chemical Formula 5, and the "substituted or unsubstituted" means being unsubstituted or substituted with at least one selected from deuterium; a halogen group; a cyano group; a C$_1$ to C$_{10}$ alkyl group; and a C$_6$ to C$_{10}$ aryl group.

According to an exemplary embodiment of the present application, Ar$_3$ is a substituted phenyl group; a substituted or unsubstituted fluorenyl group; a substituted or unsubstituted benzofluorenyl group; a substituted or unsubstituted spirobifluorenyl group; a substituted or unsubstituted spirofluoreneindenophenanthrene group; a substituted or unsubstituted dispirofluoreneanthracenefluorene group; a substituted or unsubstituted triphenylene group; a substituted or unsubstituted carbazole group; a substituted or unsubstituted pyrimidyl group; a substituted or unsubstituted pyridazinyl group; a substituted or unsubstituted triazinyl group; a substituted or unsubstituted benzocarbazolyl group; a substituted or unsubstituted benzimidazole group; a substituted or unsubstituted benzoxazole group; a substituted or unsubstituted benzothiazole group; a substituted or unsubstituted dibenzofuran group; a substituted or unsubstituted dibenzothiophene group; a substituted or unsubstituted benzonaphthofuran group; or a substituted or unsubstituted benzonaphthothiophene group, when L$_1$ is Chemical Formulae 2 to 4, Ar$_3$ is a substituted phenyl group; a substituted or unsubstituted fluorenyl group; a substituted or unsubstituted benzofluorenyl group; a substituted or unsubstituted spirobifluorenyl group; a substituted or unsubstituted spirofluoreneindenophenanthrene group; a substituted or unsubstituted dispirofluoreneanthracenefluorene group; a substituted or unsubstituted triphenylene group; a substituted or unsubstituted pyrimidyl group; a substituted or unsubstituted pyridazinyl group; a substituted or unsubstituted triazinyl group; a substituted or unsubstituted benzocarbazolyl group; a substituted or unsubstituted benzimidazole group; a substituted or unsubstituted benzoxazole group; a substituted or unsubstituted benzothiazole group; a substituted or unsubstituted dibenzofuran group; a substituted or unsubstituted dibenzothiophene group; a substituted or unsubstituted benzonaphthofuran group; or a substituted or unsubstituted benzonaphthothiophene group, when L$_1$ is Chemical Formula 5, and the "substituted or unsubstituted" means being unsubstituted or substituted with a cyano group; a methyl group; an ethyl group; a phenyl group; and a biphenyl group.

According to an exemplary embodiment of the present application, Ar$_3$ is a phenyl group substituted with a cyano group; a fluorenyl group unsubstituted or substituted with a cyano group, an alkyl group, or an aryl group; a benzofluorenyl group unsubstituted or substituted with an alkyl group or an aryl group; a spirobifluorenyl group; a spirofluoreneindenophenanthrene group; a dispirofluoreneanthracenefluorene group; a triphenylene group; a carbazole group; a pyrimidyl group; a pyridazinyl group; a triazinyl group unsubstituted or substituted with a phenyl group; a benzocarbazolyl group; a benzimidazole group; a benzoxazole group; a benzothiazole group; a dibenzofuran group; a dibenzothiophene group; a benzonaphthofuran group; or a benzonaphthothiophene group, when L$_1$ is Chemical Formulae 2 to 4, and Ar$_3$ is a phenyl group substituted with a cyano group; a fluorenyl group unsubstituted or substituted with a cyano group, an alkyl group, or an aryl group; a benzofluorenyl group unsubstituted or substituted with an alkyl group or an aryl group; a spirobifluorenyl group; a spirofluoreneindenophenanthrene group; a dispirofluoreneanthracenefluorene group; a triphenylene group; a pyrimidyl group; a pyridazinyl group; a triazinyl group unsubstituted or substituted with a phenyl group; a benzocarbazolyl group; a benzimidazole group; a benzoxazole group; a benzothiazole group; a dibenzofuran group; a dibenzothiophene group; a benzonaphthofuran group; or a benzonaphthothiophene group, when L$_1$ is Chemical Formula 5.

According to an exemplary embodiment of the present application, Ar$_3$ is a phenyl group unsubstituted or substituted with a cyano group.

According to an exemplary embodiment of the present application, Ar$_3$ is a fluorenyl group.

According to an exemplary embodiment of the present application, Ar$_3$ is a fluorenyl group substituted with a cyano group.

According to an exemplary embodiment of the present application, Ar$_3$ is a benzofluorenyl group substituted with an aryl group.

According to an exemplary embodiment of the present application, Ar$_3$ is a benzofluorenyl group substituted with a phenyl group.

According to an exemplary embodiment of the present application, Ar$_3$ is a dimethylfluorenyl group.

According to an exemplary embodiment of the present application, Ar$_3$ is a spirobifluorenyl group.

According to an exemplary embodiment of the present application, Ar$_3$ is a spirofluoreneindenophenanthrene group.

According to an exemplary embodiment of the present application, Ar$_3$ is a dispirofluoreneanthracenefluorene group.

According to an exemplary embodiment of the present application, Ar$_3$ is a dimethylfluorenyl group substituted with a cyano group.

According to an exemplary embodiment of the present application, Ar$_3$ is a triphenylene group.

According to an exemplary embodiment of the present application, Ar$_3$ is a pyrimidyl group.

According to an exemplary embodiment of the present application, Ar$_3$ is a pyrimidyl group substituted with an aryl group.

According to an exemplary embodiment of the present application, Ar$_3$ is a pyrimidyl group substituted with a phenyl group, a biphenyl group, a phenanthrene group, or a fluorenyl group.

According to an exemplary embodiment of the present application, Ar$_3$ is a pyridazinyl group.

According to an exemplary embodiment of the present application, Ar$_3$ is a pyridazinyl group substituted with an aryl group.

According to an exemplary embodiment of the present application, $Ar_3$ is a pyridazinyl group substituted with a phenyl group.

According to an exemplary embodiment of the present application, $Ar_3$ is a triazinyl group.

According to an exemplary embodiment of the present application, $Ar_3$ is a benzimidazole group.

According to an exemplary embodiment of the present application, $Ar_3$ is a benzimidazole group substituted with an alkyl group or an aryl group.

According to an exemplary embodiment of the present application, $Ar_3$ is a benzimidazole group substituted with a methyl group.

According to an exemplary embodiment of the present application, $Ar_3$ is a benzimidazole group substituted with a phenyl group.

According to an exemplary embodiment of the present application, $Ar_3$ is a benzoxazole group.

According to an exemplary embodiment of the present application, $Ar_3$ is a benzothiazole group.

According to an exemplary embodiment of the present application, $Ar_3$ is a benzocarbazole group.

According to an exemplary embodiment of the present application, $Ar_3$ is a dibenzothiophene group.

According to an exemplary embodiment of the present application, $Ar_3$ is a dibenzofuran group.

According to an exemplary embodiment of the present application, $Ar_3$ is a benzonaphthothiophene group.

According to an exemplary embodiment of the present application, $Ar_3$ is a benzonaphthofuran group.

According to an exemplary embodiment of the present application, Chemical Formula 6 is represented by any one of the following Chemical Formulae 6-1-1 to 6-1-3.

[Chemical Formula 6-1-1]

[Chemical Formula 6-1-2]

[Chemical Formula 6-1-3]

In Chemical Formulae 6-1-1 to 6-1-3, R1 and m are the same as those described above.

According to an exemplary embodiment of the present application, Chemical Formula 6 is represented by any one of the following Chemical Formulae 6-2-1 to 6-2-3.

[Chemical Formula 6-2-1]

[Chemical Formula 6-2-2]

[Chemical Formula 6-2-3]

In Chemical Formulae 6-2-1 to 6-2-3, $X_1$, $R_1$, and m are the same as those described above.

According to an exemplary embodiment of the present application, Chemical Formula 7 is represented by any one of the following Chemical Formulae 7-1 to 7-6.

[Chemical Formula 7-1]

[Chemical Formula 7-2]

[Chemical Formula 7-3]

[Chemical Formula 7-4]

[Chemical Formula 7-5]

[Chemical Formula 7-6]

In Chemical Formulae 7-1 to 7-6, $X_2$ to $X_6$ are the same as CR' described above.

According to an exemplary embodiment of the present application, Chemical Formula 8 is represented by any one of the following Chemical Formulae 8-1 to 8-3.

[Chemical Formula 8-1]

[Chemical Formula 8-2]

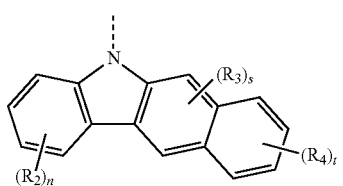

[Chemical Formula 8-3]

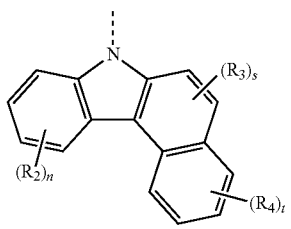

In Chemical Formulae 8-1 to 8-3, $R_2$ to $R_4$, n, s, and t are the same as those described above.

According to an exemplary embodiment of the present application, Chemical Formula 9 is represented by any one of the following Chemical Formulae 9-1 to 9-4.

[Chemical Formula 9-1]

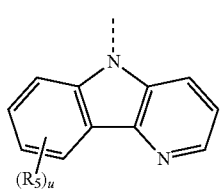

[Chemical Formula 9-2]

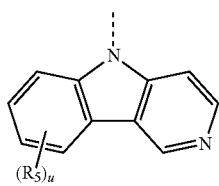

[Chemical Formula 9-3]

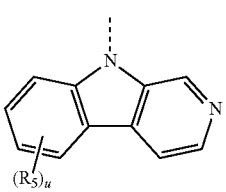

[Chemical Formula 9-4]

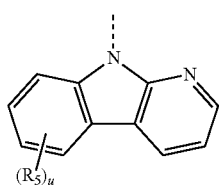

In Chemical Formulae 9-1 to 9-4, R5 and u are the same as those described above.

According to an exemplary embodiment of the present application, Chemical Formula 10 is represented by the following Chemical Formula 10-1 or 10-2.

[Chemical Formula 10-1]

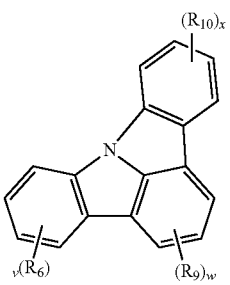

[Chemical Formula 10-2]

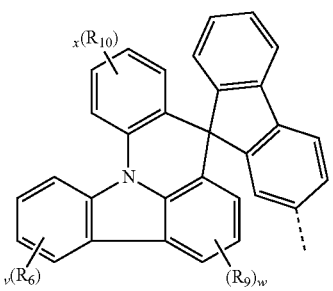

In Chemical Formulae 10-1 and 10-2, $R_6$, $R_9$, $R_{10}$, v, w, and x are the same as those described above, and " ------ " means a moiety bonded to $L_2$ of Chemical Formula 1, and the bonding moiety of Chemical Formula 10-1 is $R_6$, $R_9$, or $R_{10}$.

According to an exemplary embodiment of the present application, $Ar_1$ and $Ar_2$ are the same as or different from each other, and are each independently a substituted or unsubstituted $C_6$ to $C_{20}$ aryl group.

According to an exemplary embodiment of the present application, $Ar_1$ and $Ar_2$ are the same as or different from each other, and are each independently a substituted or unsubstituted phenyl group; a substituted or unsubstituted biphenyl group; or a substituted or unsubstituted naphthyl group.

According to an exemplary embodiment of the present application, $Ar_1$ and $Ar_2$ are a phenyl group.

According to an exemplary embodiment of the present application, $S_1$ to $S_4$ are the same as or different from each other, and are each independently hydrogen; deuterium; a halogen group; a $C_1$ to $C_{10}$ alkyl group; a $C_6$ to $C_{10}$ aryl group; or a $C_2$ to $C_{10}$ heterocyclic group.

According to an exemplary embodiment of the present application, $S_1$ to $S_4$ are hydrogen.

According to an exemplary embodiment of the present application, $R_1$ to $R_4$ are hydrogen.

According to an exemplary embodiment of the present application, $R_1$ to $R_6$, $R_9$, and $R_{10}$ are hydrogen.

According to an exemplary embodiment of the present application, the compound represented by Chemical Formula 1 is any one selected from the following structural formulae.

Compound 1-1
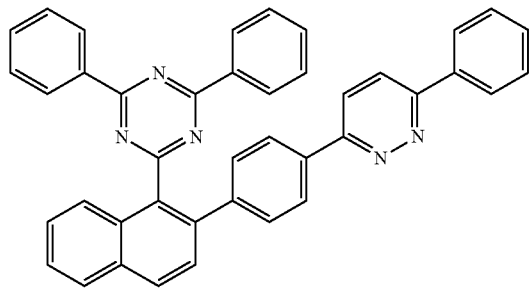
Compound 1-2
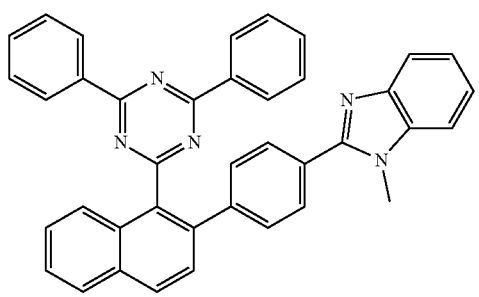
Compound 1-3
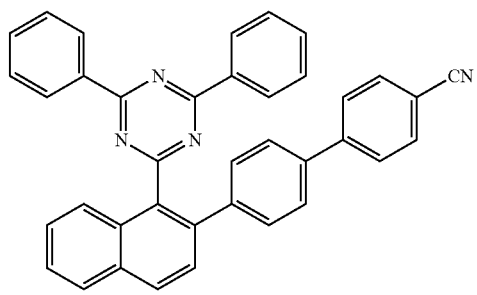
Compound 1-4
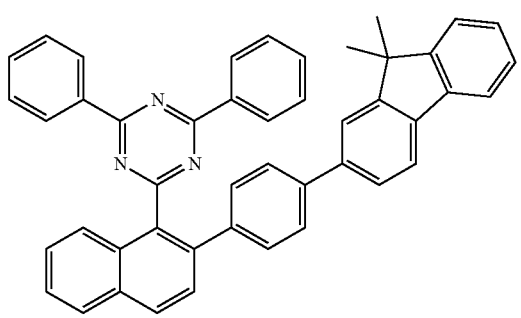
Compound 1-5
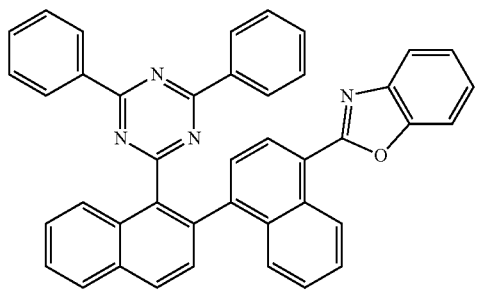
Compound 1-6
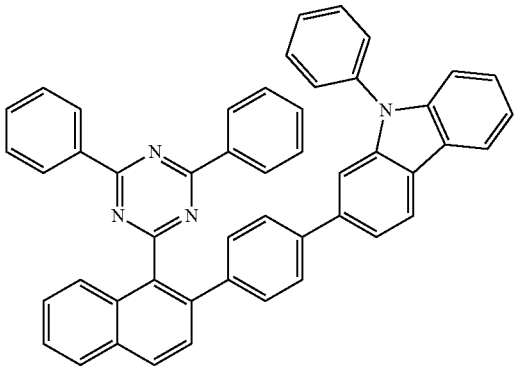
Compound 1-7
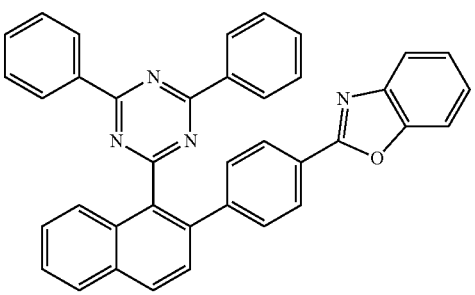
Compound 1-8
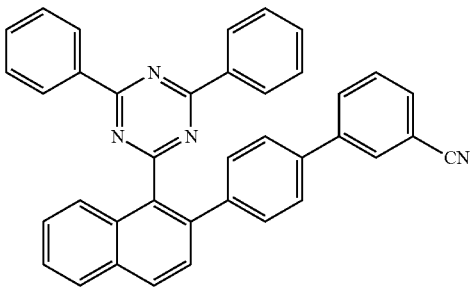
Compound 1-9
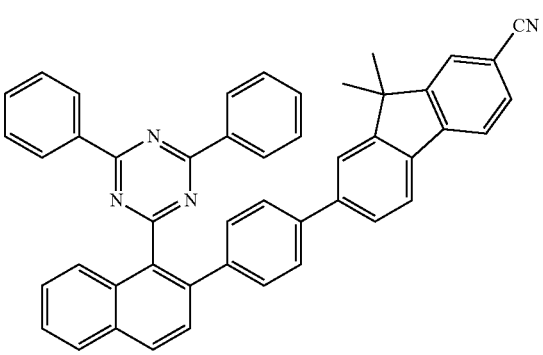

Compound 1-10
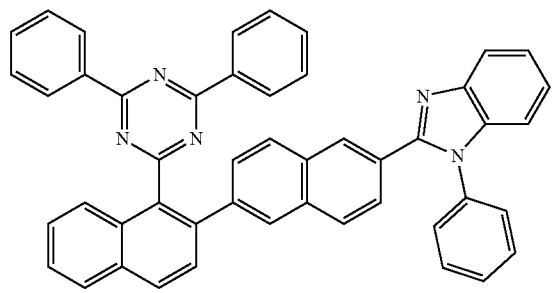
Compound 1-11
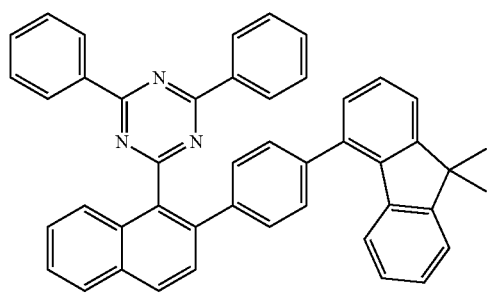
Compound 1-12
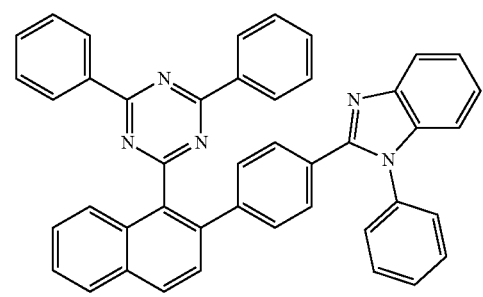
Compound 1-13
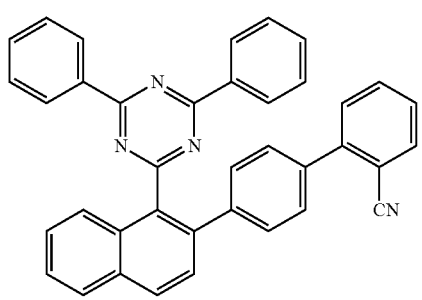
Compound 1-14
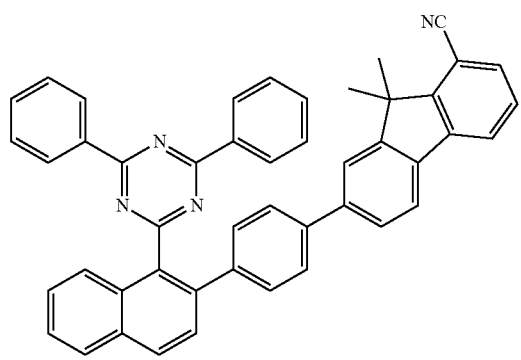
Compound 1-15
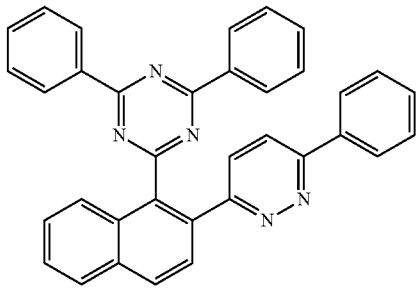
Compound 1-16
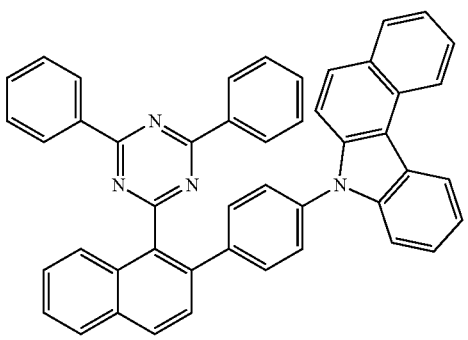
Compound 1-17
Compound 1-18
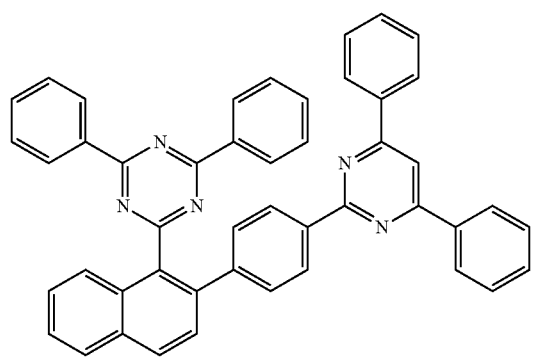

Compound 1-19
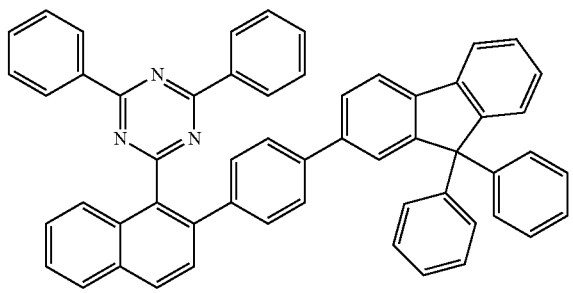
Compound 1-20
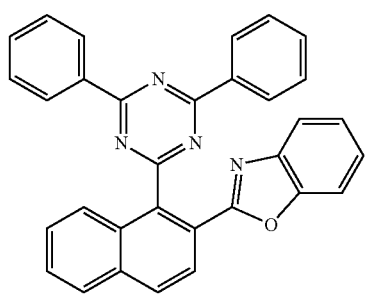
Compound 1-21
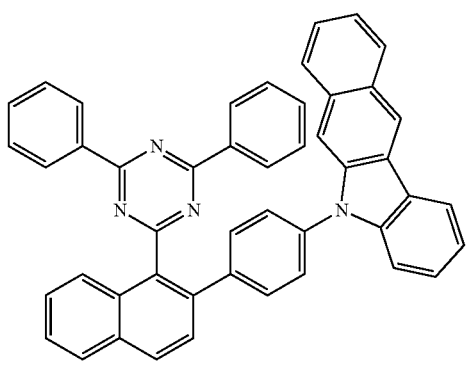
Compound 1-22
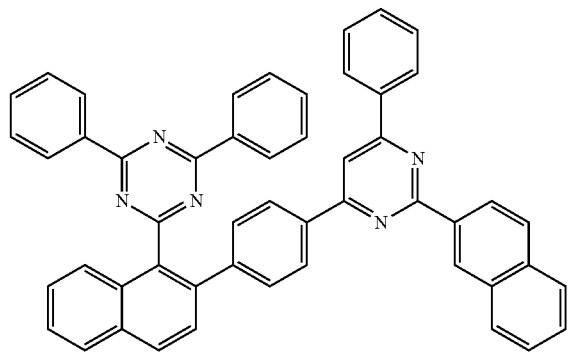
Compound 1-23
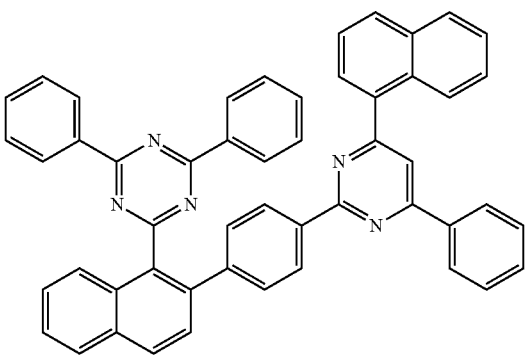
Compound 1-24
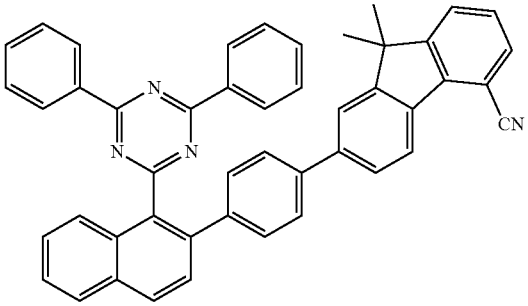
Compound 1-25
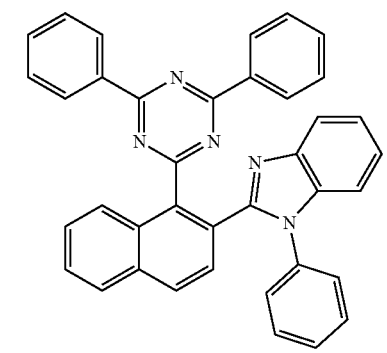
Compound 1-26
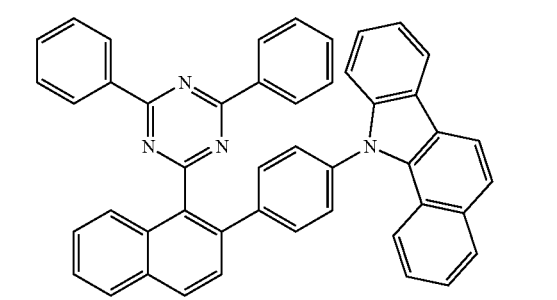

Compound 1-27
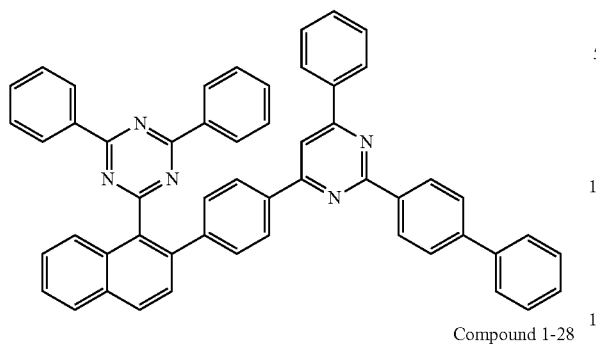
Compound 1-28
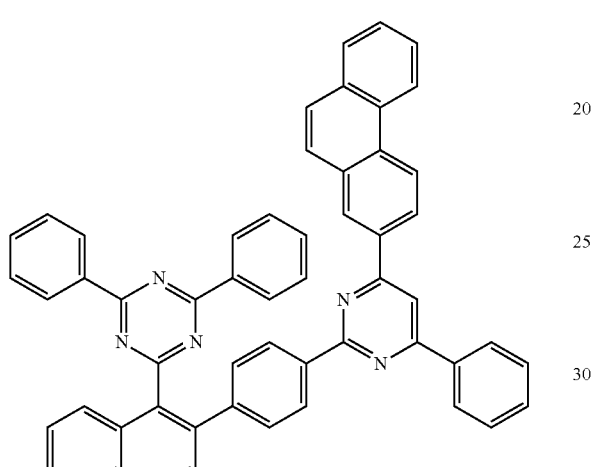
Compound 1-29
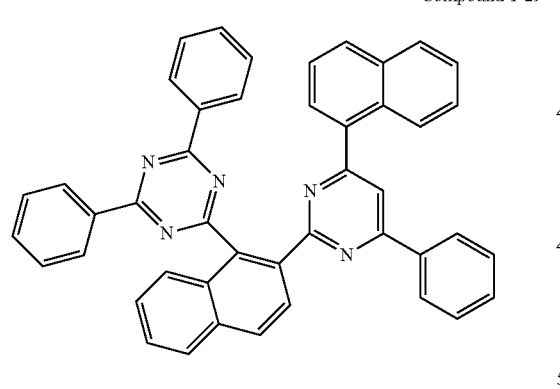
Compound 1-30
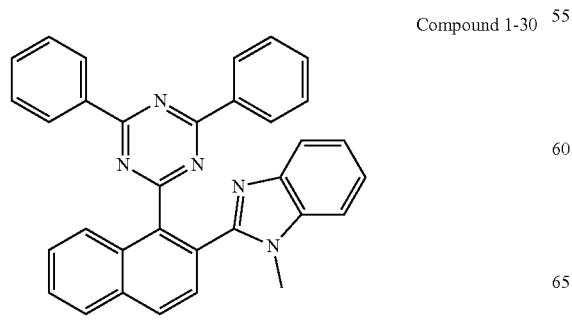
Compound 1-31
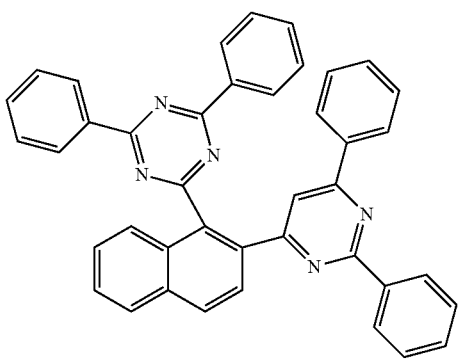
Compound 1-32
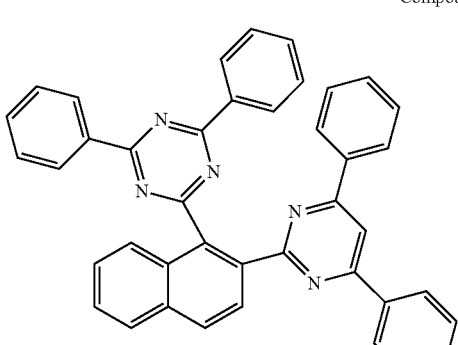
Compound 1-33
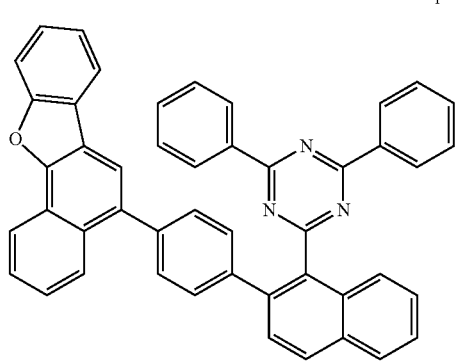
Compound 1-34
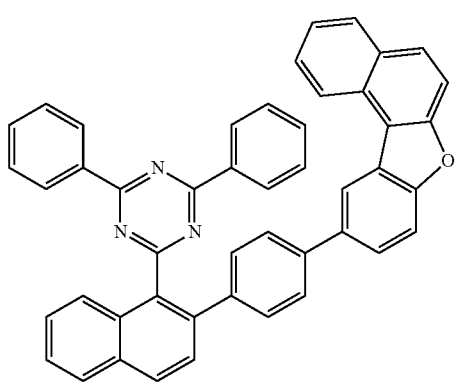

Compound 1-35
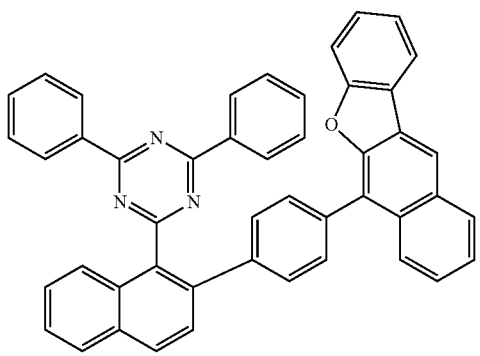
Compound 1-36
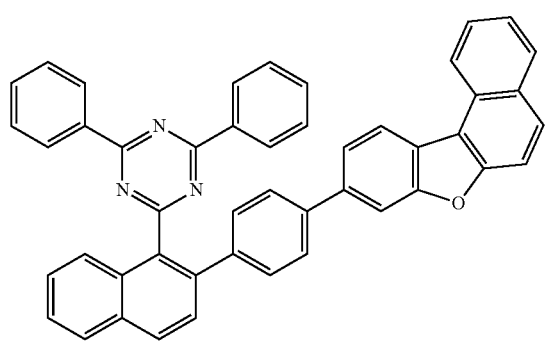
Compound 1-37
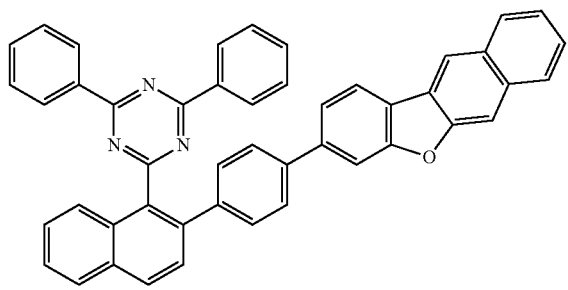
Compound 1-38
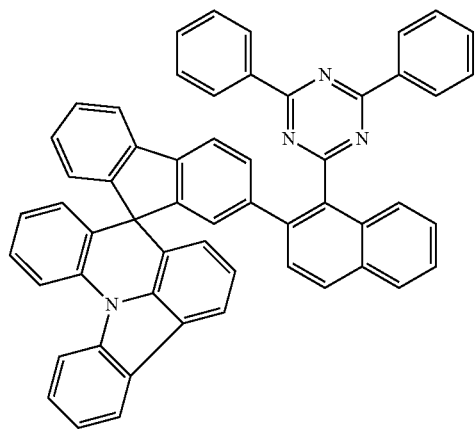
Compound 1-39
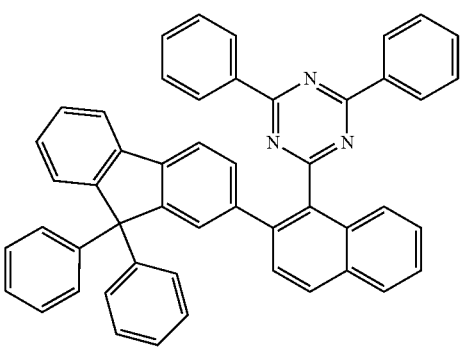
Compound 1-40
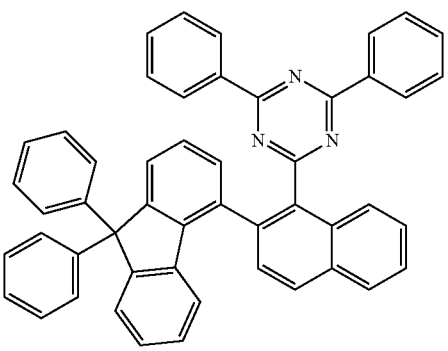
Compound 1-41
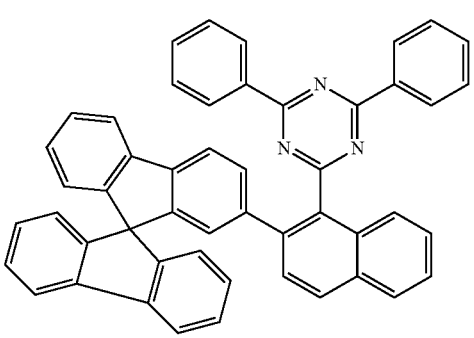
Compound 1-42
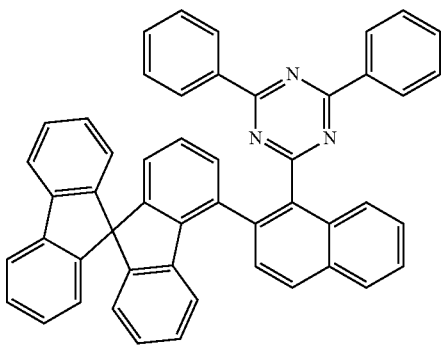

Compound 1-43
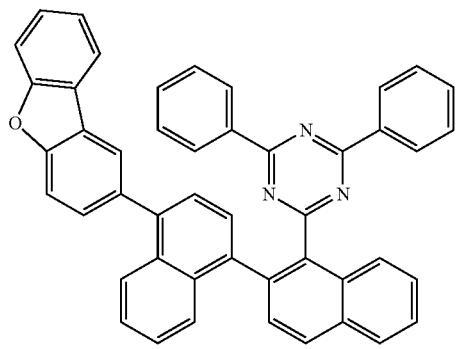
Compound 1-44
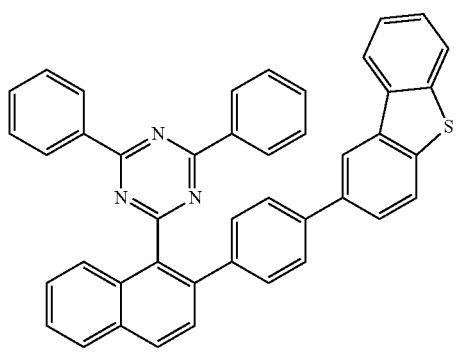
Compound 1-45
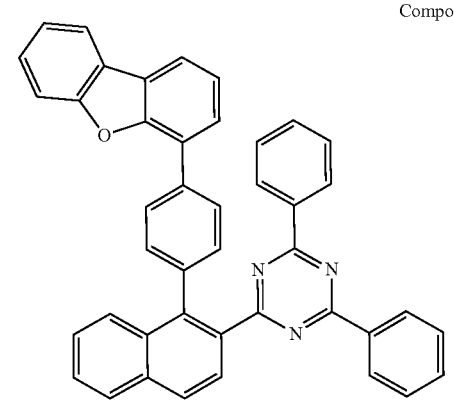
Compound 1-46
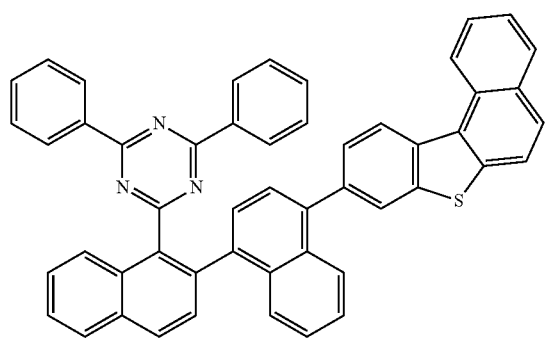
Compound 1-47
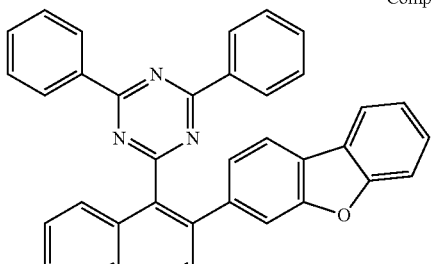
Compound 1-48
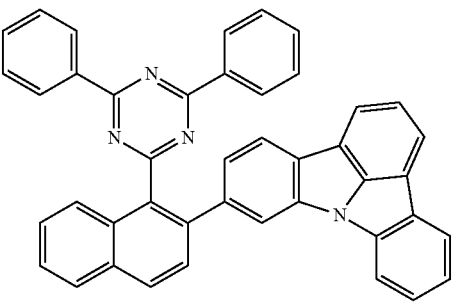
Compound 1-49
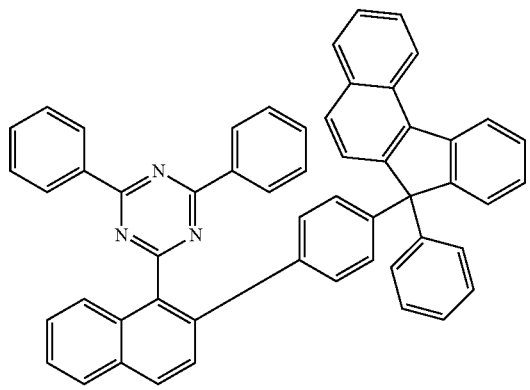
Compound 1-50
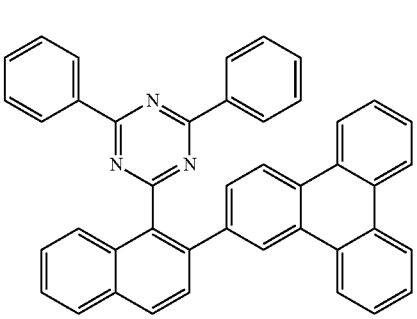

Compound 1-51
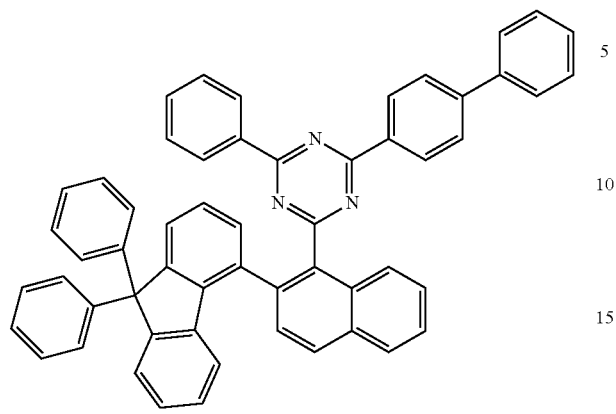
Compound 1-52
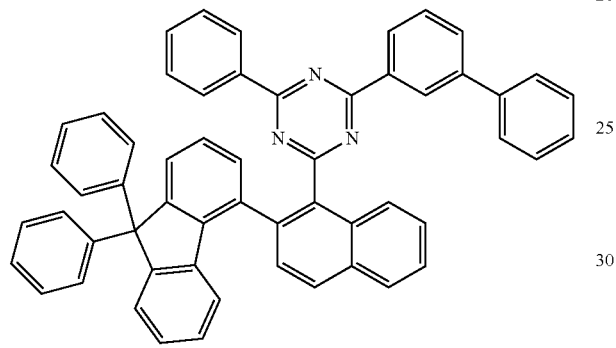
Compound 1-53
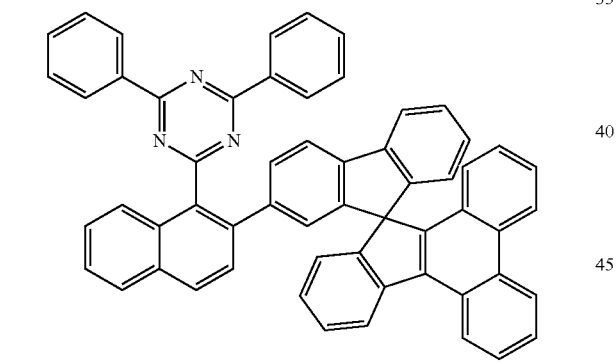
Compound 1-54
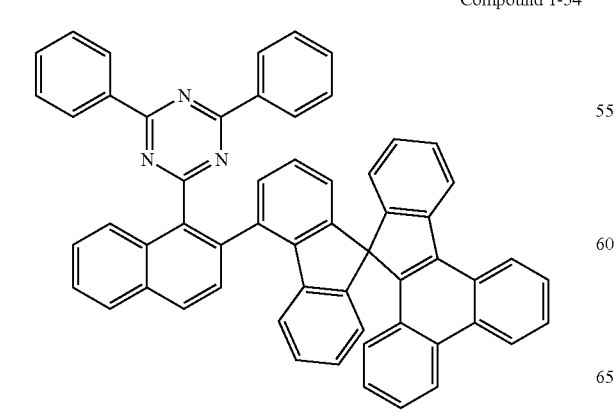
Compound 1-55
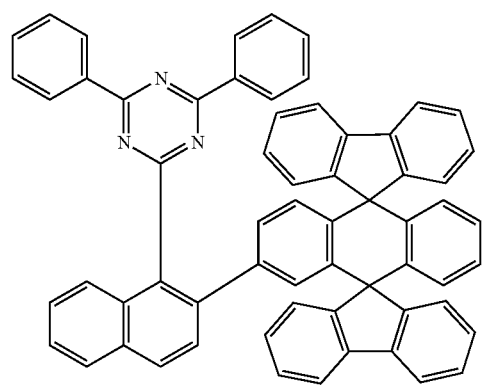
Compound 1-56
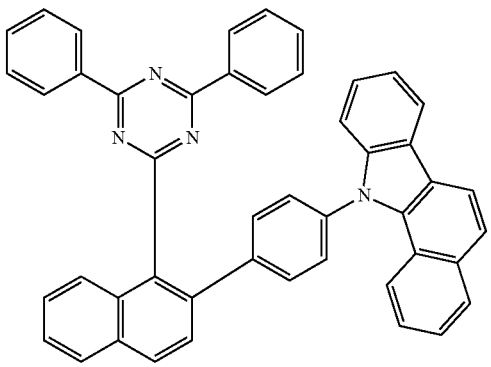
Compound 1-57
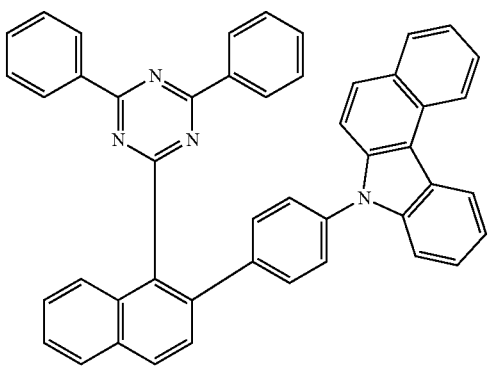

-continued
Compound 2-1
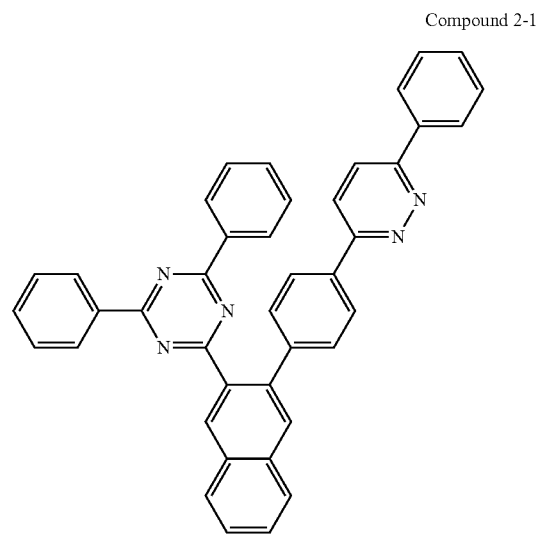
Compound 2-2
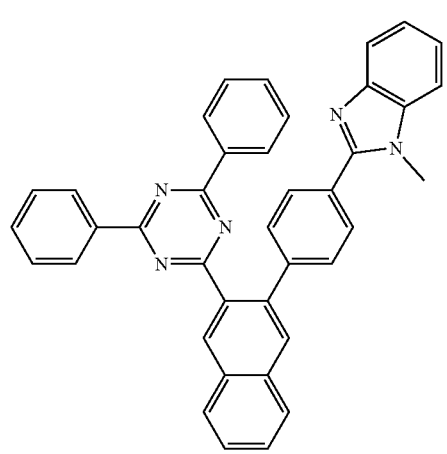
Compound 2-3
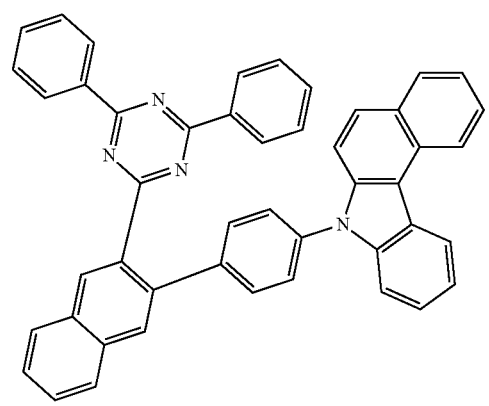
Compound 2-4
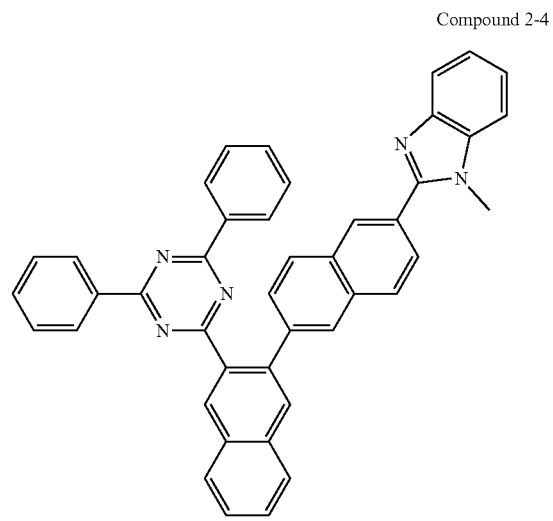
Compound 2-5
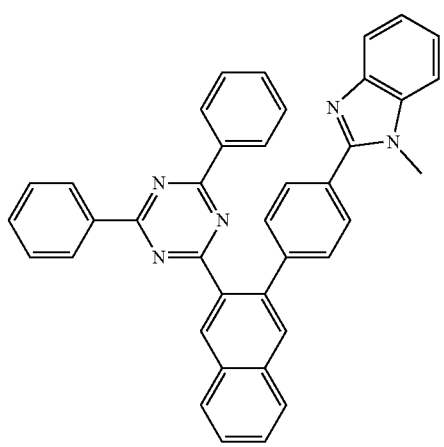
Compound 2-6
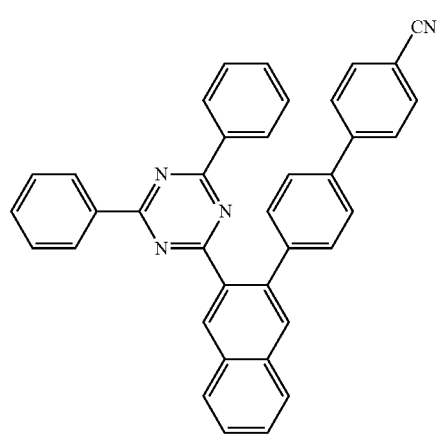

Compound 2-7
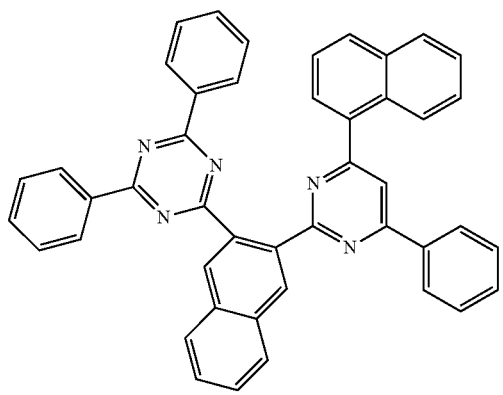
Compound 2-8
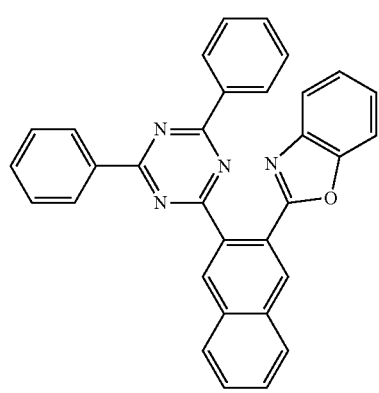
Compound 2-9
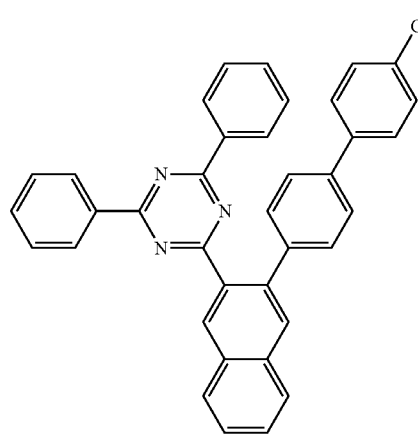
Compound 2-10
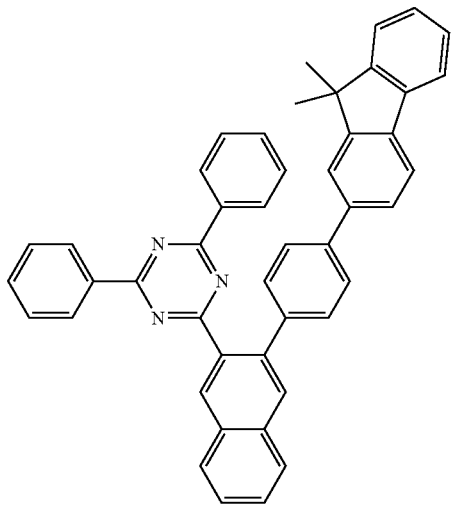
Compound 2-11
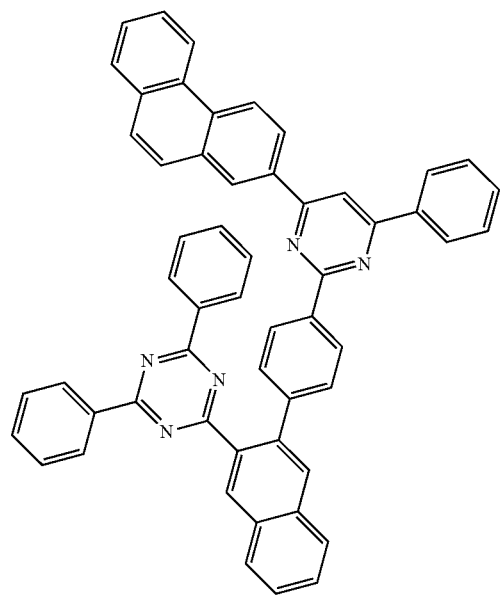
Compound 2-12
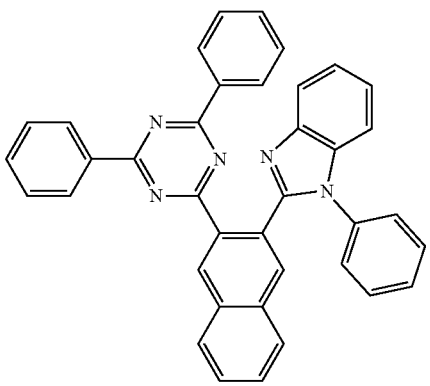

Compound 2-13
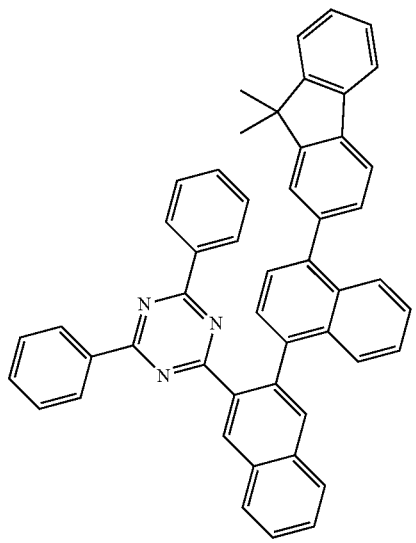
Compound 2-14
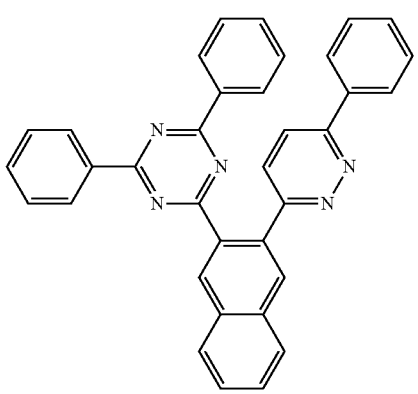
Compound 2-15
Compound 2-16
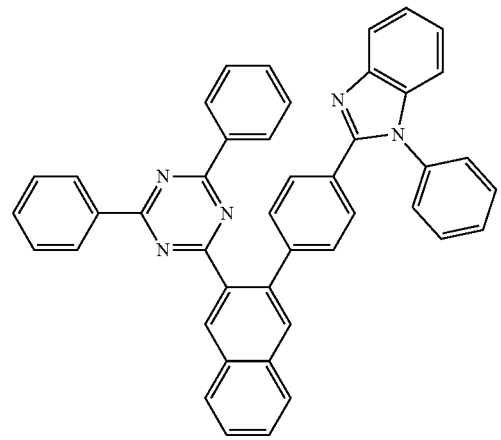
Compound 2-17
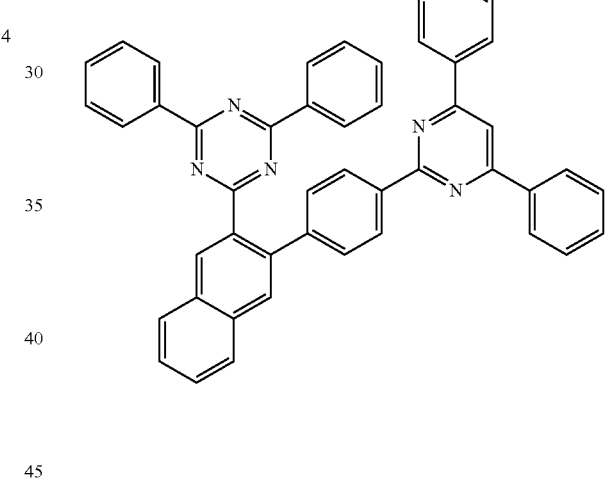
Compound 2-18
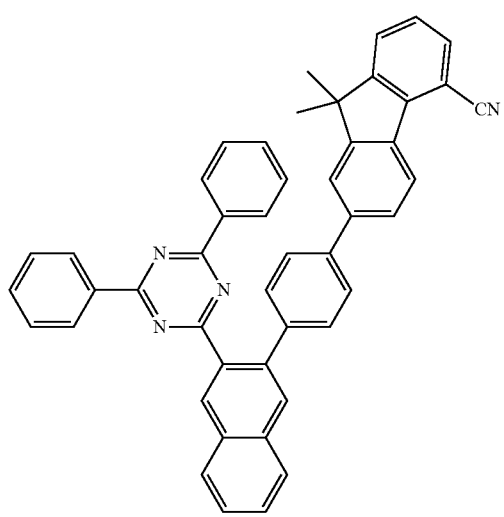

-continued
Compound 2-39
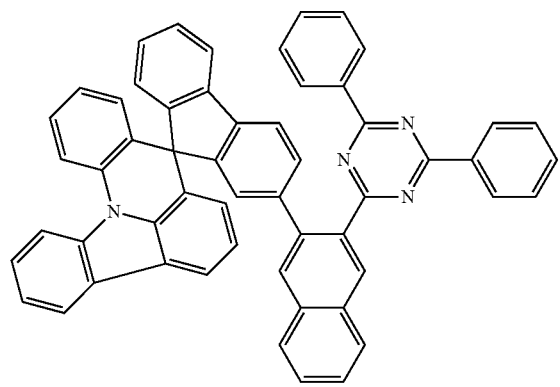
Compound 2-19
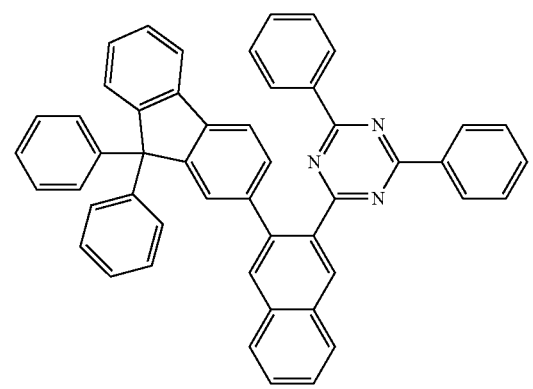
Compound 2-20
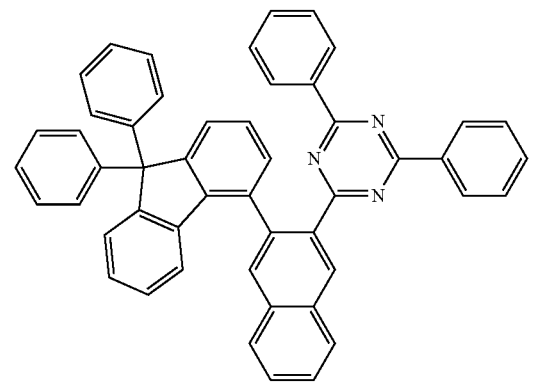
Compound 2-21
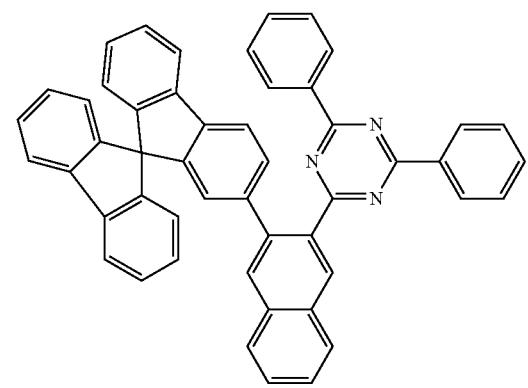
Compound 2-22
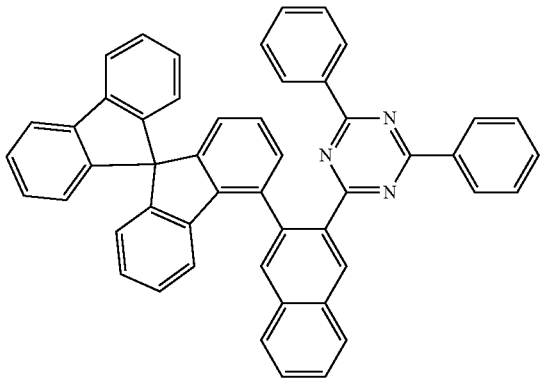
Compound 2-23
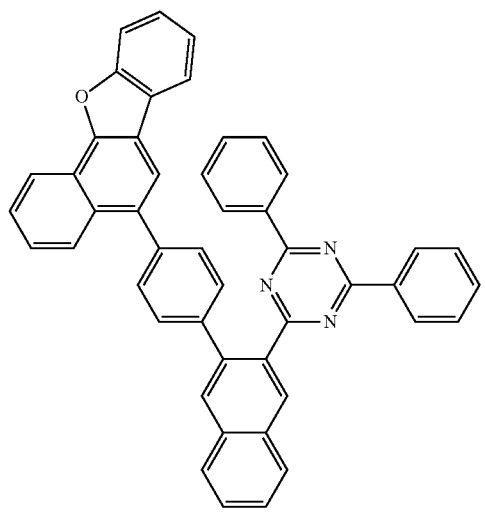
Compound 2-24
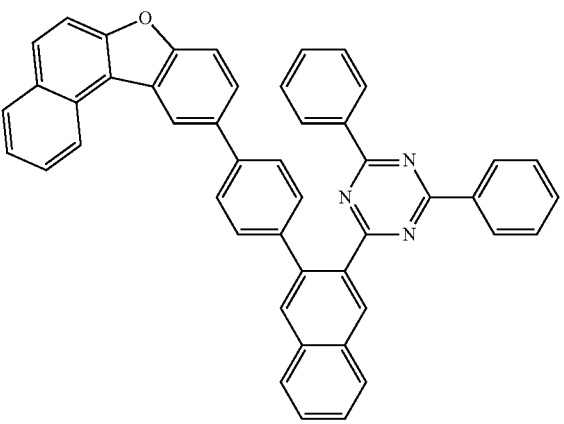

Compound 2-25
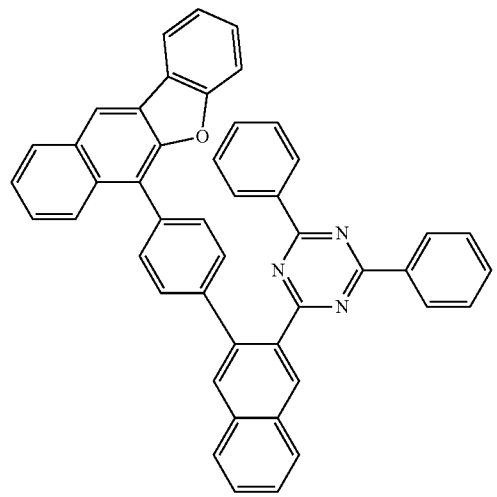
Compound 2-26
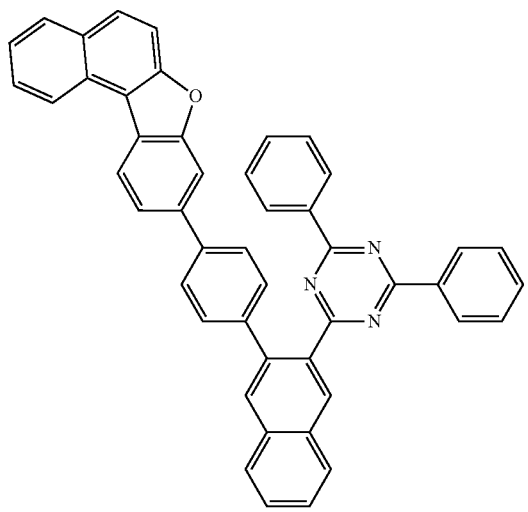
Compound 2-27
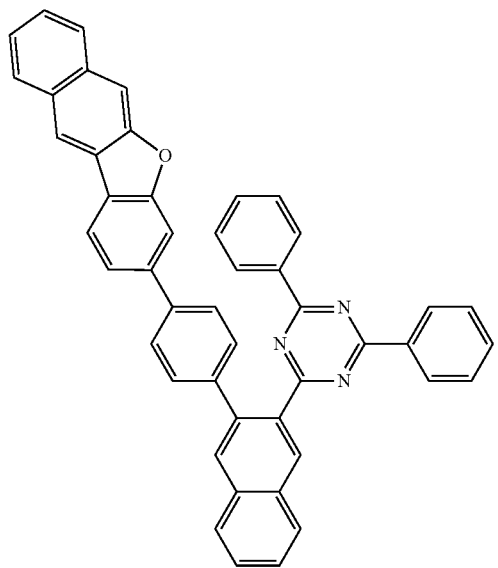
Compound 2-28
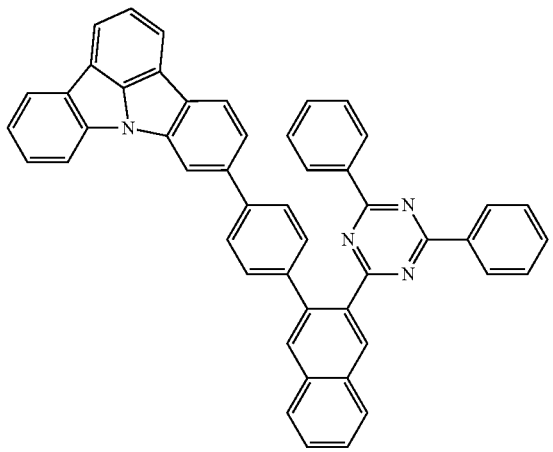
Compound 2-29
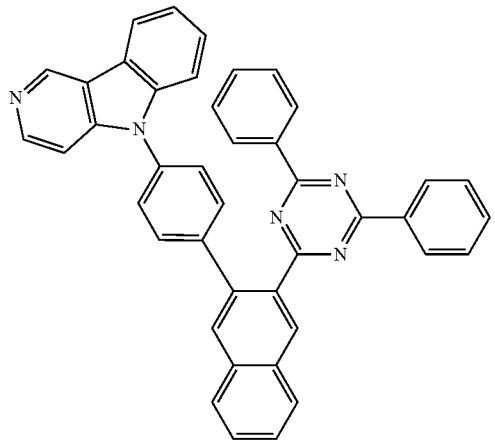
Compound 2-30
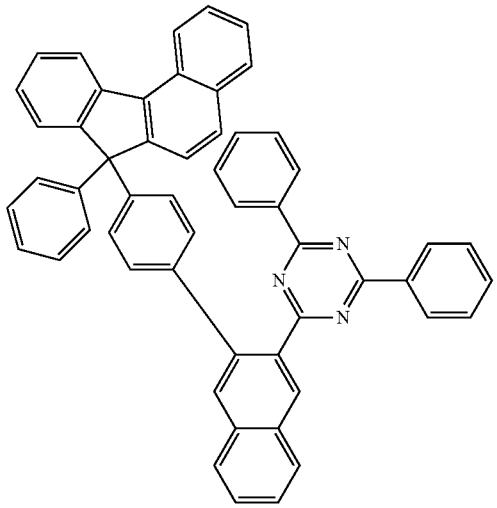

Compound 2-31
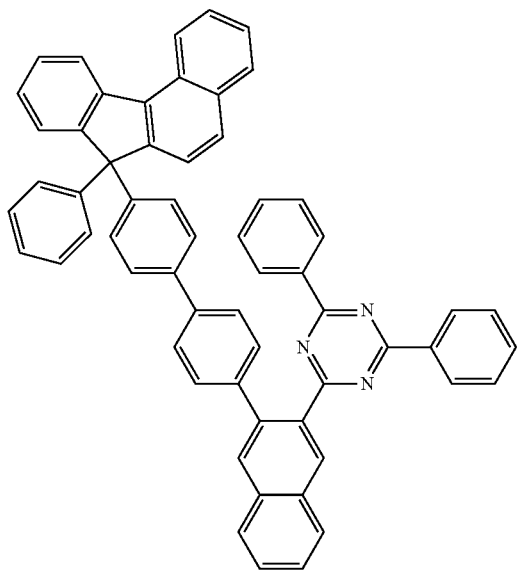
Compound 2-32
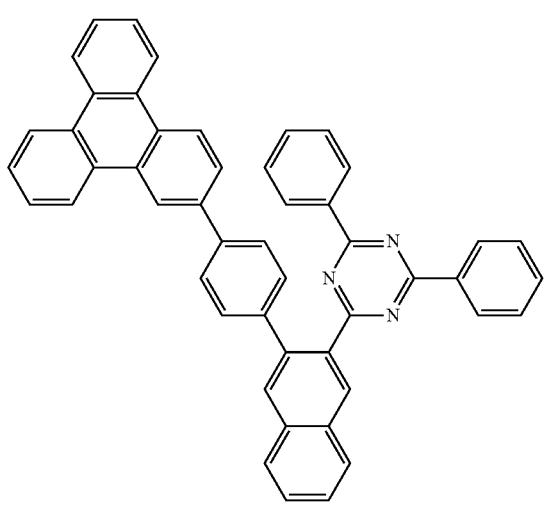
Compound 2-33
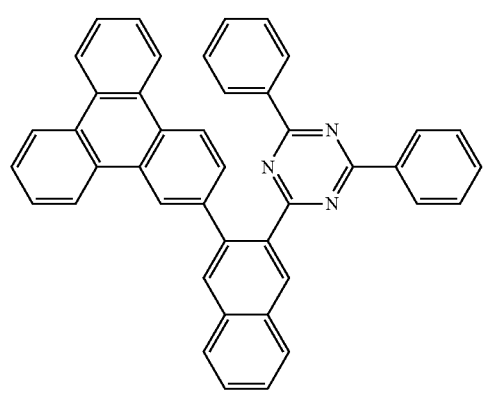
Compound 2-34
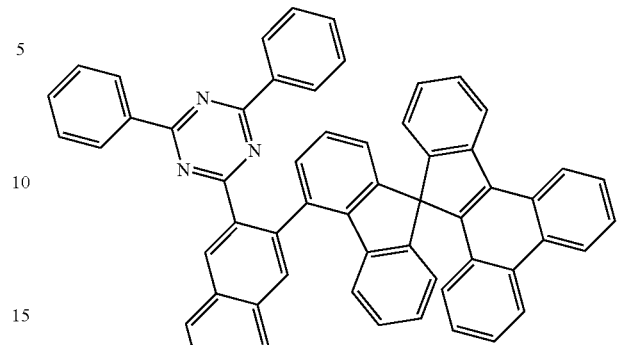
Compound 2-35
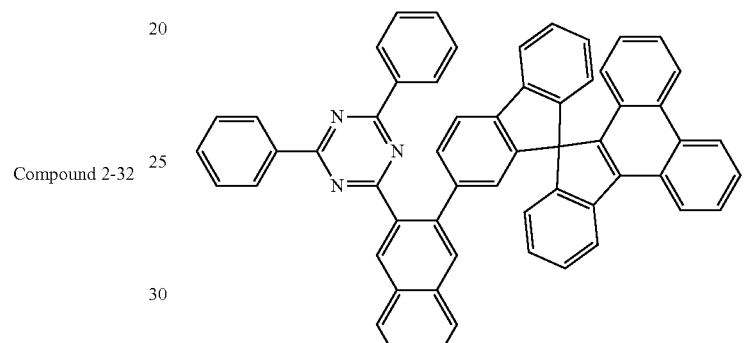
Compound 2-36
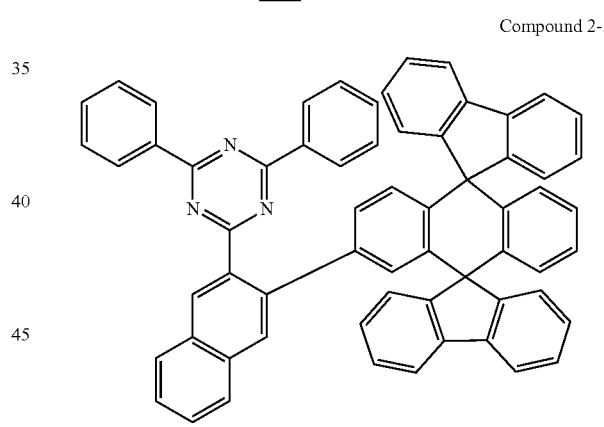
Compound 2-37
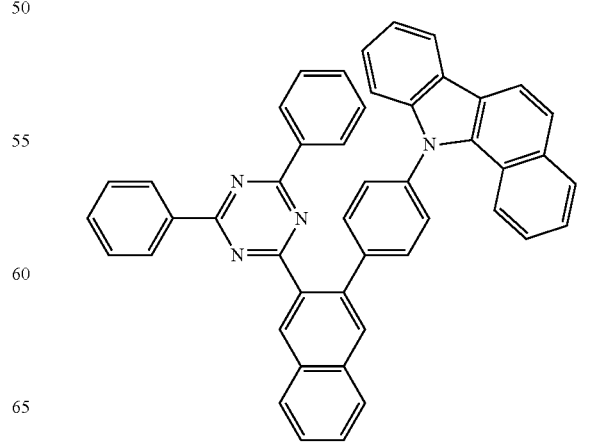

-continued
Compound 2-38
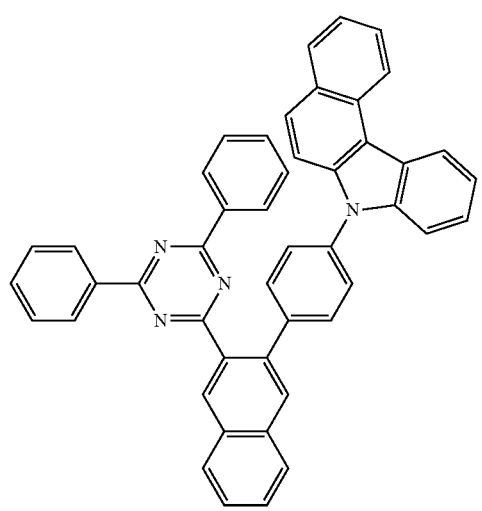
Compound 3-1
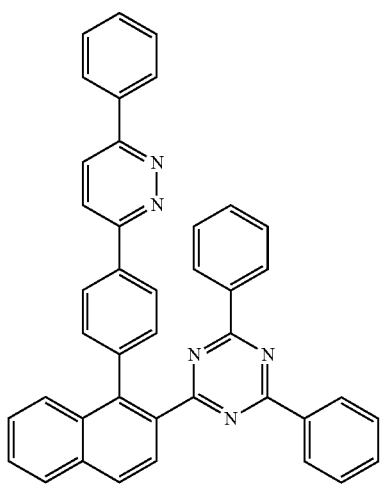
Compound 3-2
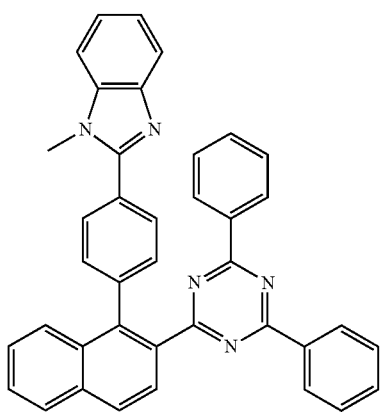
Compound 3-3
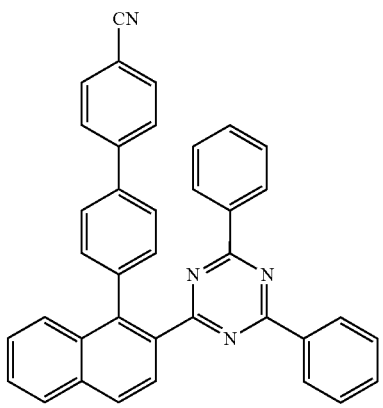
Compound 3-4
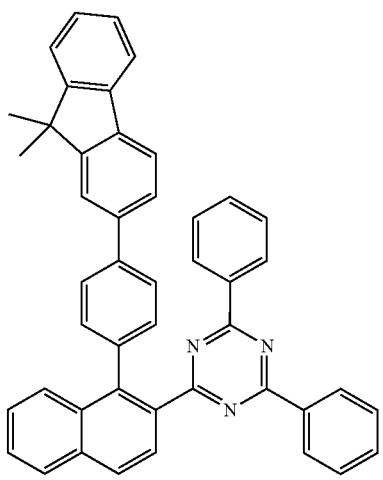
Compound 3-5
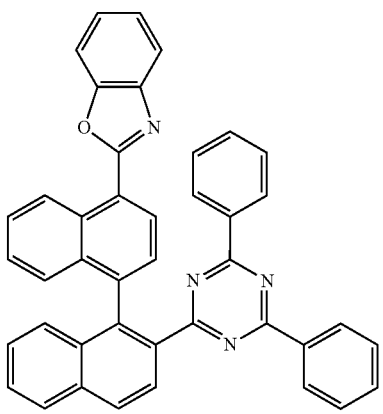

-continued
Compound 3-6
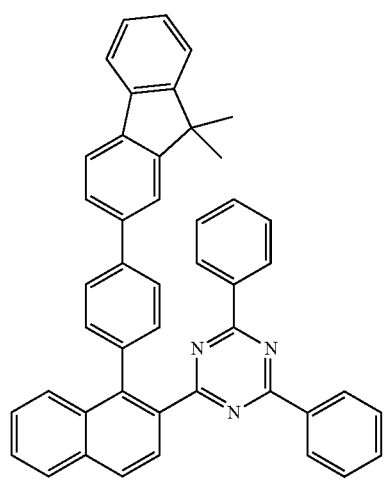
Compound 3-7
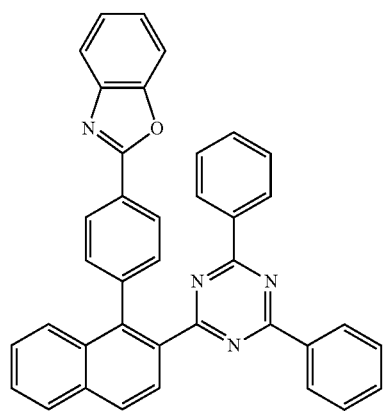
Compound 3-8
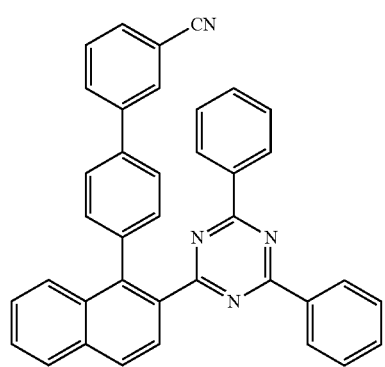
Compound 3-9
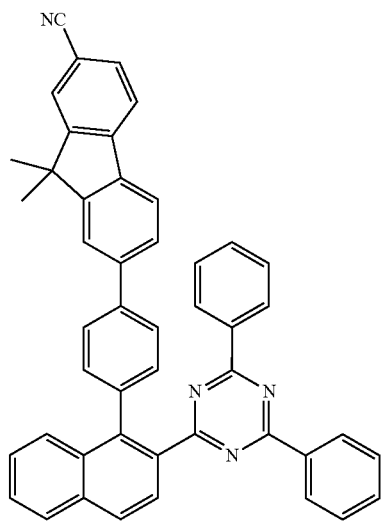
Compound 3-10
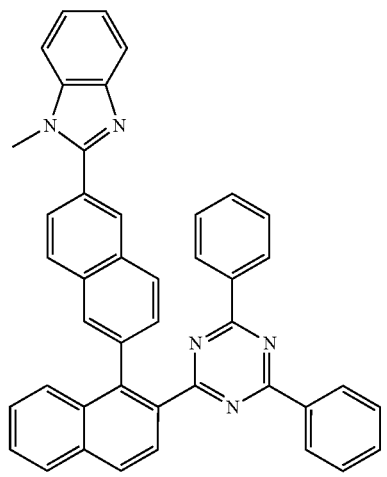
Compound 3-11
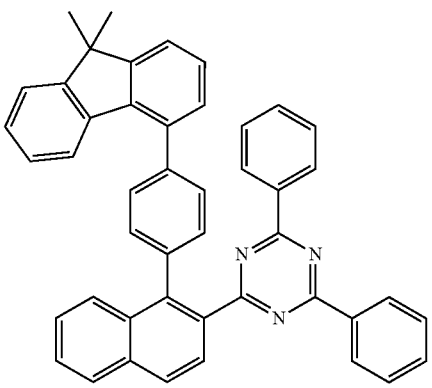

Compound 3-12
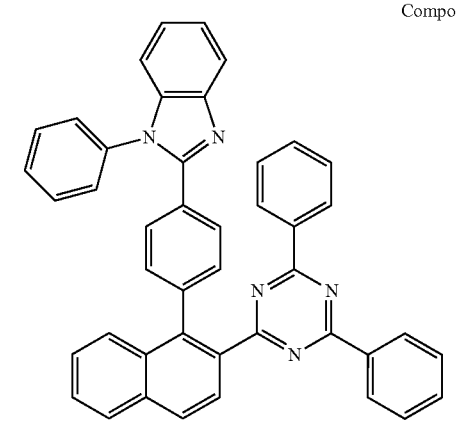
Compound 3-16
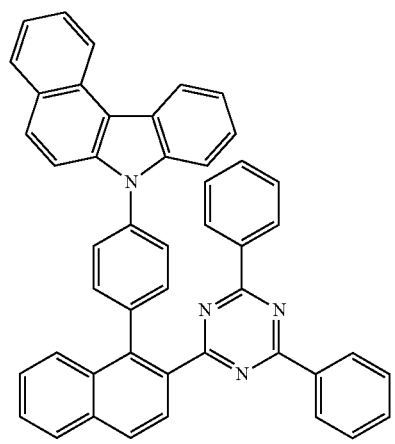
Compound 3-13
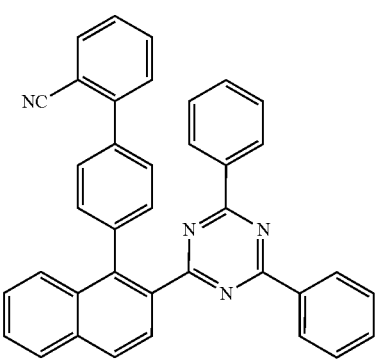
Compound 3-14
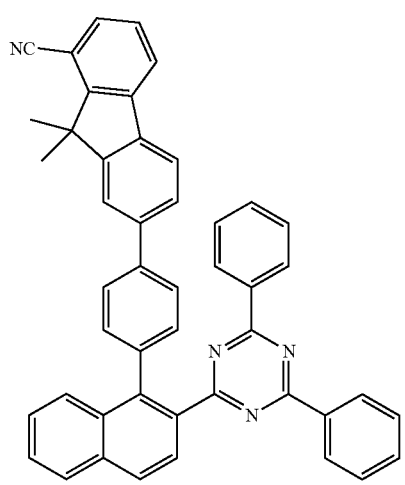
Compound 3-17
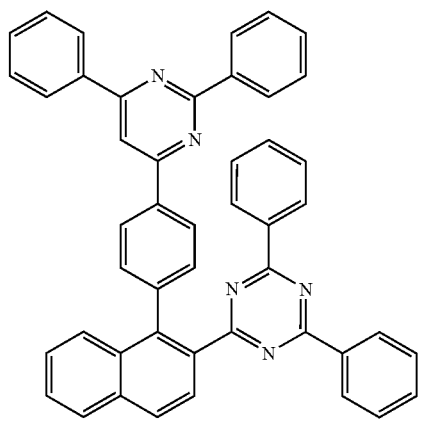
Compound 3-15
Compound 3-18
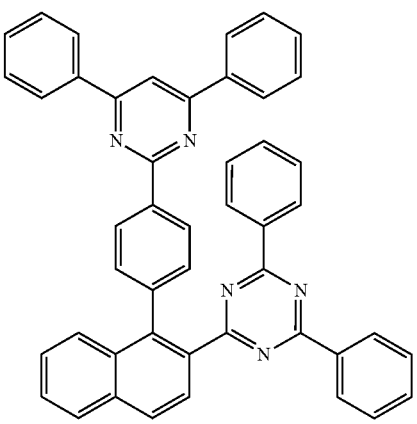

Compound 3-19
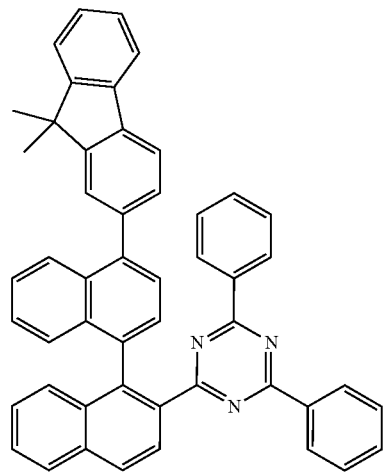
Compound 3-20
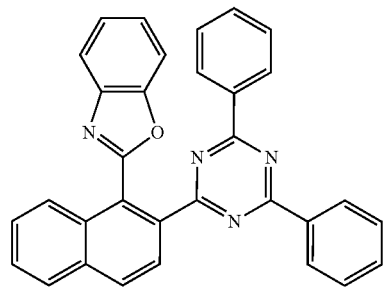
Compound 3-21
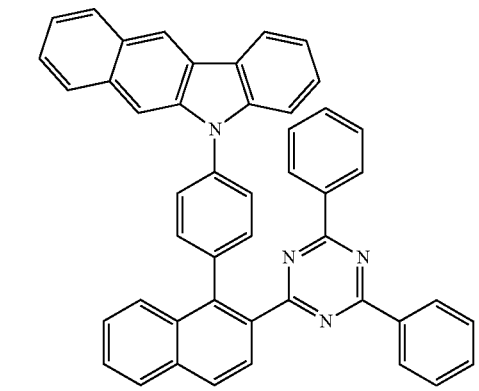
Compound 3-22
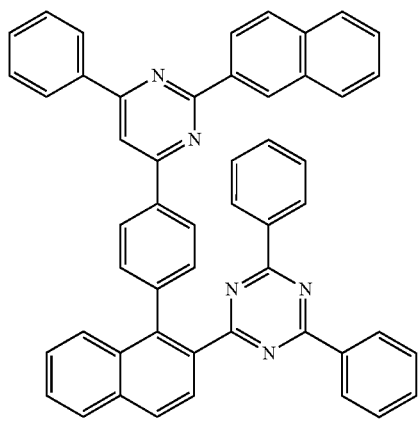
Compound 3-23
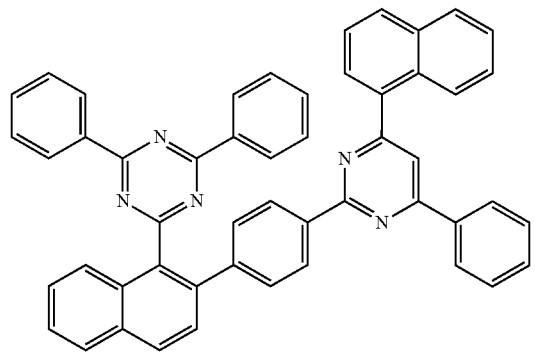
Compound 3-24
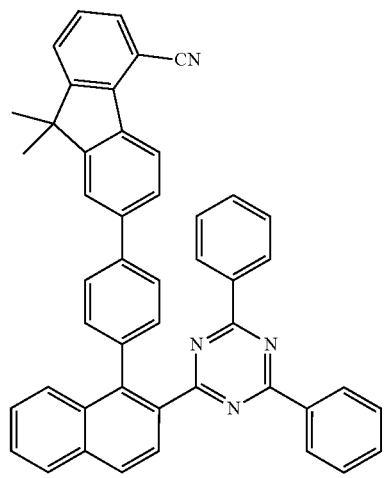
Compound 3-25
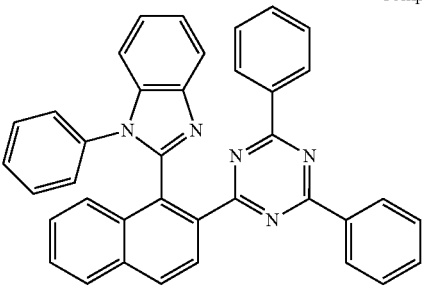
Compound 3-26
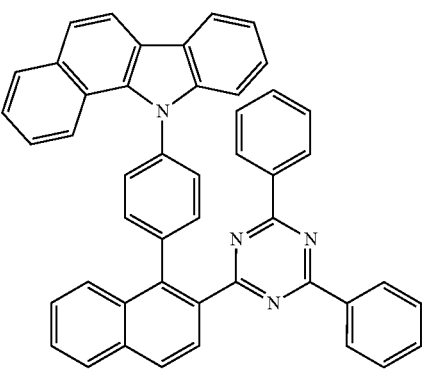

Compound 3-27
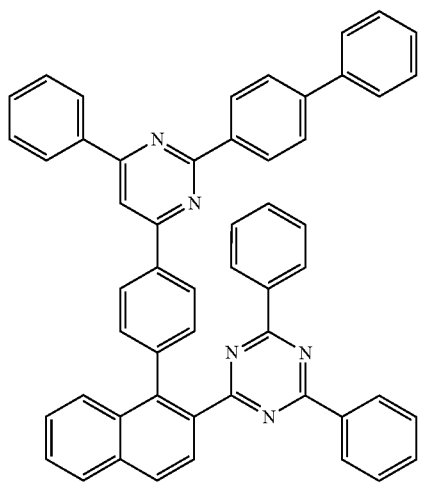
Compound 3-28
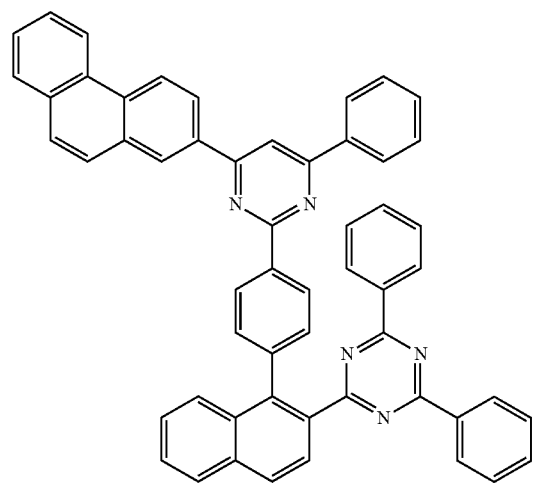
Compound 3-29
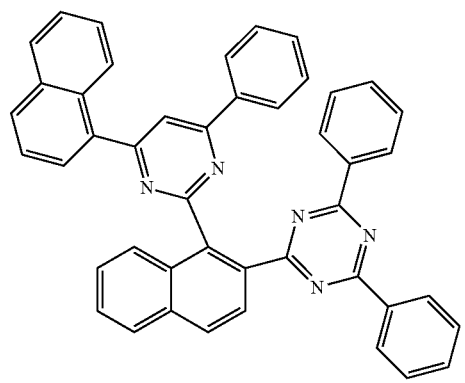
Compound 3-30
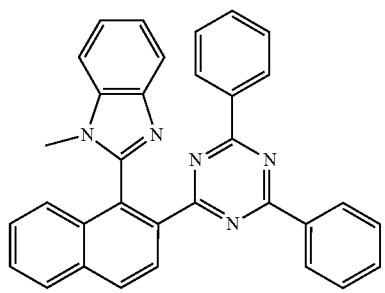
Compound 3-31
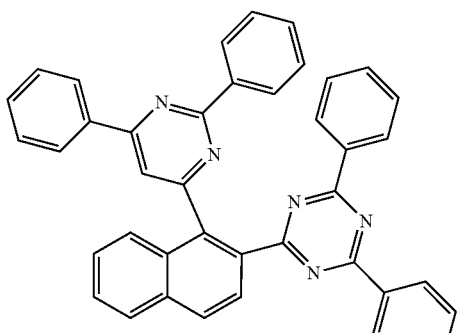
Compound 3-32
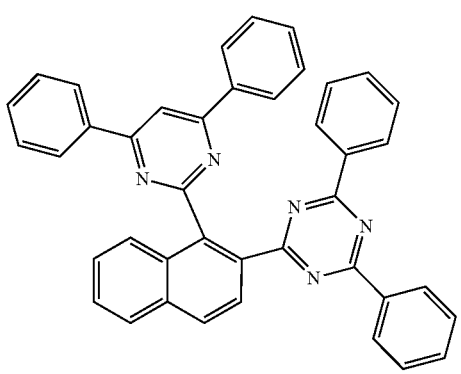
Compound 3-33
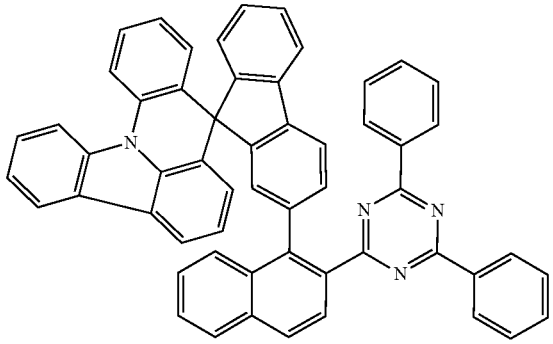

Compound 3-34
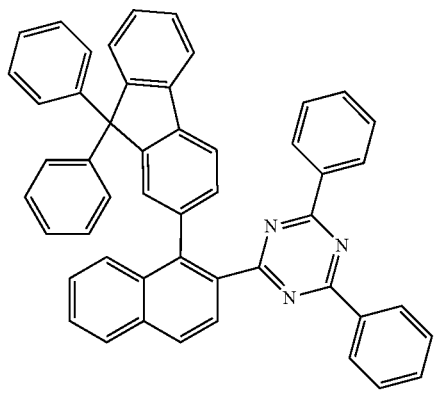
Compound 3-35
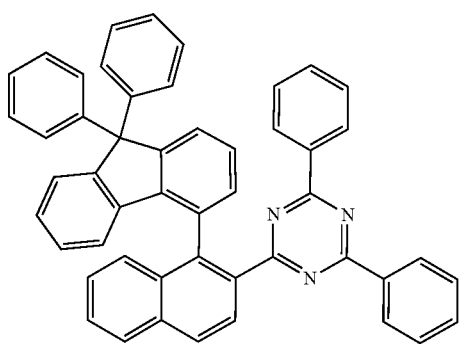
Compound 3-36
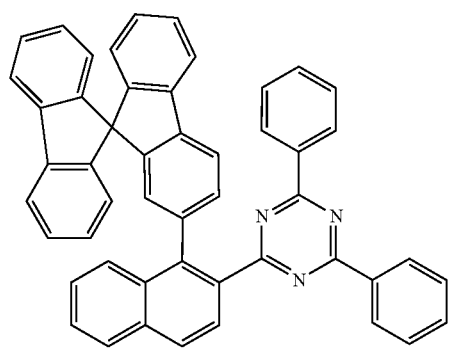
Compound 3-37
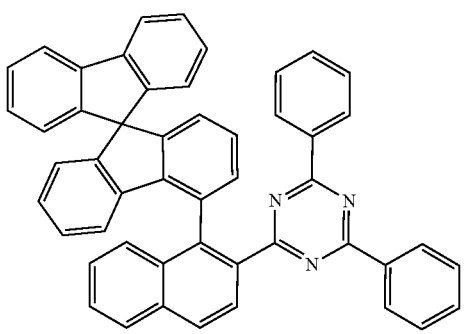
Compound 3-38
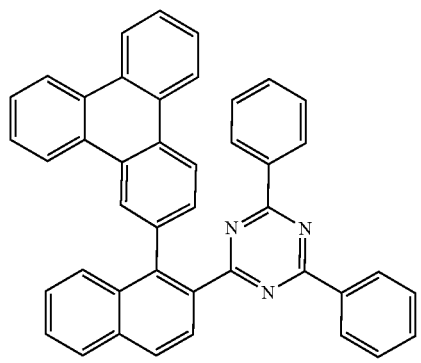
Compound 3-39
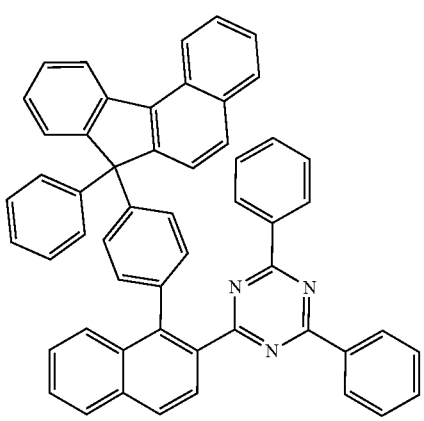
Compound 3-40
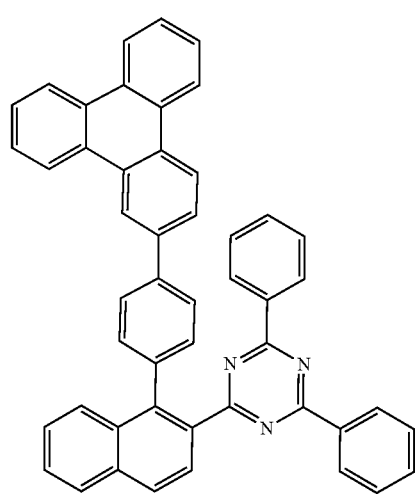

Compound 3-41
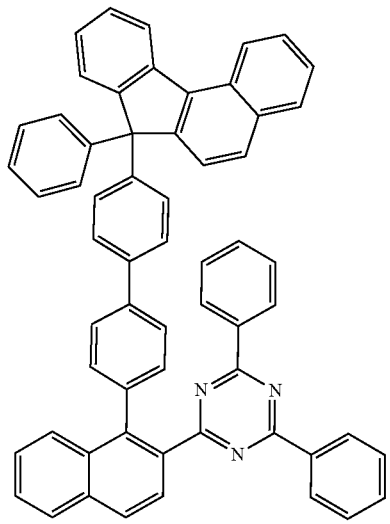
Compound 3-42
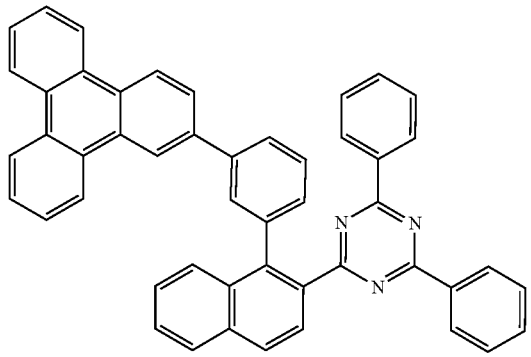
Compound 3-43
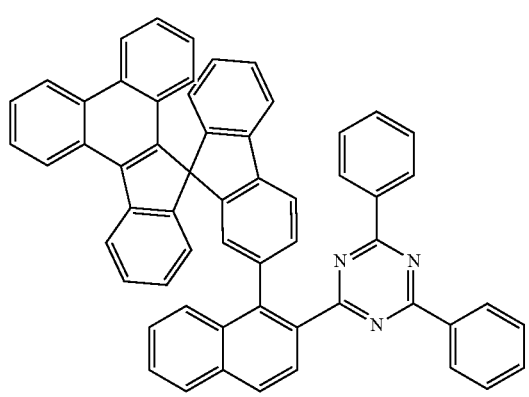
Compound 3-44
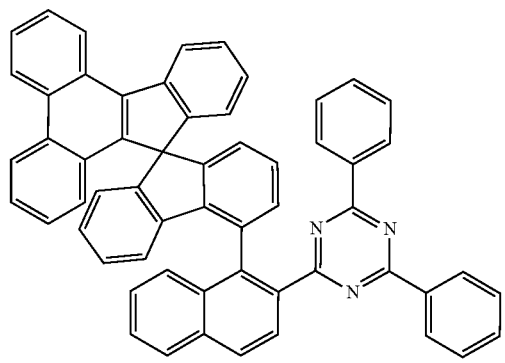
Compound 3-45
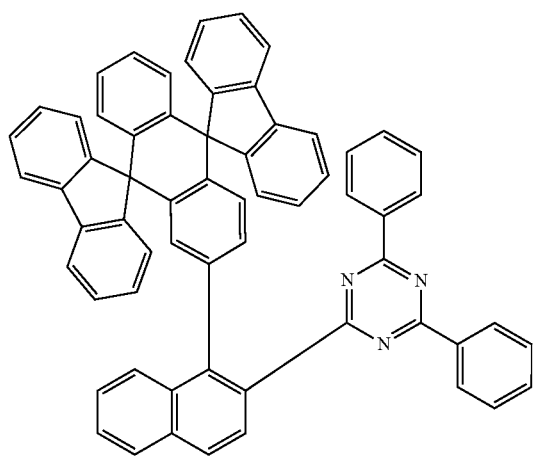
Compound 3-46
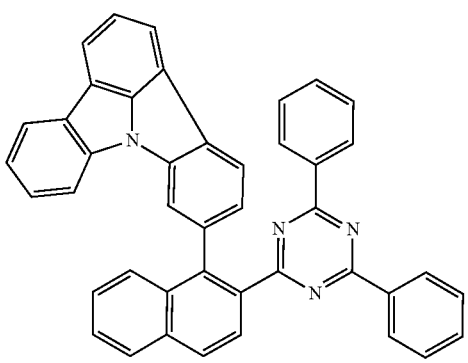

Compound 3-47
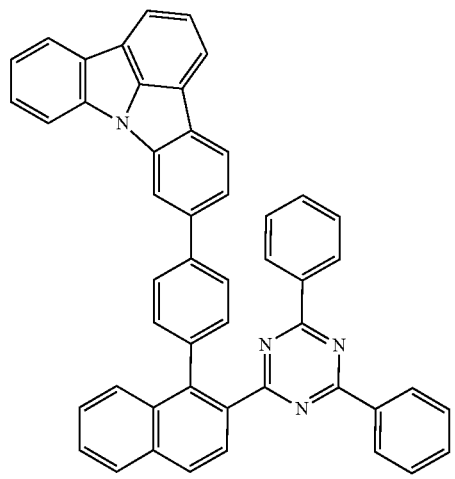
Compound 3-48
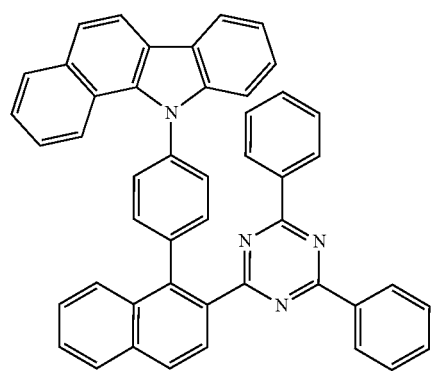
Compound 3-49
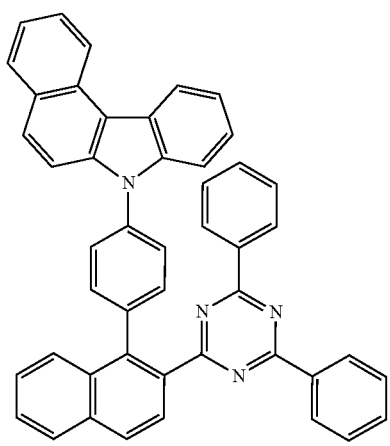
Compound 3-50
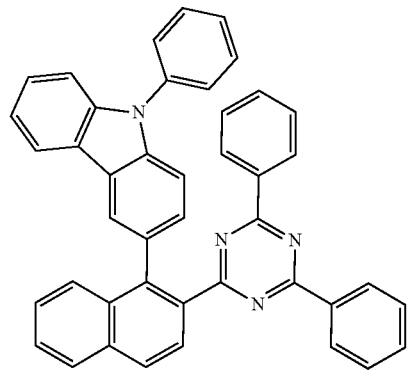
Compound 4-1
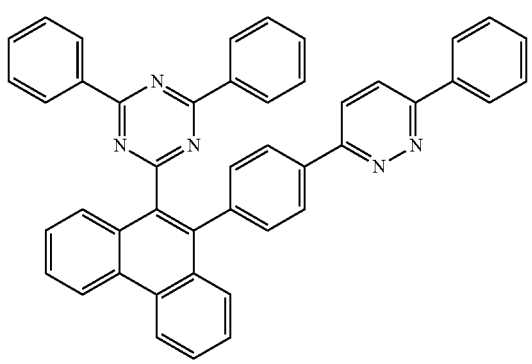
Compound 4-2
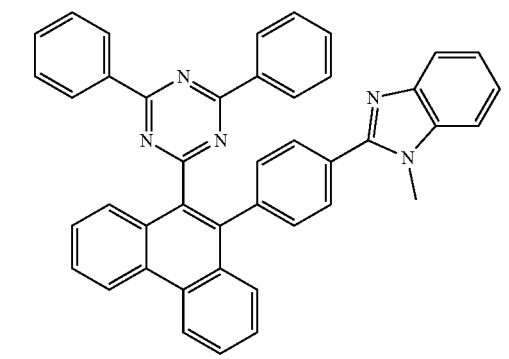
Compound 4-3
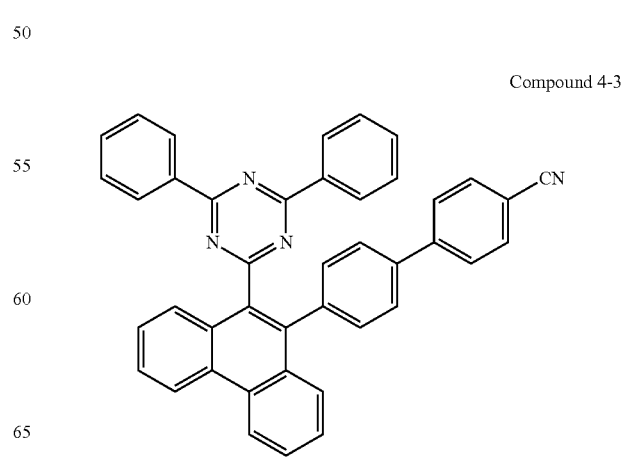

Compound 4-4
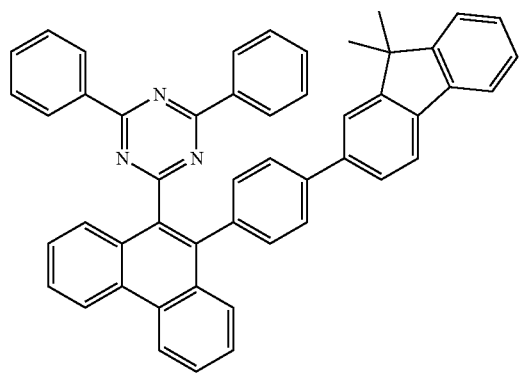
Compound 4-5
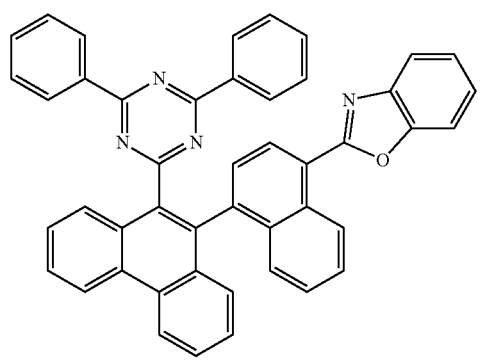
Compound 4-6
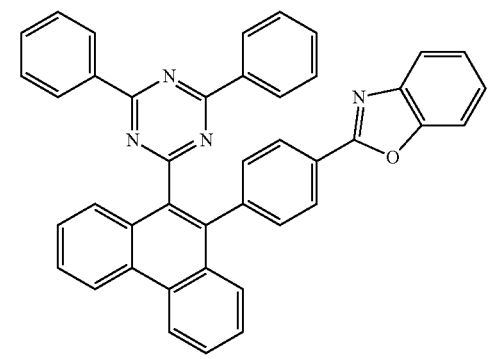
Compound 4-7
Compound 4-8
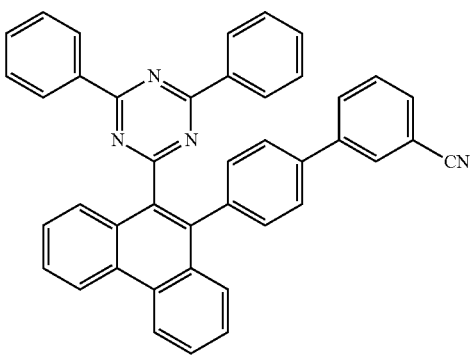
Compound 4-9
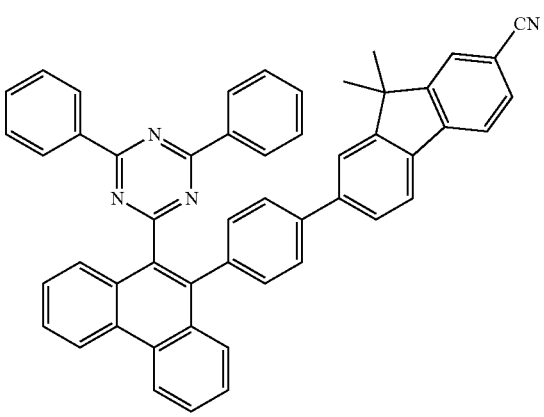
Compound 4-10
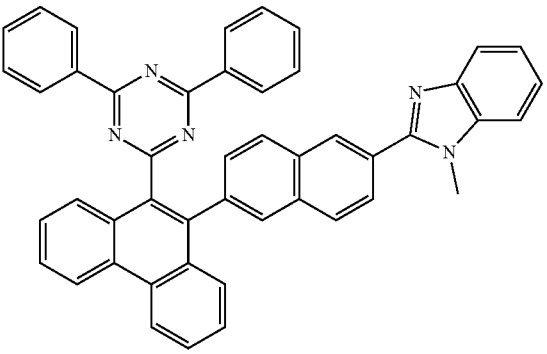
Compound 4-11
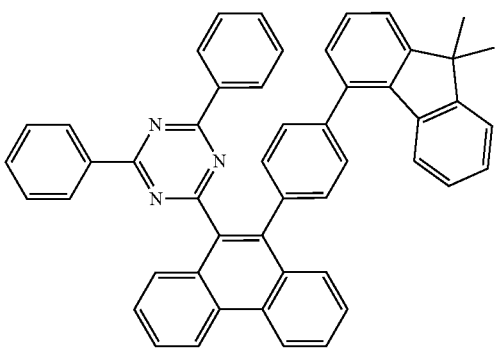

Compound 4-12
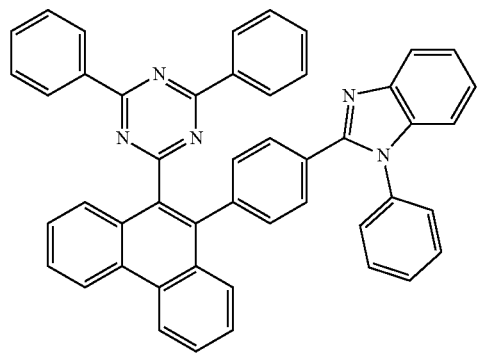
Compound 4-13
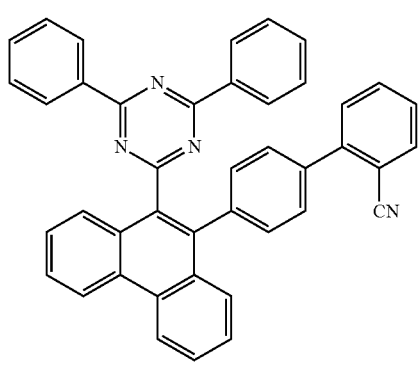
Compound 4-14
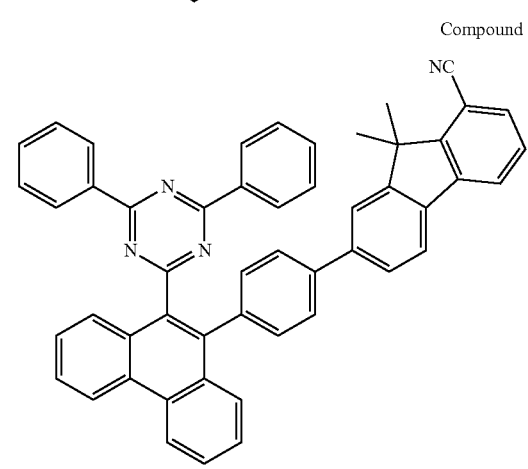
Compound 4-15
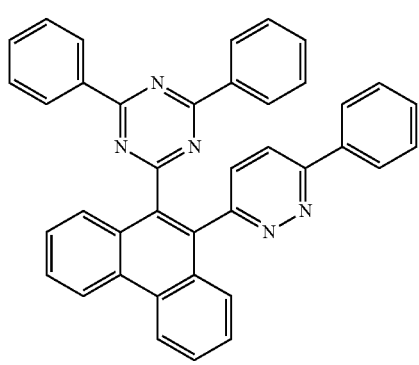
Compound 4-16
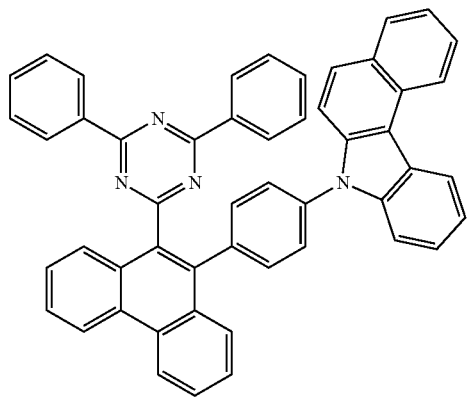
Compound 4-17
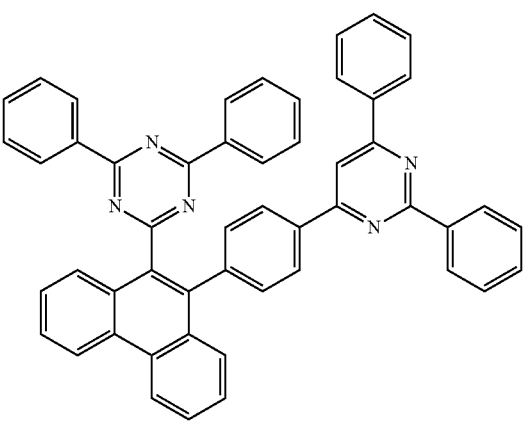
Compound 4-18
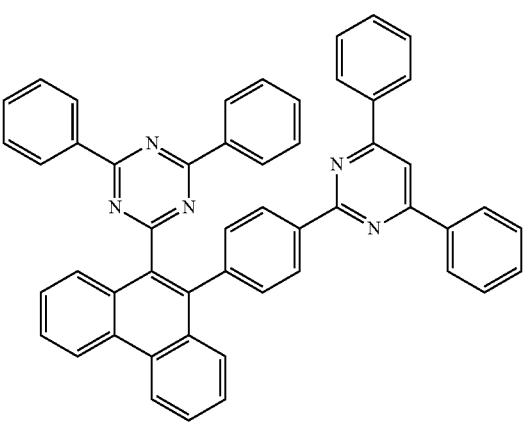

Compound 4-19
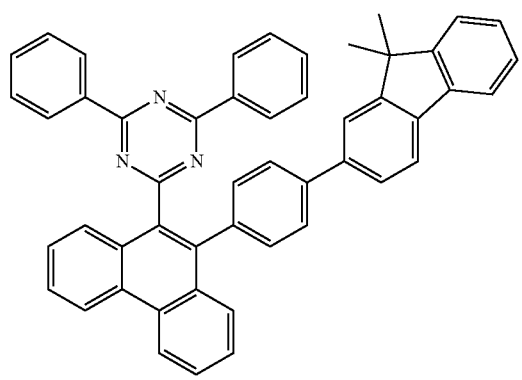
Compound 4-20
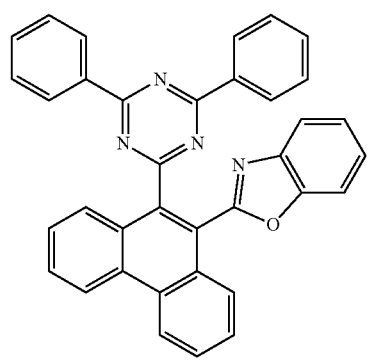
Compound 4-21
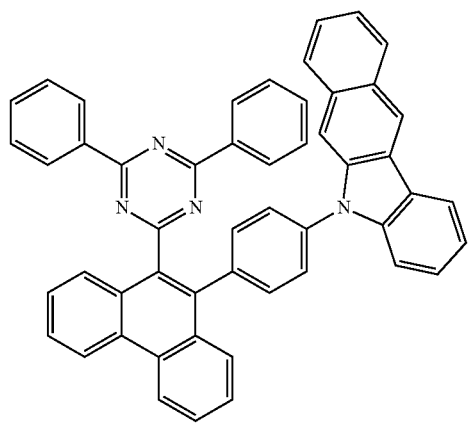
Compound 4-22
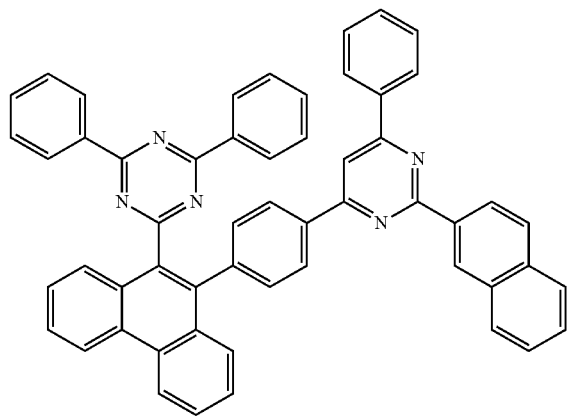
Compound 4-23
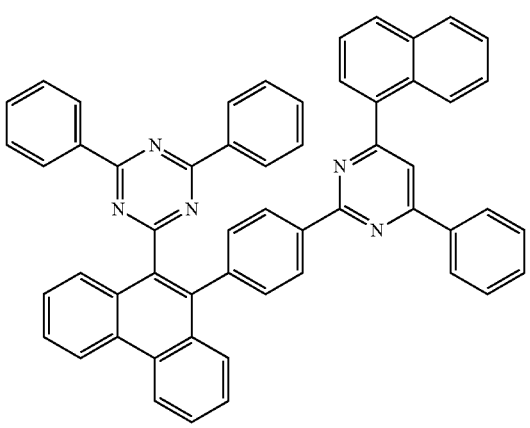
Compound 4-24
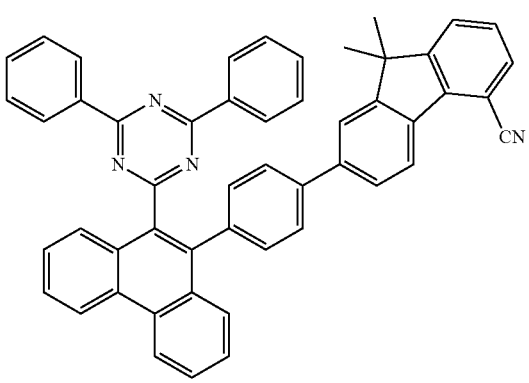
Compound 4-25
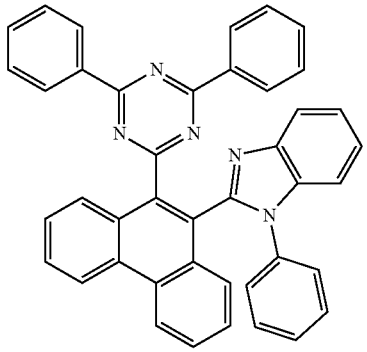
Compound 4-26
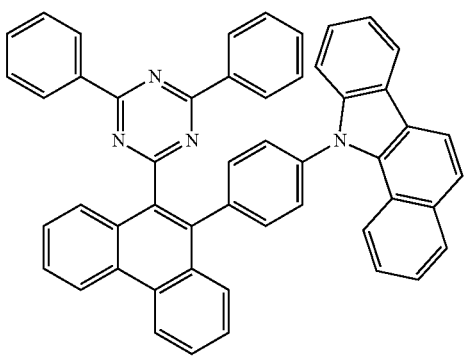

Compound 4-27
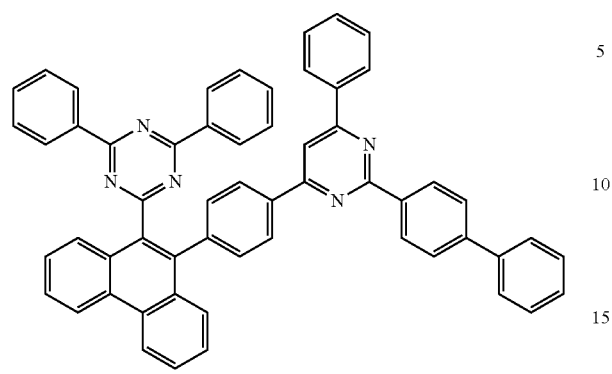
Compound 4-28
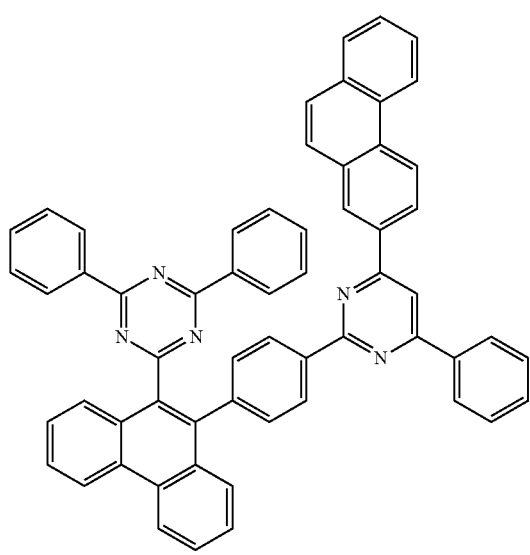
Compound 4-29
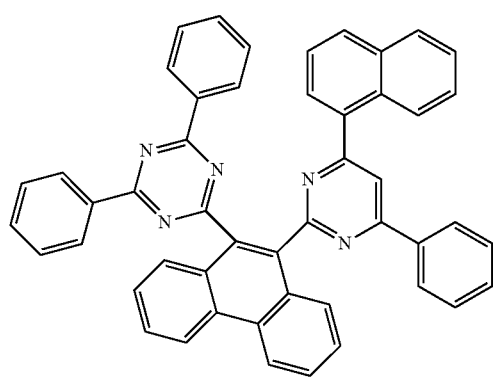
Compound 4-30
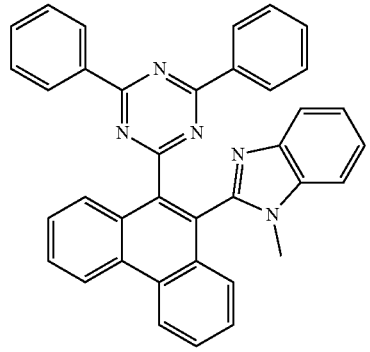
Compound 4-31
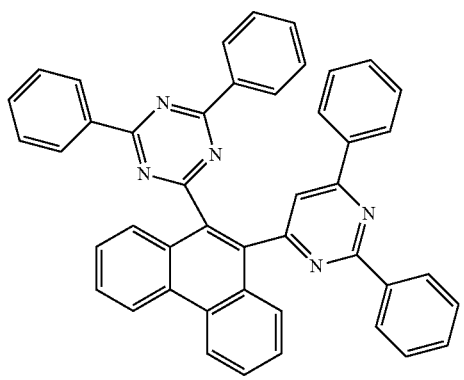
Compound 4-32
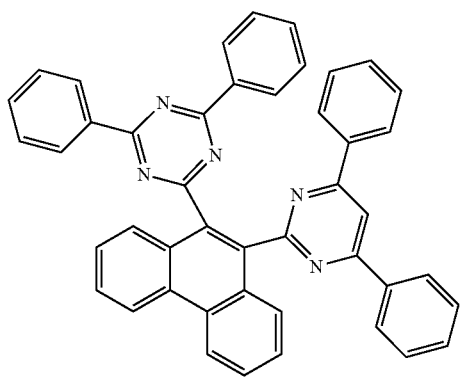
Compound 4-33
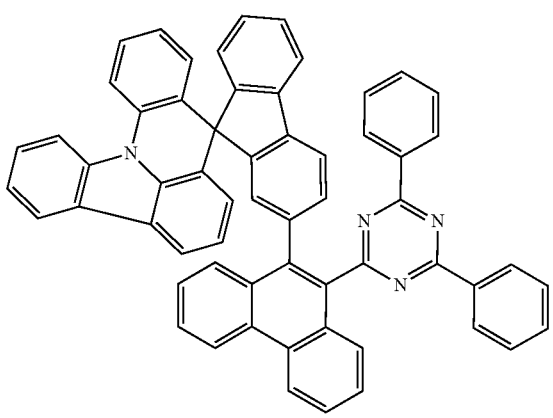

Compound 4-34
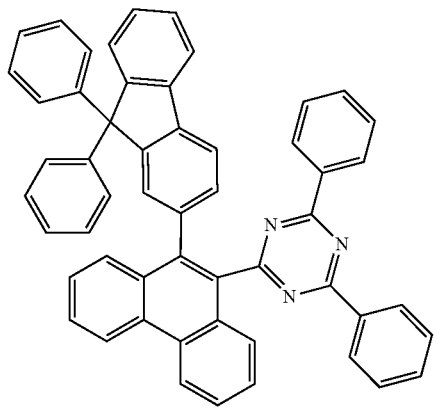
Compound 4-35
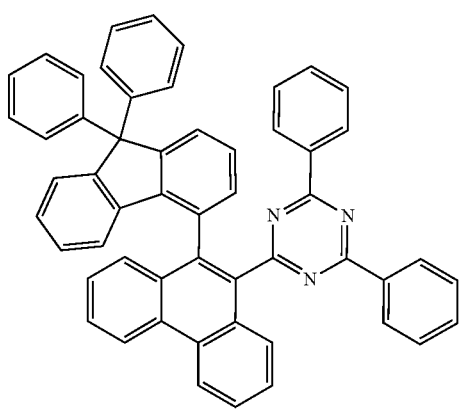
Compound 4-36
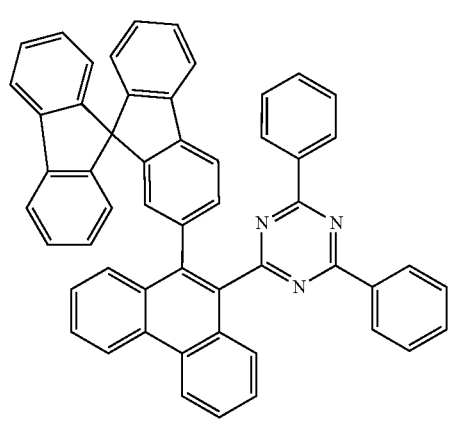
Compound 4-37
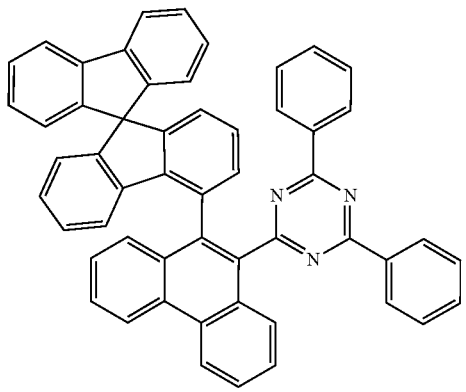
Compound 4-38
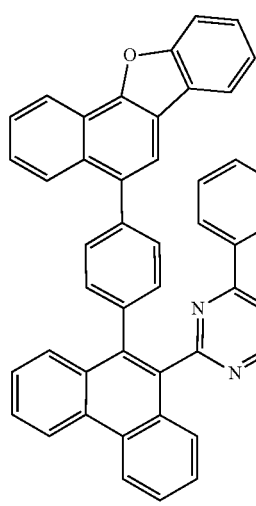
Compound 4-39
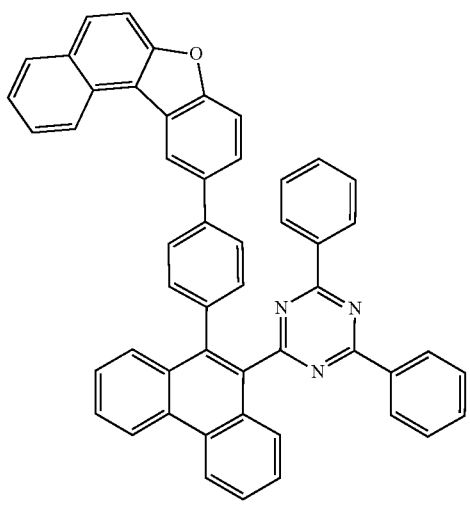

Compound 4-40
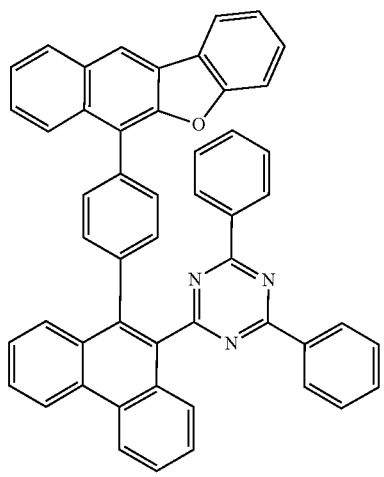
Compound 4-41
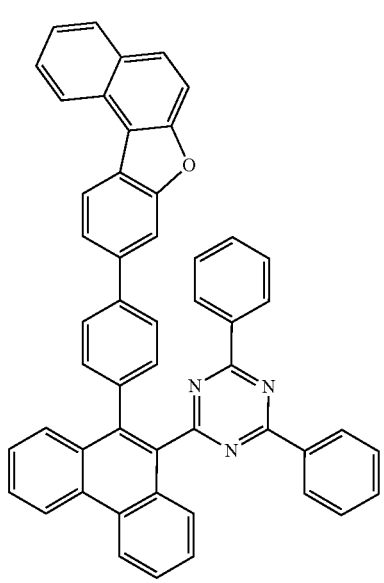
Compound 4-42
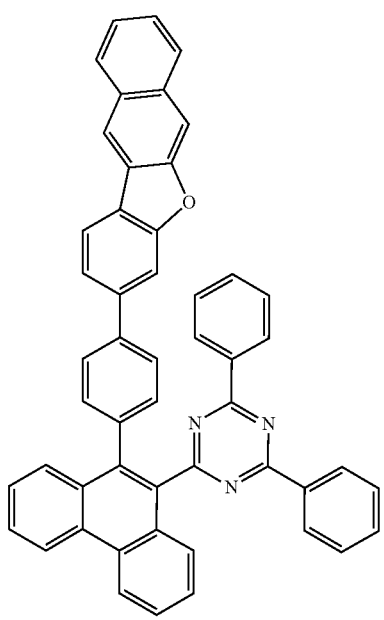
Compound 4-43
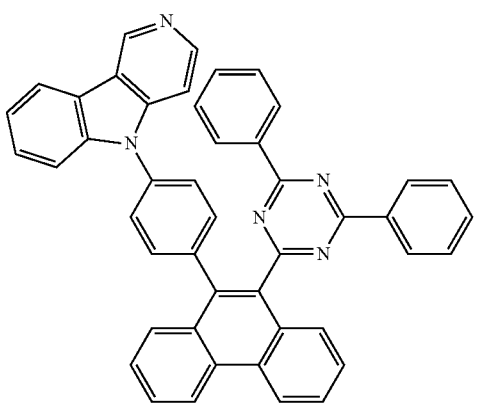
Compound 4-44
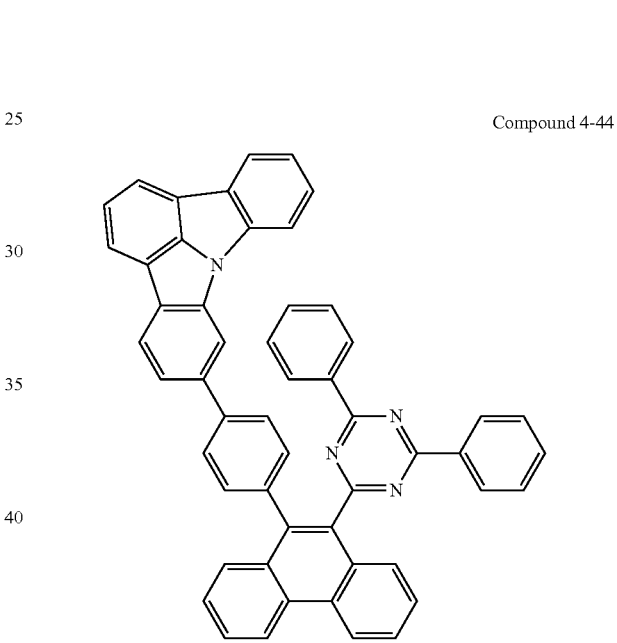
Compound 4-45
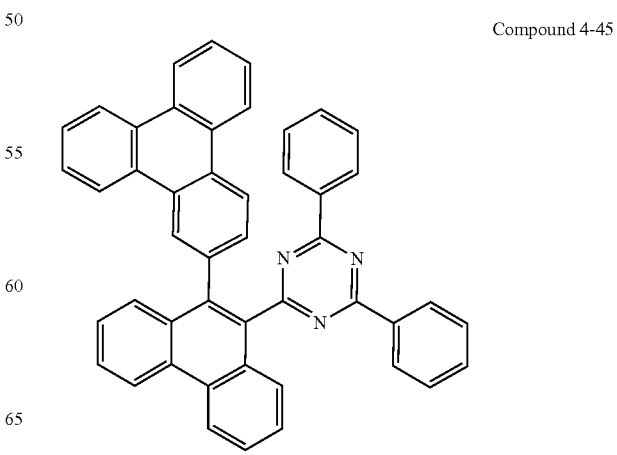

Compound 4-46
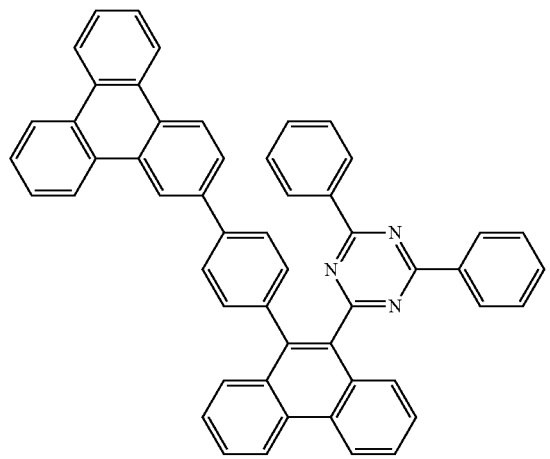
Compound 4-47
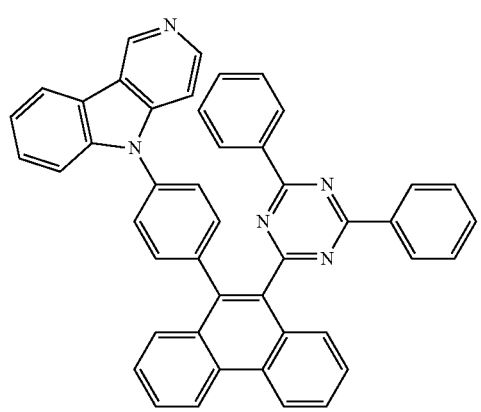
Compound 4-48
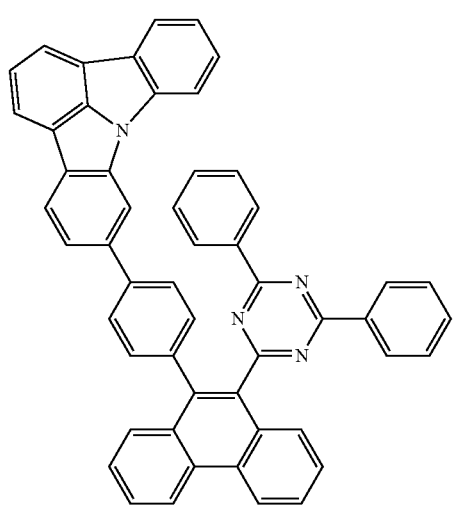
Compound 4-49
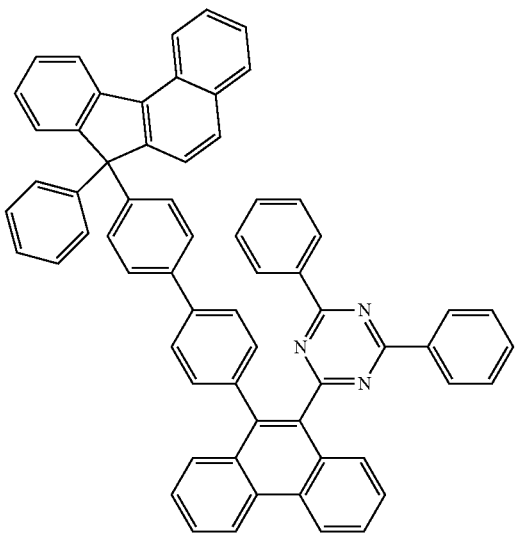
Compound 4-50
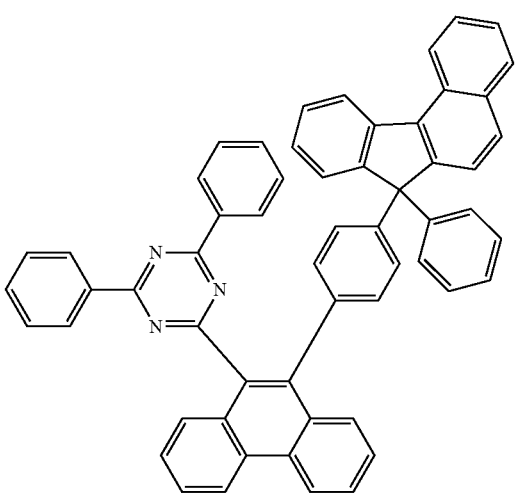
Compound 4-51
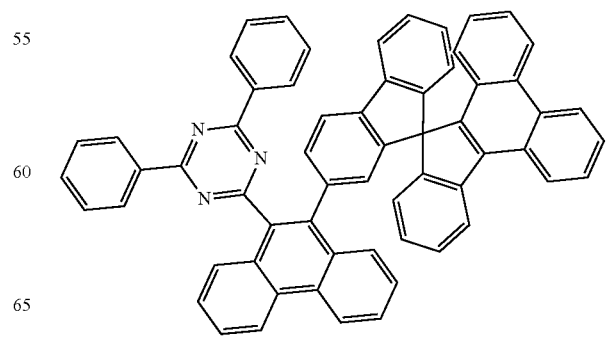

Compound 4-52
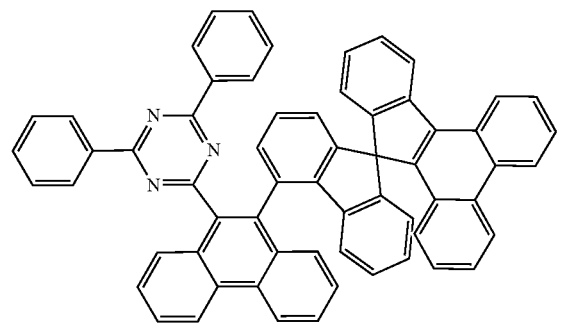
Compound 4-53
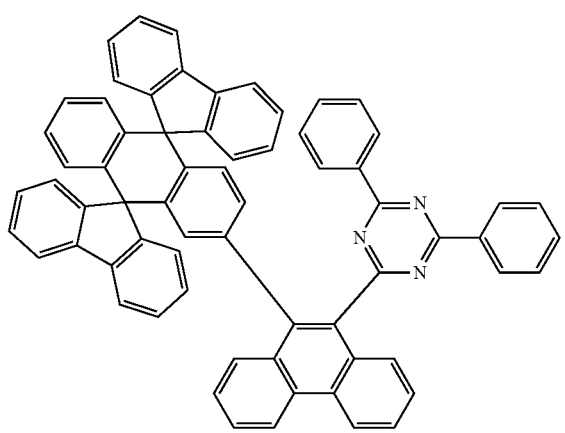
Compound 4-54
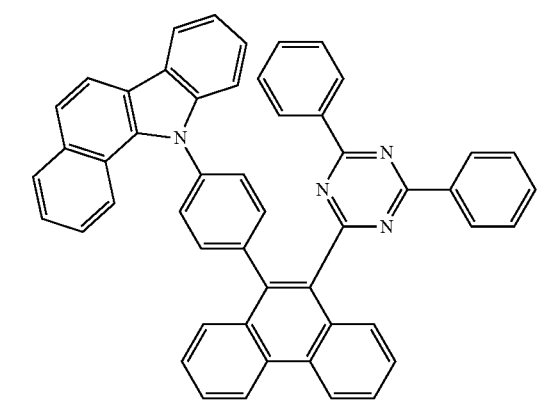
Compound 4-55
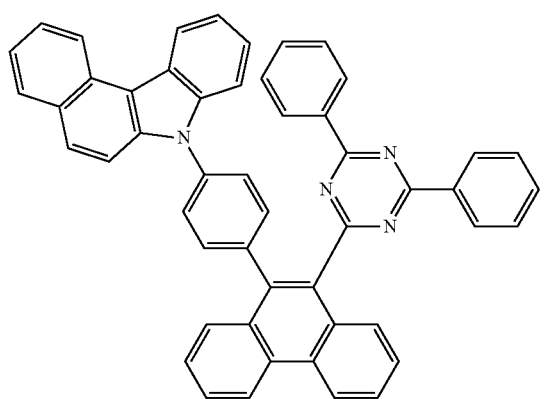
Compound 5-1
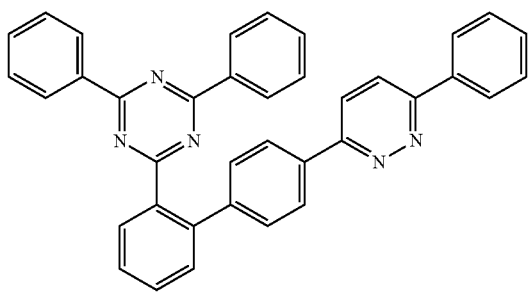
Compound 5-2
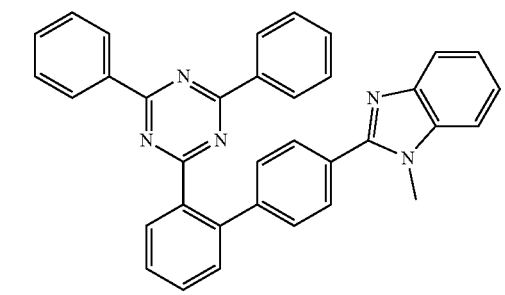
Compound 5-3
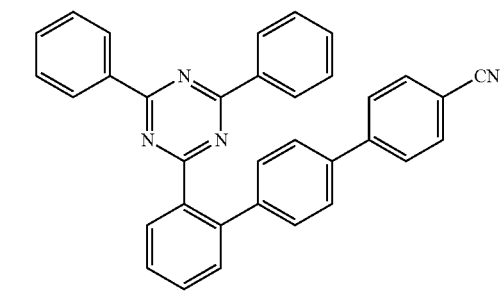
Compound 5-4
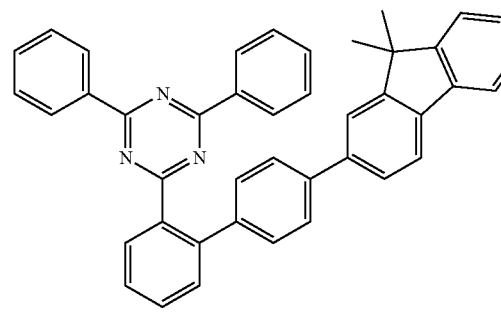
Compound 5-5
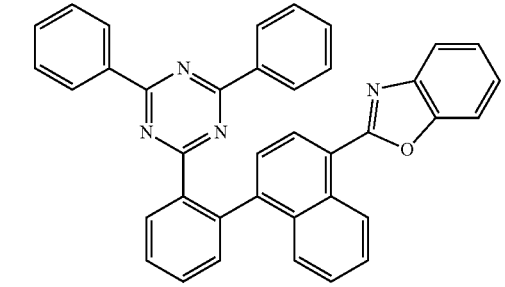

Compound 5-6
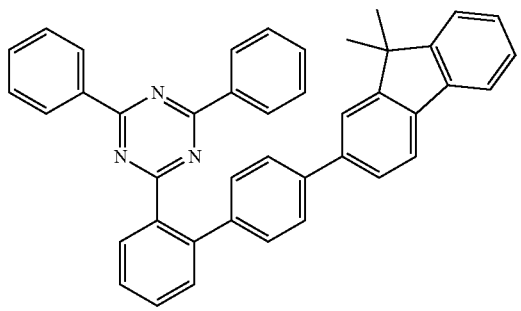
Compound 5-7
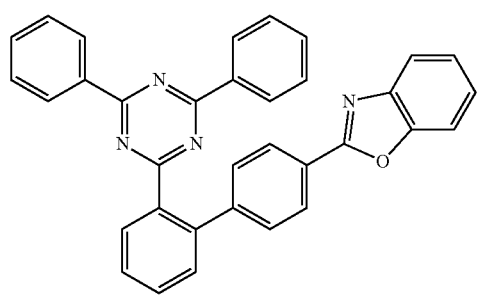
Compound 5-8
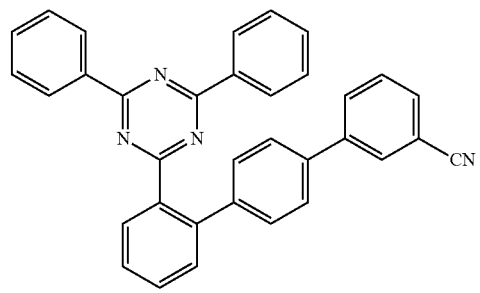
Compound 5-9
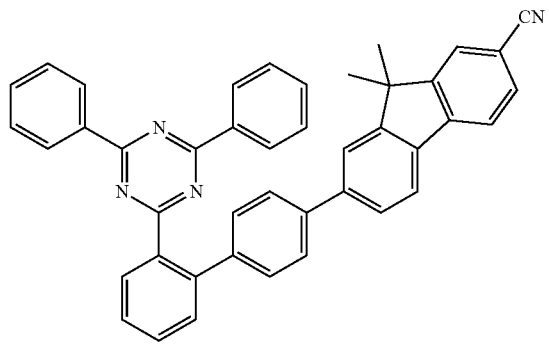
Compound 5-10
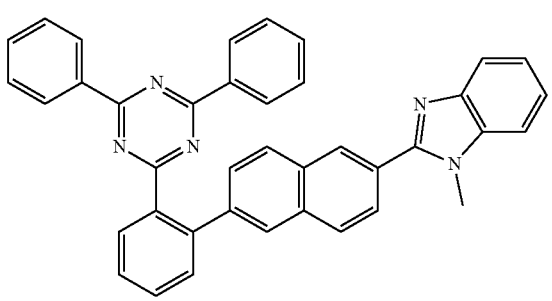
Compound 5-11
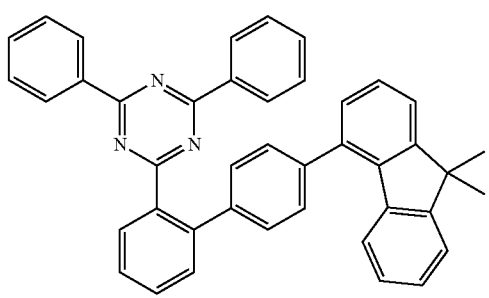
Compound 5-12
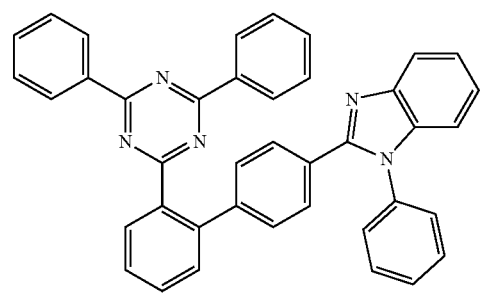
Compound 5-13
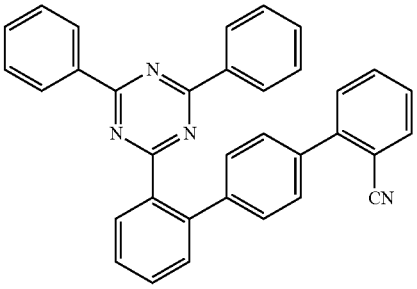
Compound 5-14
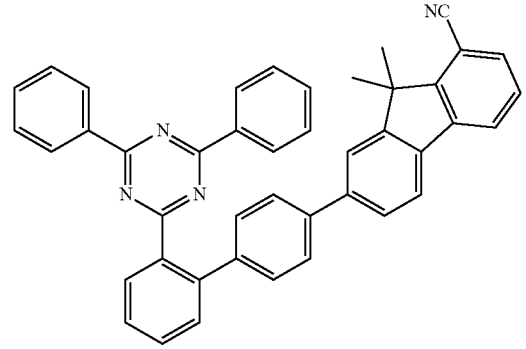
Compound 5-15
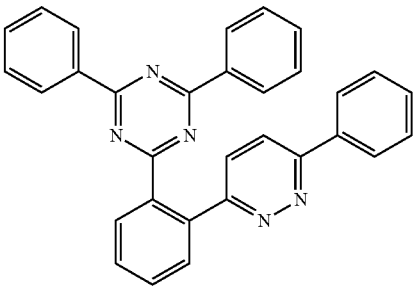

-continued
Compound 5-16
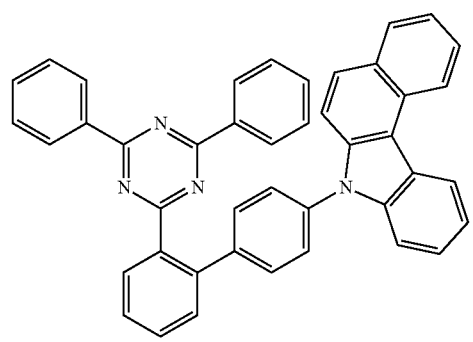
Compound 5-17
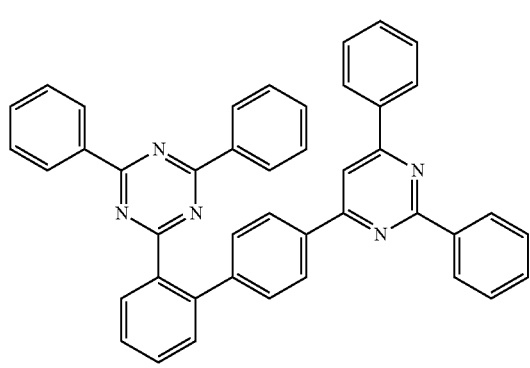
Compound 5-18
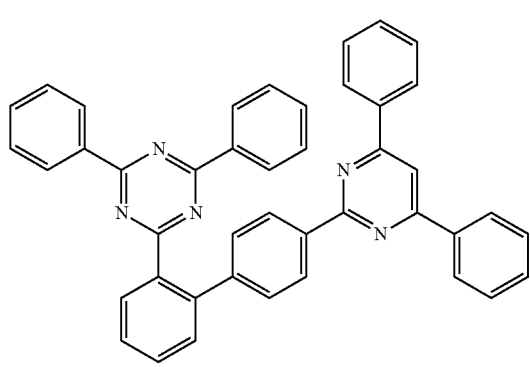
Compound 5-19
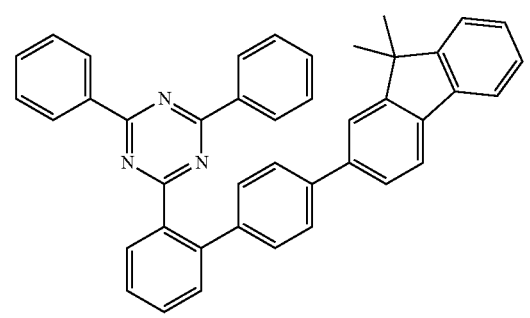
Compound 5-20
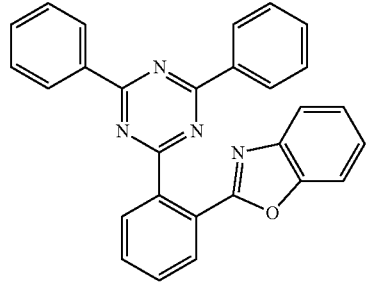
Compound 5-21
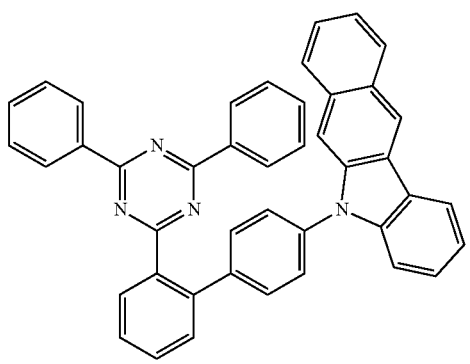
Compound 5-22
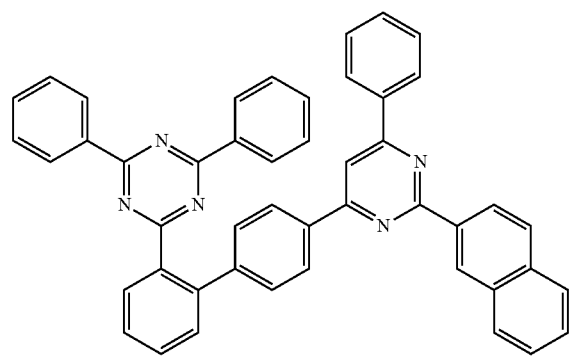
Compound 5-23
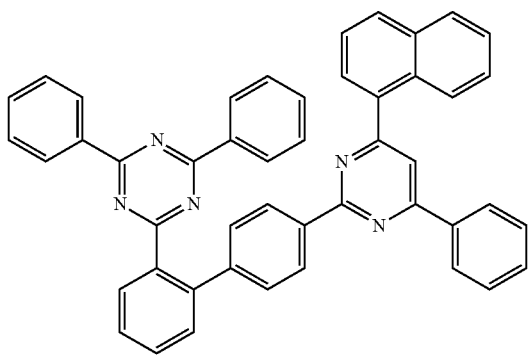

Compound 5-24
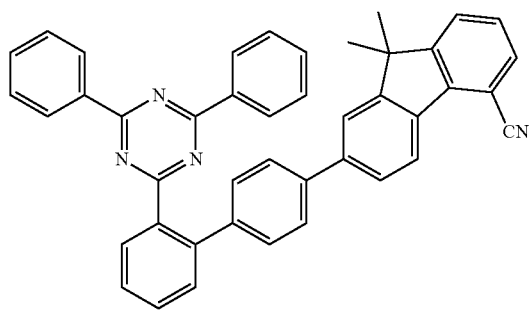
Compound 5-25
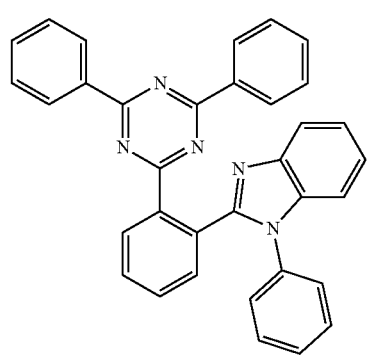
Compound 5-27
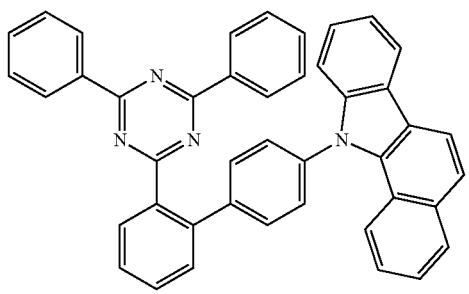
Compound 5-28
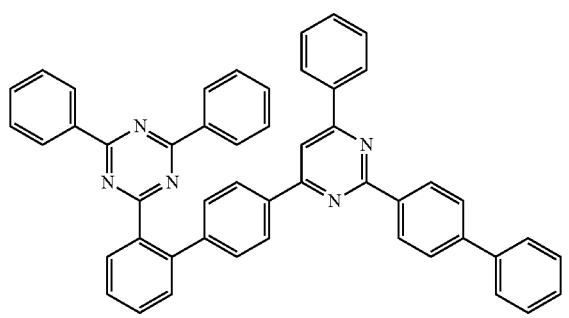
Compound 5-29
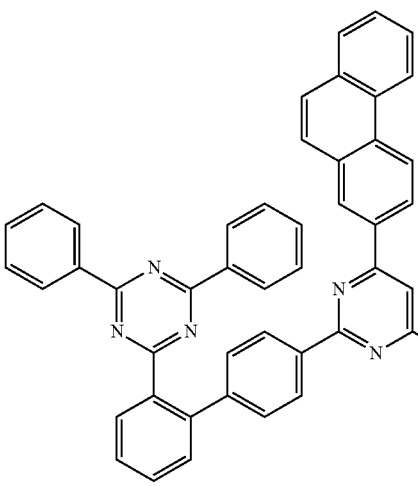
Compound 5-30
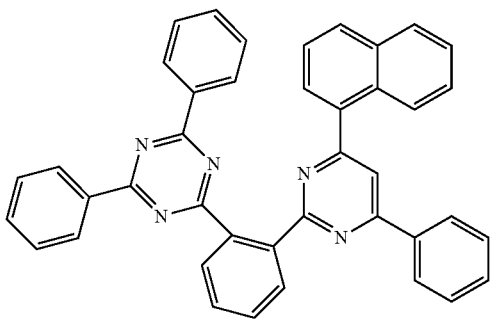
Compound 5-31
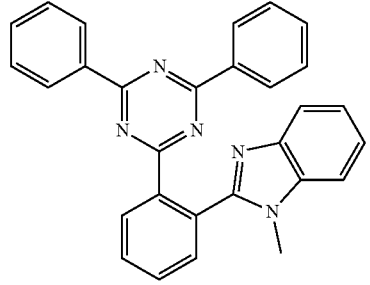
Compound 5-32
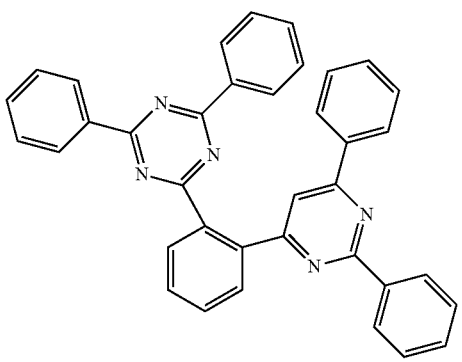

Compound 5-33
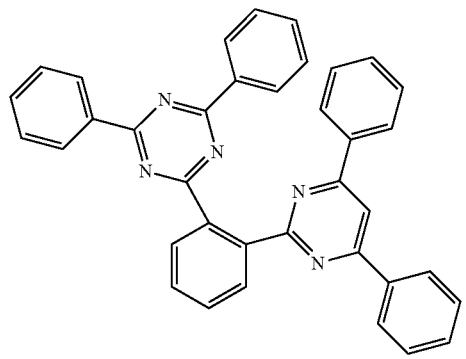
Compound 5-34
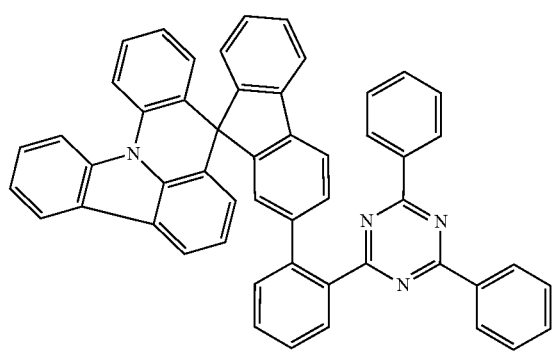
Compound 5-35
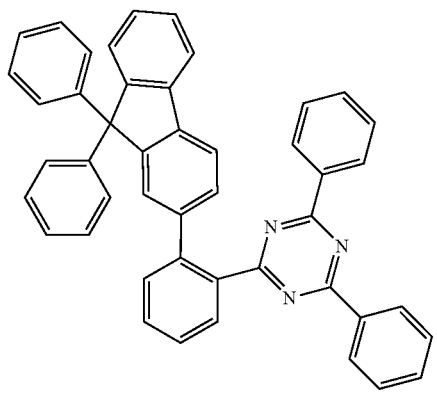
Compound 5-36
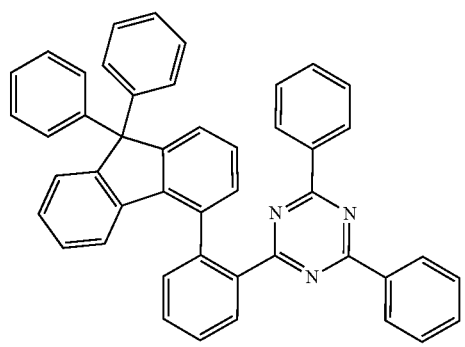
Compound 5-37
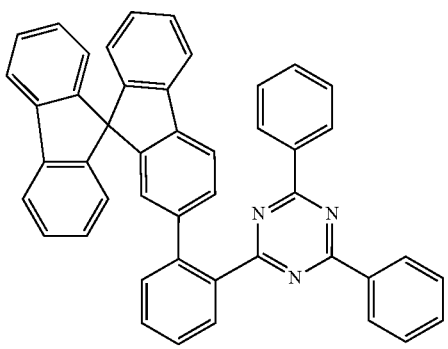
Compound 5-38
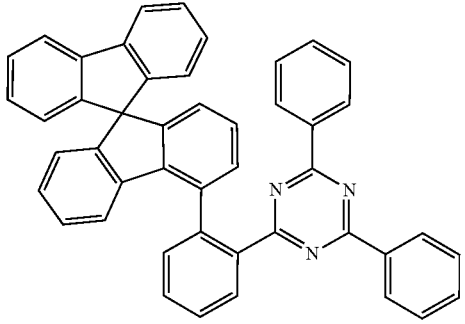
Compound 5-39
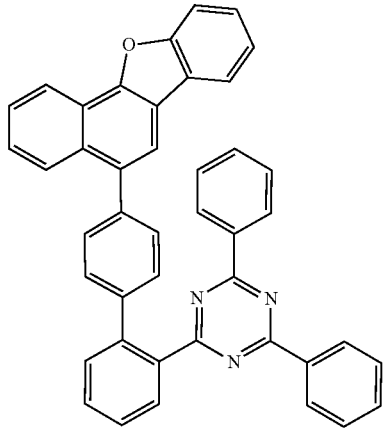
Compound 5-40
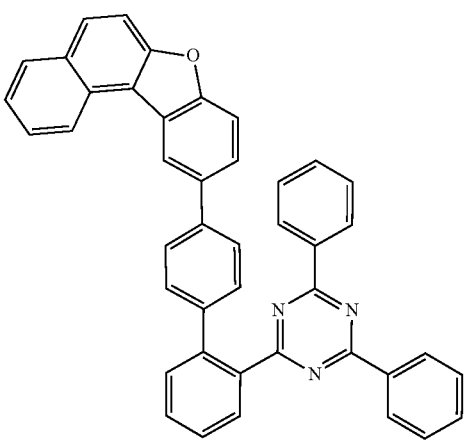

Compound 5-41
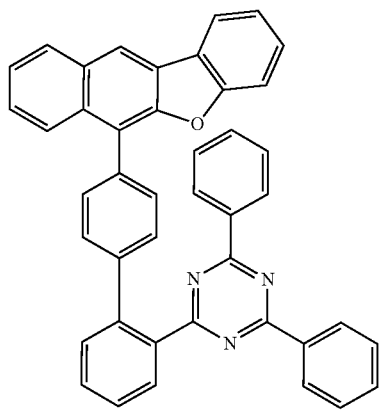
Compound 5-42
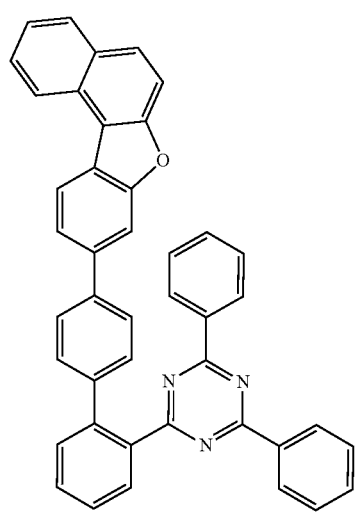
Compound 5-43
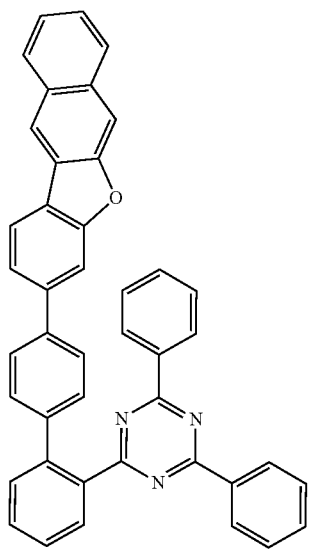
Compound 5-44
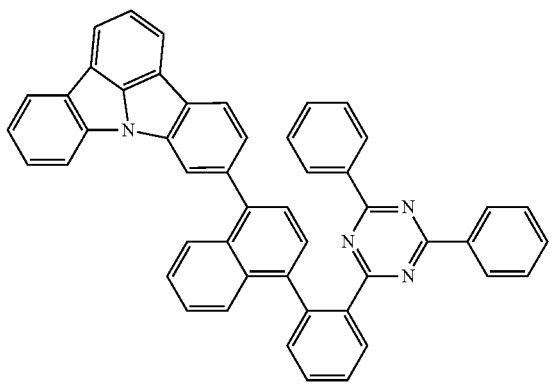
Compound 5-45
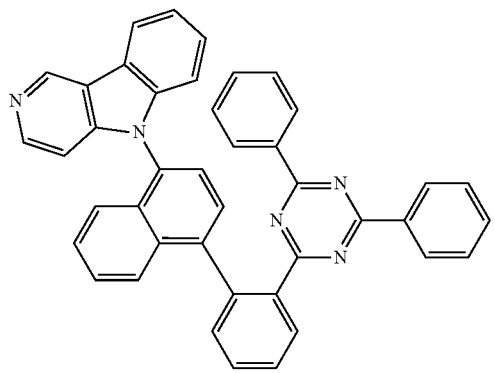
Compound 5-46
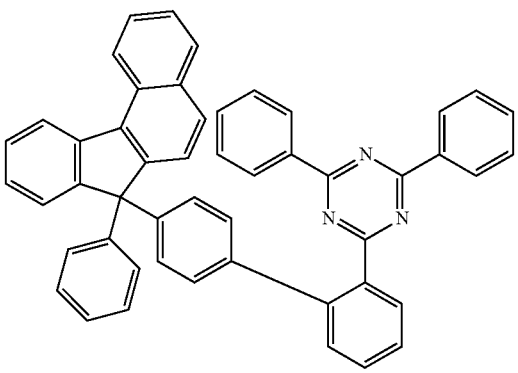
Compoun 5-47
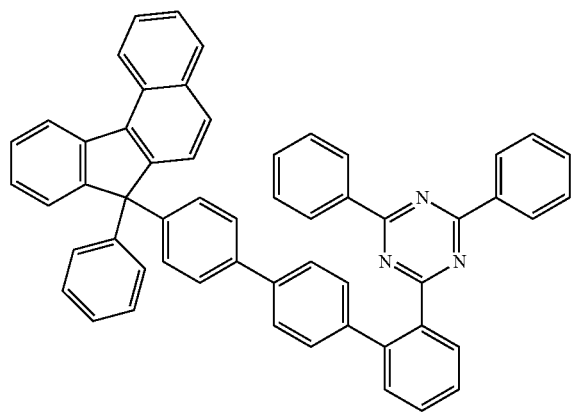

Compound 5-48

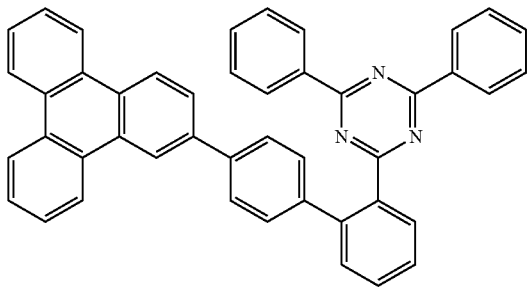

Compound 5-52

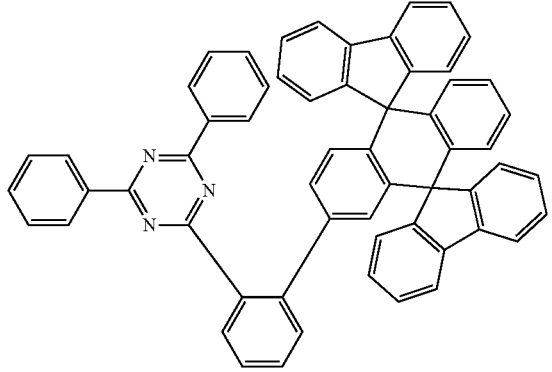

Compound 5-49

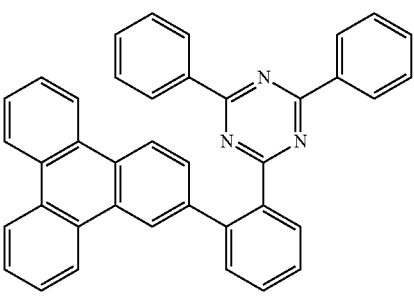

Compound 5-50

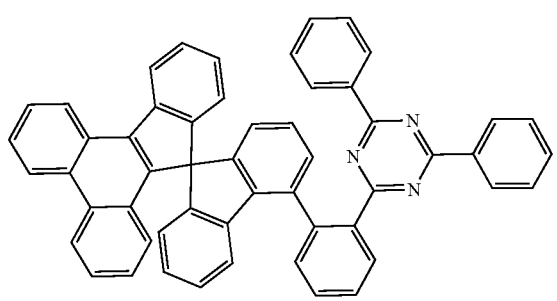

Compound 5-51

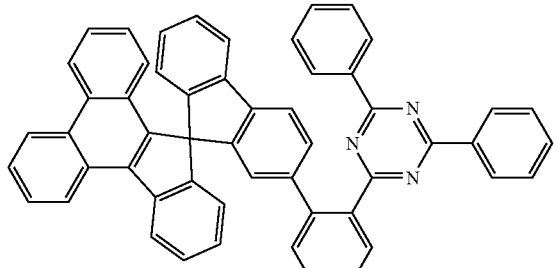

For example, in the compound of Formula 1, a core structure may be prepared as in the following General Formula 1. The substituent may be bonded by a method known in the art, and the kind and position of the substituent or the number of substituents may be changed according to the technology known in the art.

[General Formula 1]

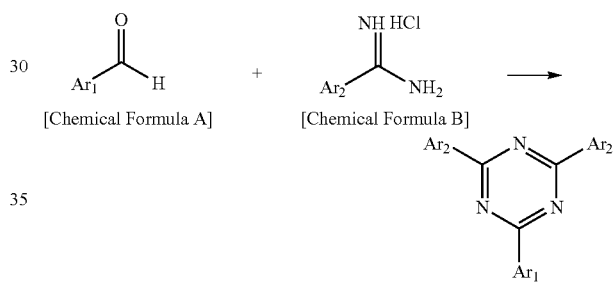

[Chemical Formula A]  [Chemical Formula B]  [Chemical Formula 1-A]

In General Formula 1, a core structure of Chemical Formula 1-A may be prepared through a coupling reaction using a base from a compound having an aldehyde structure, which is represented by Chemical Formula A and a compound having an amidine structure, which is represented by Chemical Formula B.

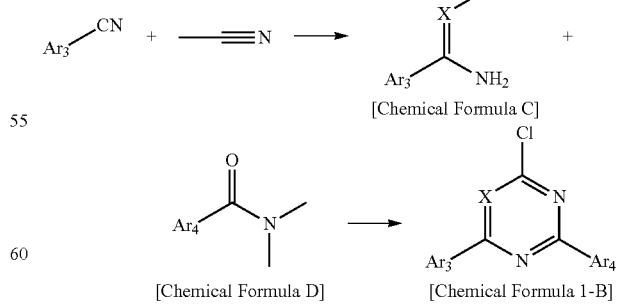

[Chemical Formula C]

[Chemical Formula D]  [Chemical Formula 1-B]

Alternatively, a structure of Chemical Formula C may be obtained through a coupling reaction using an aryl cyanide compound and a base of acetonitrile, as a medium, and a core structure of Chemical Formula 1-B may be prepared through a reflux reaction of the structures of Chemical Formulae C and D and $POCl_3$.

General Formula 1 only describes an example of the method of synthesizing the core of Chemical Formula 1, and the method is not limited thereto, and the kind and position of substituent may be changed, if necessary. The specific preparation method will be described below.

Further, the present specification provides an organic light emitting device including the above-described compound.

An exemplary embodiment of the present application provides an organic light emitting device including: a first electrode; a second electrode provided to face the first electrode; and one or more organic material layers provided between the first electrode and the second electrode, in which one or more layers of the organic material layers include the compound.

When one member is disposed "on" another member in the present specification, this includes not only a case where the one member is brought into contact with another member, but also a case where still another member is present between the two members.

When one part "includes" one constituent element in the present specification, unless otherwise specifically described, this does not mean that another constituent element is excluded, but means that another constituent element may be further included.

The organic material layer of the organic light emitting device of the present application may also be composed of a single-layered structure, but may be composed of a multi-layered structure in which two or more organic material layers are stacked. For example, as a representative example of the organic light emitting device of the present invention, an organic light emitting device may have a structure including a hole injection layer, a hole transport layer, a light emitting layer, an electron transport layer, an electron injection layer, and the like as organic material layers. However, the structure of the organic light emitting device is not limited thereto, and may include a fewer number of organic material layers.

In an exemplary embodiment of the present application, the organic material layer includes a light emitting layer, and the light emitting layer includes the compound.

In an exemplary embodiment of the present application, the organic material layer includes a hole injection layer or a hole transport layer, and the hole injection layer or the hole transport layer includes the compound.

In another exemplary embodiment, the organic material layer includes a light emitting layer, and the light emitting layer includes the compound.

In an exemplary embodiment of the present application, the organic material layer includes an electron transport layer or an electron injection layer, and the electron transport layer or the electron injection layer includes the compound.

In an exemplary embodiment of the present application, the organic material layer includes an electron blocking layer or a hole blocking layer, and the electron blocking layer or the hole blocking layer includes the compound.

In an exemplary embodiment of the present application, the organic material layer is an electron transport layer, and the organic light emitting device further includes one or two or more layers selected from the group consisting of a hole injection layer, a hole transport layer, a light emitting layer, an electron injection layer, an electron blocking layer, and a hole blocking layer.

In an exemplary embodiment of the present application, the organic light emitting device includes: a first electrode; a second electrode provided to face the first electrode; a light emitting layer provided between the first electrode and the second electrode; and two or more organic material layers provided between the light emitting layer and the first electrode, or between the light emitting layer and the second electrode, in which at least one of the two or more organic material layers includes the compound. In an exemplary embodiment of the present application, as the two or more organic material layers, two or more may be selected from the group consisting of an electron transport layer, an electron injection layer, a layer which transports and injects electrons simultaneously, and a hole blocking layer.

In an exemplary embodiment of the present application, the organic material layer includes two or more electron transport layers, and at least one of the two or more electron transport layers includes the compound. Specifically, in an exemplary embodiment of the present specification, the compound may also be included in one layer of the two or more electron transport layers, and may be included in each of the two or more electron transport layers.

In addition, in an exemplary embodiment of the present application, when the compound is included in each of the two or more electron transport layers, the other materials except for the compound may be the same as or different from each other.

In an exemplary embodiment of the present application, the organic material layer further includes a hole injection layer or a hole transport layer, which includes a compound including an arylamino group, a carbazolyl group, or a benzocarbazolyl group, in addition to the organic material layer including the compound.

In another exemplary embodiment, the organic light emitting device may be an organic light emitting device having a structure (normal type) in which a positive electrode, one or more organic material layers, and a negative electrode are sequentially stacked on a substrate.

In still another exemplary embodiment, the organic light emitting device may be an organic light emitting device having a reverse-direction structure (inverted type) in which a negative electrode, one or more organic material layers, and a positive electrode are sequentially stacked on a substrate.

For example, the structure of the organic light emitting device according to an exemplary embodiment of the present application is exemplified in FIGS. 1 and 2.

FIG. 1 exemplifies a structure of an organic light emitting device in which a substrate 1, a positive electrode 2, a light emitting layer 3, and a negative electrode 4 are sequentially stacked. In the structure as described above, the compound may be included in the light emitting layer 3.

FIG. 2 exemplifies a structure of an organic light emitting device in which a substrate 1, a positive electrode 2, a hole injection layer 5, a hole transport layer 6, a light emitting layer 3, an electron transport layer 7, and a negative electrode 4 are sequentially stacked. In the structure as described above, the compound may be included in one or more layers of the hole injection layer 5, the hole transport layer 6, the light emitting layer 3, and the electron transport layer 7.

In the structure as described above, the compound may be included in one or more of the hole injection layer, the hole transport layer, the light emitting layer, and the electron transport layer.

The organic light emitting device of the present application may be manufactured by the materials and methods known in the art, except that one or more layers of the organic material layers include the compound of the present application, that is, the compound.

When the organic light emitting device includes a plurality of organic material layers, the organic material layers may be formed of the same material or different materials.

The organic light emitting device of the present application may be manufactured by the materials and methods known in the art, except that one or more layers of the organic material layers include the compound, that is, the compound represented by Chemical Formula 1.

For example, the organic light emitting device of the present application may be manufactured by sequentially stacking a first electrode, an organic material layer, and a second electrode on a substrate. In this case, the organic light emitting device may be manufactured by depositing a metal or a metal oxide having conductivity, or an alloy thereof on a substrate to form a positive electrode, forming an organic material layer including a hole injection layer, a hole transport layer, a light emitting layer, and an electron transport layer thereon, and then depositing a material, which may be used as a negative electrode, thereon, by using a physical vapor deposition (PVD) method such as sputtering or e-beam evaporation. In addition to the method as described above, an organic light emitting device may be made by sequentially depositing a negative electrode material, an organic material layer, and a positive electrode material on a substrate.

Further, the compound of Chemical Formula 1 may be formed as an organic material layer by not only a vacuum deposition method, but also a solution application method when an organic light emitting device is manufactured. Here, the solution application method means spin coating, dip coating, doctor blading, inkjet printing, screen printing, a spray method, roll coating, and the like, but is not limited thereto.

In addition to the method as described above, an organic light emitting device may also be made by sequentially depositing a negative electrode material, an organic material layer, and a positive electrode material on a substrate (International Publication No. 2003/012890). However, the manufacturing method is not limited thereto.

In an exemplary embodiment of the present application, the first electrode is a positive electrode, and the second electrode is a negative electrode.

In another exemplary embodiment, the first electrode is a negative electrode, and the second electrode is a positive electrode.

As the positive electrode material, a material having a large work function is usually preferred so as to smoothly inject holes into an organic material layer. Specific examples of the positive electrode material which may be used in the present invention include: a metal, such as vanadium, chromium, copper, zinc, and gold, or alloys thereof; a metal oxide, such as zinc oxide, indium oxide, indium tin oxide (ITO), and indium zinc oxide (IZO); a combination of metal and oxide, such as ZnO:Al or $SnO_2$:Sb; an electrically conductive polymer, such as poly(3-methylthiophene), poly[3,4-(ethylene-1,2-dioxy)thiophene](PEDOT), polypyrrole, and polyaniline, and the like, but are not limited thereto.

As the negative electrode material, a material having a small work function is usually preferred so as to smoothly inject electrons into an organic material layer. Specific examples of the negative electrode material include: a metal, such as magnesium, calcium, sodium, potassium, titanium, indium, yttrium, lithium, gadolinium, aluminum, silver, tin, and lead, or alloys thereof; a multi-layered structural material, such as LiF/Al or $LiO_2$/Al, and the like, but are not limited thereto.

The hole injection layer is a layer which injects holes from an electrode, and a hole injection material is preferably a compound which has a capability of transporting holes and thus has an effect of injecting holes at a positive electrode and an excellent effect of injecting holes for a light emitting layer or a light emitting material, prevents excitons produced from the light emitting layer from moving to an electron injection layer or an electron injection material, and is also excellent in the ability to form a thin film. It is preferred that the highest occupied molecular orbital (HOMO) of the hole injection material is between the work function of the positive electrode material and the HOMO of a peripheral organic material layer. Specific examples of the hole injection material include metal porphyrin, oligothiophene, an arylamine-based organic material, a hexanitrile hexaazatriphenylene-based organic material, a quinacridone-based organic material, a perylene-based organic material, anthraquinone, a polyaniline and polythiophene-based electrically conductive polymer, and the like, but are not limited thereto.

The hole transport layer is a layer which receives holes from a hole injection layer and transports the holes to a light emitting layer, and a hole transport material is suitably a material which may receive holes transported from a positive electrode or a hole injection layer to transfer the holes to a light emitting layer, and has a large mobility for the holes. Specific examples thereof include an arylamine-based organic material, an electrically conductive polymer, a block copolymer in which a conjugate portion and a non-conjugate portion are present together, and the like, but are not limited thereto.

The light emitting material is preferably a material which may receive holes and electrons transported from a hole transport layer and an electron transport layer, respectively, and combine the holes and the electrons to emit light in a visible ray region, and has good quantum efficiency to fluorescence or phosphorescence. Specific examples thereof include: an 8-hydroxy-quinoline aluminum complex ($Alq_3$); a carbazole-based compound; a dimerized styryl compound; BAlq; a 10-hydroxybenzoquinoline-metal compound; a benzoxazole, benzthiazole and benzimidazole-based compound; a poly(p-phenylenevinylene) (PPV)-based polymer; a spiro compound; polyfluorene, lubrene, and the like, but are not limited thereto.

The light emitting layer may include a host material and a dopant material. Examples of the host material include a fused aromatic ring derivative, or a hetero ring-containing compound, and the like. Specific examples of the fused aromatic ring derivative include an anthracene derivative, a pyrene derivative, a naphthalene derivative, a pentacene derivative, a phenanthrene compound, a fluoranthene compound, and the like, and specific examples of the hetero ring-containing compound include a compound, a dibenzofuran derivative, a ladder-type furan compound, a pyrimidine derivative, and the like, but the examples are not limited thereto.

The electron transport layer is a layer which receives electrons from an electron injection layer and transports the electrons to a light emitting layer, and an electron transport material is suitably a material which may receive electrons well from a negative electrode and transfer the electrons to a light emitting layer, and has a large mobility for electrons.

Specific examples thereof include: an Al complex of 8-hydroxyquinoline; a complex including Alq$_3$; an organic radical compound; a hydroxyflavone-metal complex, and the like, but are not limited thereto. The electron transport layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and an electron injection material is preferably a compound which has a capability of transporting electrons, has an effect of injecting electrons from a negative electrode and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris(2-methyl-8-hydroxyquinolinato) aluminum, tris(8-hydroxyquinolinato) gallium, bis(10-hydroxybenzo[h]quinolinato) beryllium, bis(10-hydroxybenzo[h]quinolinato) zinc, bis(2-methyl-8-quinolinato) chlorogallium, bis(2-methyl-8-quinolinato)(o-cresolato) gallium, bis(2-methyl-8-quinolinato)(1-naphtholato) aluminum, bis(2-methyl-8-quinolinato)(2-naphtholato) gallium, and the like, but are not limited thereto.

The hole blocking layer is a layer which blocks holes from reaching a negative electrode, and may be generally formed under the same conditions as those of the hole injection layer. Specific examples thereof include an oxadiazole derivative or a triazole derivative, a phenanthroline derivative, BCP, an aluminum complex, and the like, but are not limited thereto.

The organic light emitting device according to the present specification may be a top emission type, a bottom emission type, or a dual emission type according to the material to be used.

MODE FOR INVENTION

Hereinafter, the present specification will be described in detail with reference to Examples for specifically describing the present specification. However, the Examples according to the present specification may be modified in various forms, and it is not interpreted that the scope of the present application is limited to the Examples described in detail below. The Examples of the present application are provided for more completely explaining the present specification to the person with ordinary skill in the art.

PREPARATION EXAMPLES

<Preparation Example 1> Synthesis of Compound 1-1

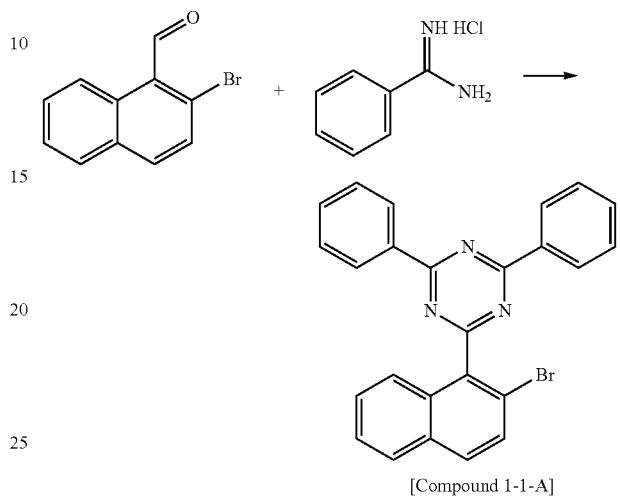

[Compound 1-1-A]

Under nitrogen flow, 2-bromo-1-naphthaldehyde (10 g, 42.54 mmol), benzimidamide hydrochloride (20 g, 127.6 mmol), and potassium phosphate (36 g, 170.2 mmol) were put into 150 mL of a dimethylacetamide (DMAc) solvent, and the resulting solution was heated and stirred for 18 hours. The reaction solution was cooled and then filtered, and then the filtered material was subjected to slurry purification using EtOH to obtain Compound 1-1-A (16 g, yield 86%).

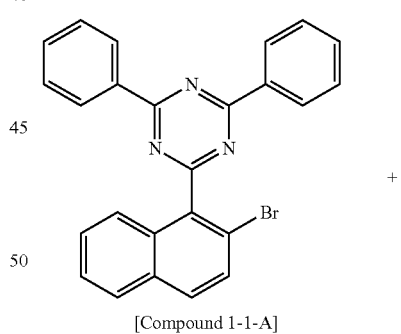

[Compound 1-1-A]

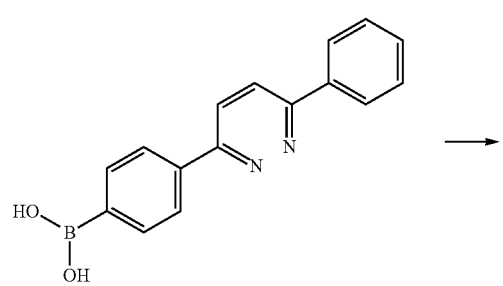

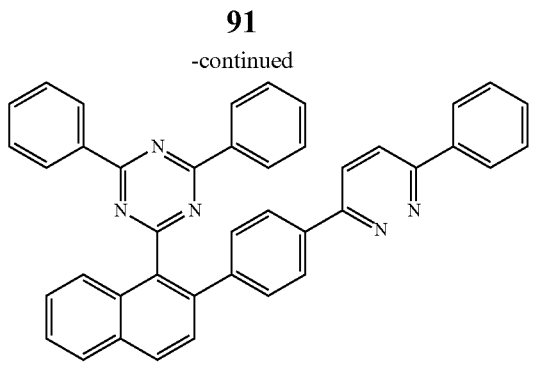

[Compound 1-1]

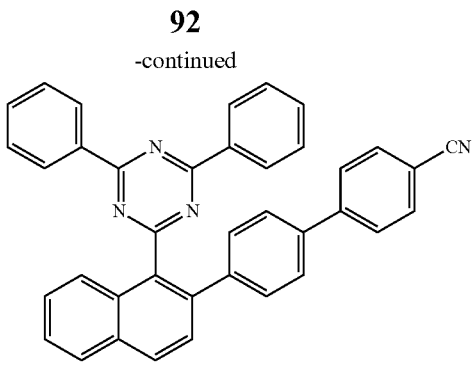

[Compound 1-3]

Under nitrogen flow, Compound 1-1-A (16 g, 36.5 mmol), (4-(6-phenylpyridazin-3-yl)phenyl)boronic acid (10.6 g, 38.3 mmol), tetrakis(triphenylphosphine)palladium(0) (1.3 g, 1.1 mmol), and potassium carbonate (10.1 g, 73 mmol) were put into a container, and the resulting mixture was heated and stirred for 6 hours. After the reaction was terminated, the temperature was lowered to normal temperature, and then a primary filtration was performed to remove impurities. The filtered material was put into water, extraction was performed by using chloroform to obtain an organic layer, and then the organic layer was dried over anhydrous magnesium sulfate. After distillation under reduced pressure, the residue was washed with ethanol to prepare Compound 1-1 (20 g, yield 93%).

MS: $[M+H]^+=589$

<Preparation Example 2> Synthesis of Compound 1-3

Under nitrogen flow, Compound 1-1-A (15 g, 34.2 mmol), (4'-cyano-[1,1'-biphenyl]-4-yl)boronic acid (8 g, 35.9 mmol), and potassium carbonate (9.5 g, 68.4 mmol) were put into a container, and the resulting mixture was heated and stirred. After reflux was performed, tetrakis(triphenylphosphine)palladium(0) (1.2 g, 1.0 mmol) was put thereinto, and the resulting mixture was additionally heated and stirred for 5 hours. After the reaction was terminated, the temperature was lowered to normal temperature, and then a primary filtration was performed to remove impurities. The filtered material was put into water, extraction was performed by using chloroform to obtain an organic layer, and then the organic layer was dried over anhydrous magnesium sulfate. After distillation under reduced pressure, the residue was washed with ethanol to prepare Compound 1-3 (16 g, yield 87%).

MS: $[M+H]^+=536$

<Preparation Example 3> Synthesis of Compound 1-4

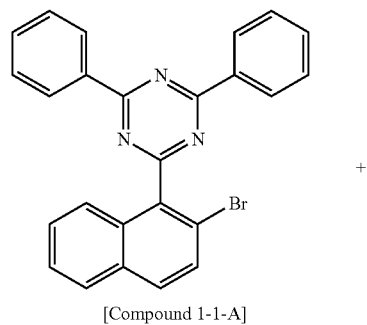

[Compound 1-1-A]

+

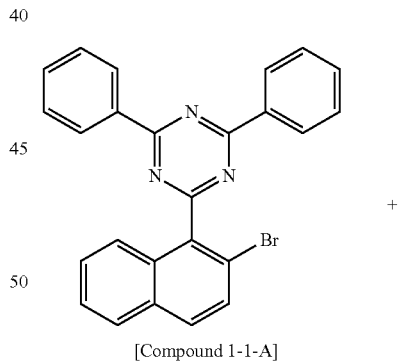

[Compound 1-1-A]

+

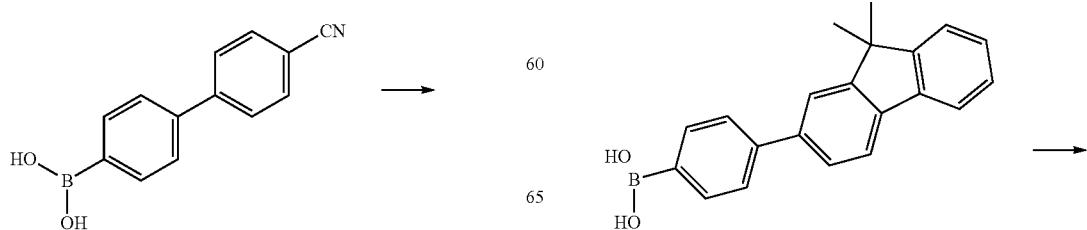

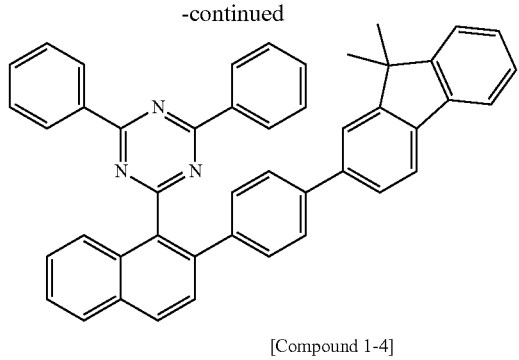

[Compound 1-4]

Compound 1-4 was obtained in the same manner as in the method for preparing Compound 1-1, except that (4-(9,9-dimethyl-9H-fluoren-2-yl)phenyl)boronic acid was used instead of (4-(6-phenylpyridazin-3-yl)phenyl)boronic acid.

MS: [M+H]$^+$=627

<Preparation Example 4> Synthesis of Compound 1-6

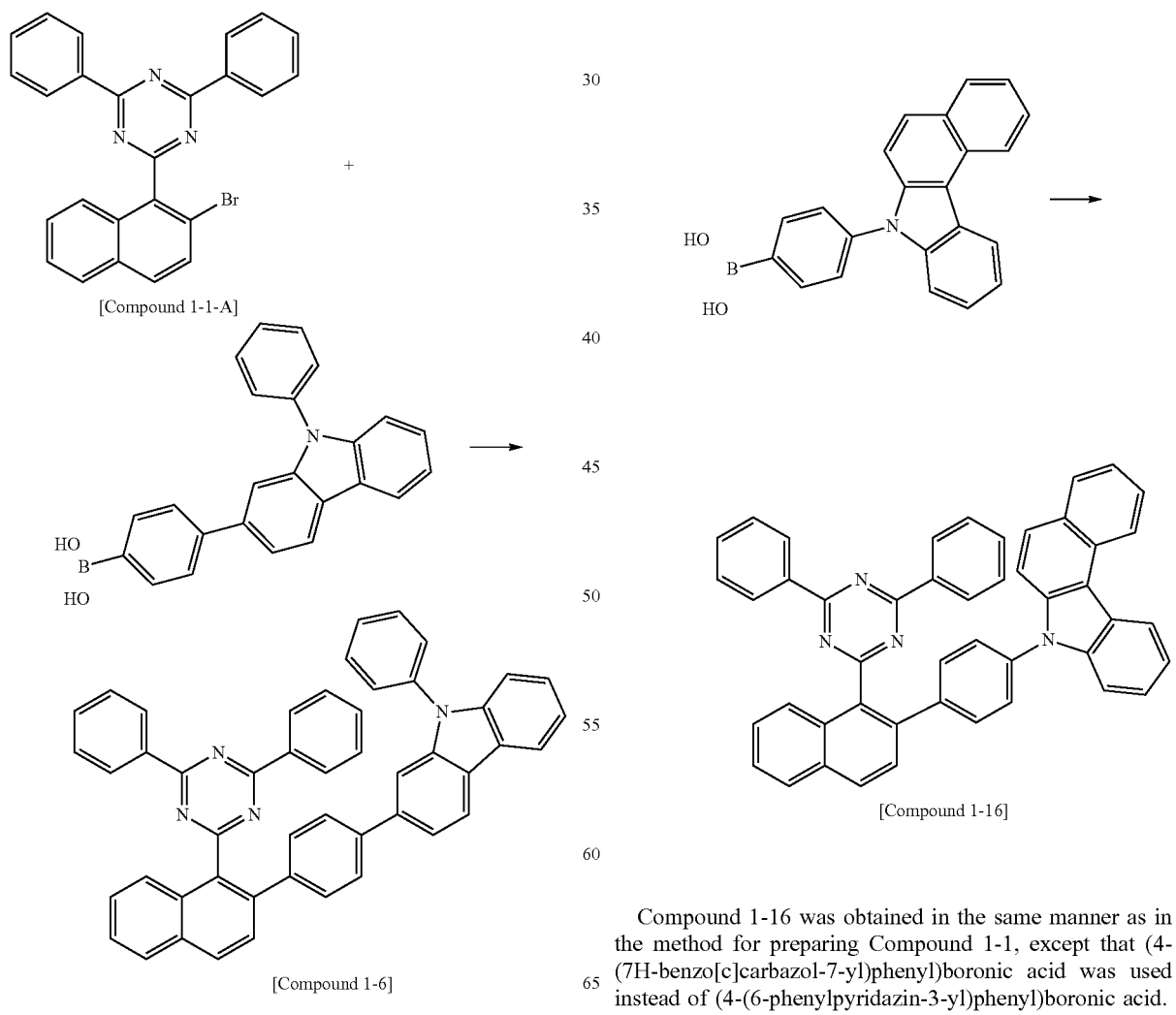

[Compound 1-1-A]

[Compound 1-6]

Compound 1-6 was obtained in the same manner as in the method for preparing Compound 1-1, except that (4-(9-phenyl-9H-carbazol-2-yl)phenyl)boronic acid was used instead of (4-(6-phenylpyridazin-3-yl)phenyl)boronic acid.

MS: [M+H]$^+$=676

<Preparation Example 5> Synthesis of Compound 1-16

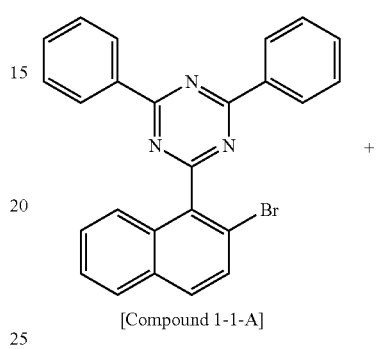

[Compound 1-1-A]

[Compound 1-16]

Compound 1-16 was obtained in the same manner as in the method for preparing Compound 1-1, except that (4-(7H-benzo[c]carbazol-7-yl)phenyl)boronic acid was used instead of (4-(6-phenylpyridazin-3-yl)phenyl)boronic acid.

MS: [M+H]$^+$=650

<Preparation Example 6> Synthesis of Compound 1-19

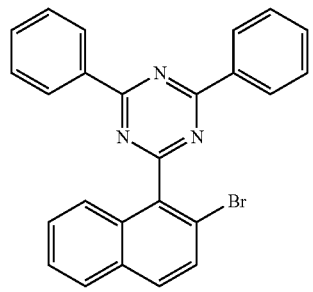

[Compound 1-1-A]

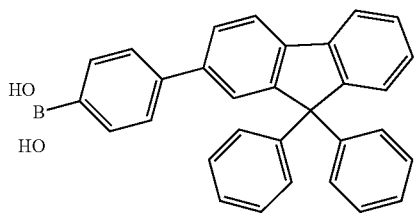

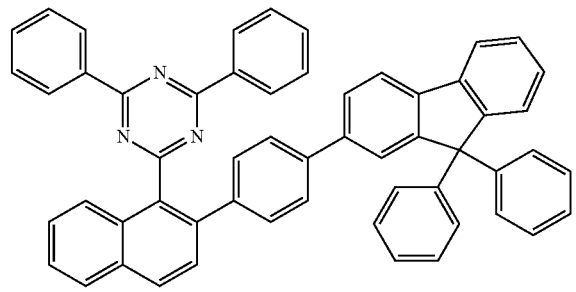

[Compound 1-19]

Compound 1-19 was obtained in the same manner as in the method for preparing Compound 1-1, except that (4-(9,9-diphenyl-9H-fluoren-2-yl)phenyl)boronic acid was used instead of (4-(6-phenylpyridazin-3-yl)phenyl)boronic acid.

MS: [M+H]⁺=751

<Preparation Example 7> Synthesis of Compound 1-27

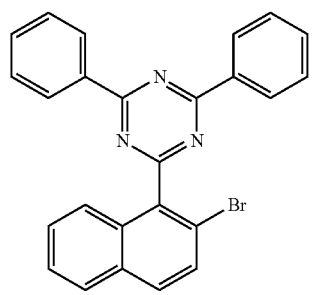

[Compound 1-1-A]

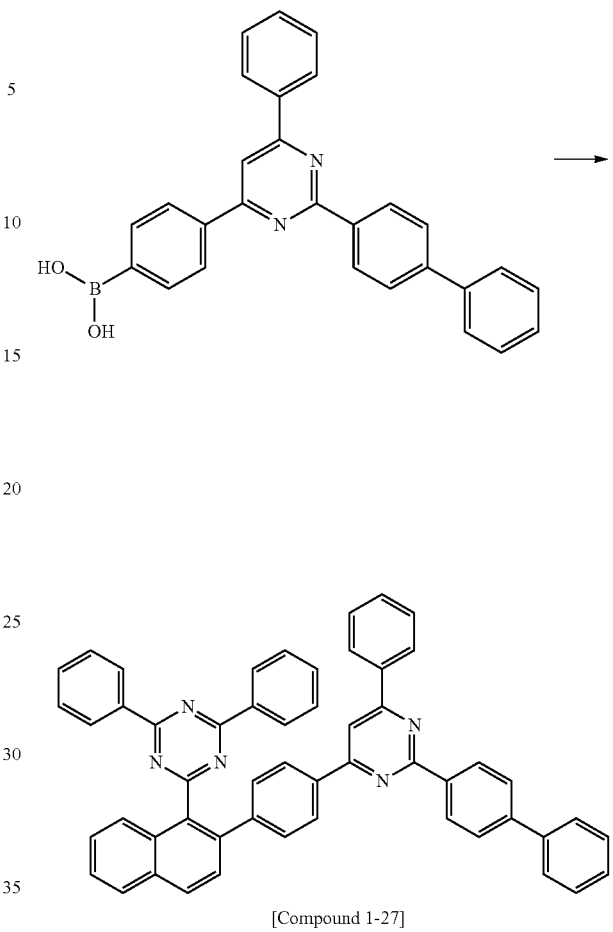

[Compound 1-27]

Compound 1-27 was obtained in the same manner as in the method for preparing Compound 1-1, except that (4-(2-([1,1'-biphenyl]-4-yl)-6-phenylpyrimidin-4-yl)phenyl)boronic acid was used instead of (4-(6-phenylpyridazin-3-yl)phenyl)boronic acid.

MS: [M+H]⁺=741

<Preparation Example 8> Synthesis of Compound 1-36

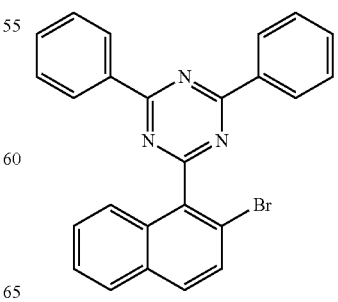

[Compound 1-1-A]

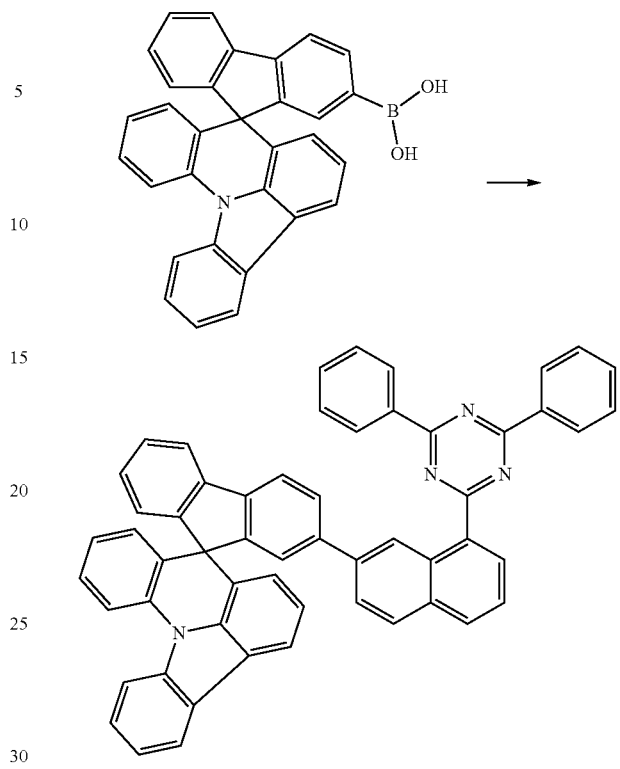

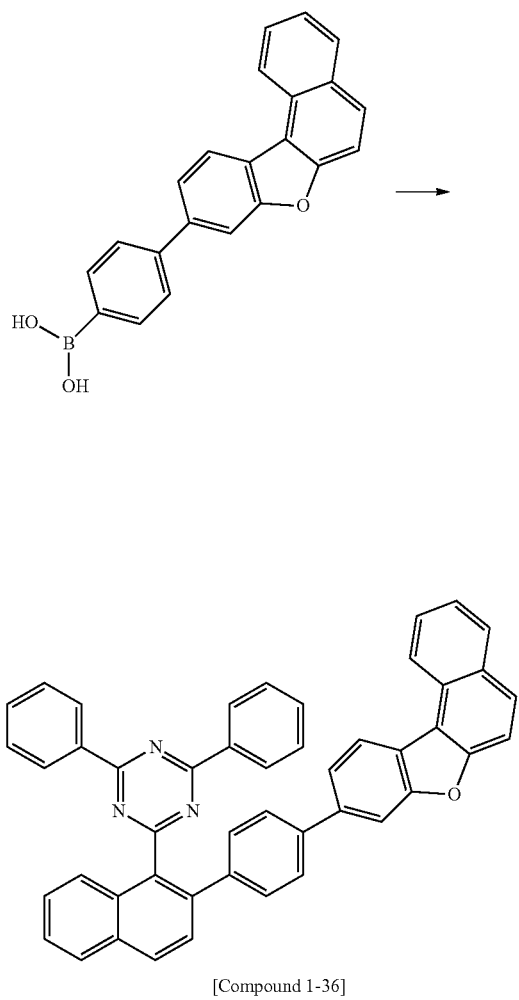

[Compound 1-36]

Compound 1-36 was obtained in the same manner as in the method for preparing Compound 1-1, except that (4-(naphtho[2,1-b]benzofuran-9-yl)phenyl)boronic acid was used instead of (4-(6-phenylpyridazin-3-yl)phenyl)boronic acid.

MS: [M+H]⁺=651

<Preparation Example 9> Synthesis of Compound 1-38

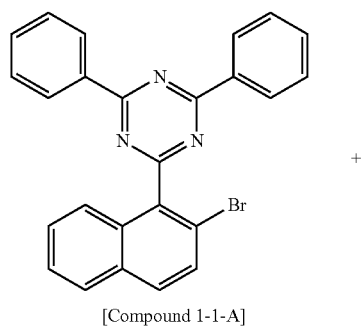

[Compound 1-1-A]

[Compound 1-38]

Compound 1-38 was obtained in the same manner as in the method for preparing Compound 1-1, except that spiro[fluoren-9,8'-indolo[3,2,1-de]acridin]-2-yl boronic acid was used instead of (4-(6-phenylpyridazin-3-yl)phenyl)boronic acid.

MS: [M+H]⁺=762

<Preparation Example 10> Synthesis of Compound 1-39

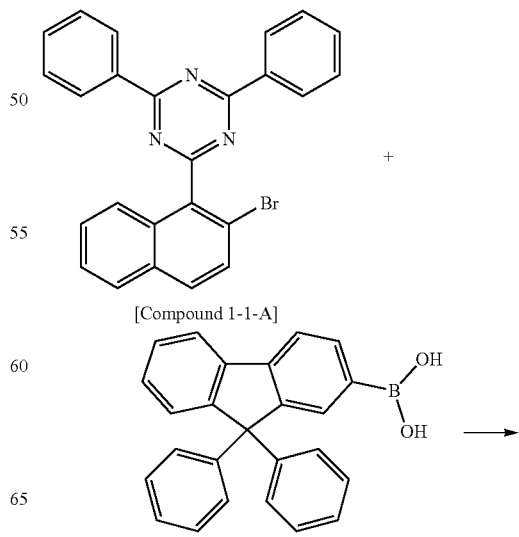

[Compound 1-1-A]

-continued

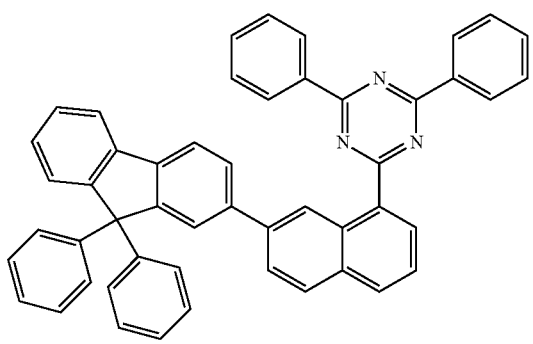

[Compound 1-39]

Compound 1-39 was obtained in the same manner as in the method for preparing Compound 1-1, except that (9,9-diphenyl-9H-fluoren-2-yl)boronic acid was used instead of (4-(6-phenylpyridazin-3-yl)phenyl)boronic acid.

MS: $[M+H]^+=675$

<Preparation Example 11> Synthesis of Compound 2-31

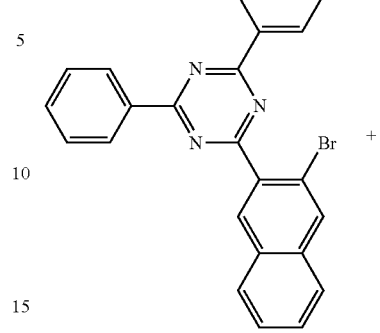

[Compound 2-1-A]

Compound 2-1-A was obtained in the same manner as in the method for preparing Compound 1-1-A, except that 3-bromo-2-naphthaldehyde was used instead of 2-bromo-1-naphthaldehyde.

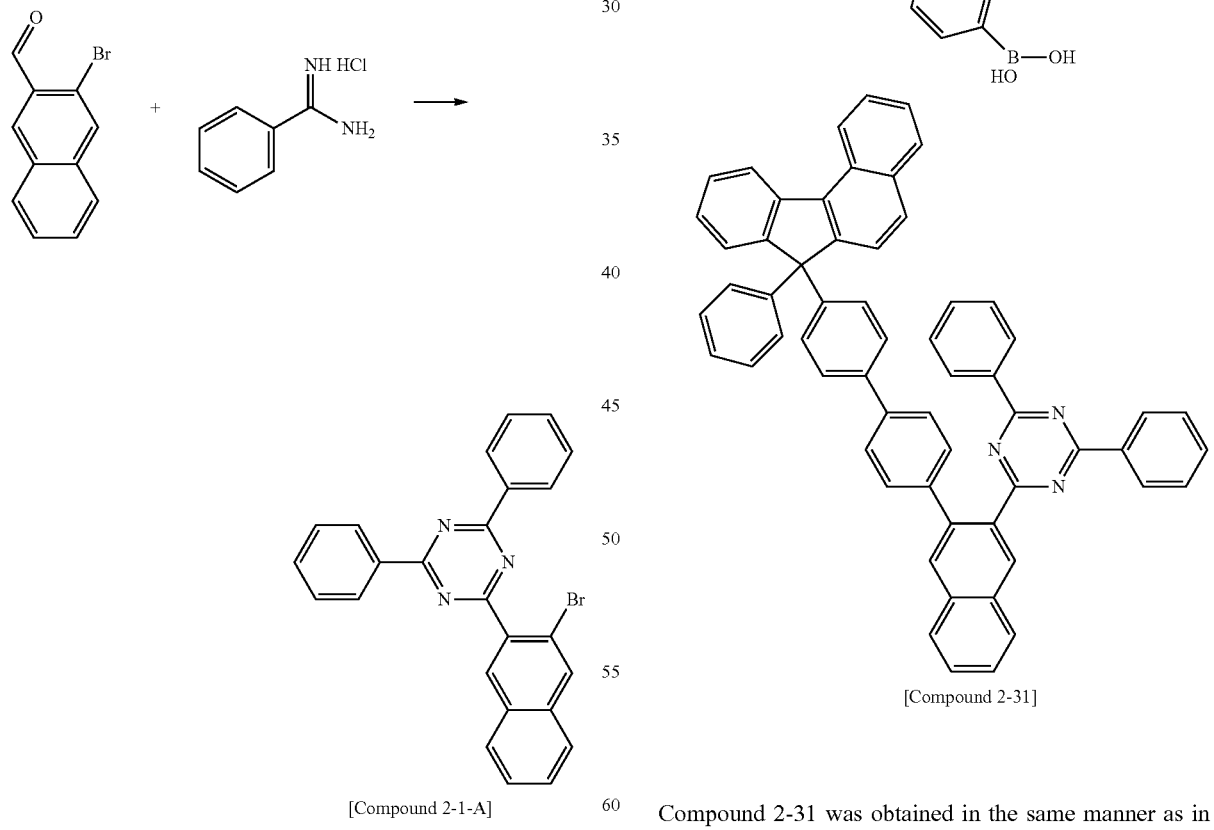

[Compound 2-31]

Compound 2-31 was obtained in the same manner as in the method for preparing Compound 1-1, except that [Compound 2-1-A] was used instead of [Compound 1-1-A], and (4'-(7-phenyl-7H-benzo[c]fluoren-7-yl)-[1,1'-biphenyl]-4-yl)boronic acid was used instead of (4-(6-phenylpyridazin-3-yl)phenyl)boronic acid.

MS: $[M+H]^+=801$

<Preparation Example 12> Synthesis of Compound 2-33

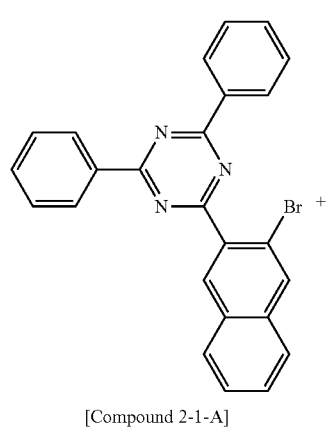

Compound 2-33 was obtained in the same manner as in the method for preparing Compound 1-1, except that [Compound 2-1-A] was used instead of [Compound 1-1-A], and triphenylene-2-yl boronic acid was used instead of (4-(6-phenylpyridazin-3-yl)phenyl)boronic acid.

MS: [M+H]$^+$=585

<Preparation Example 13> Synthesis of Compound 2-35

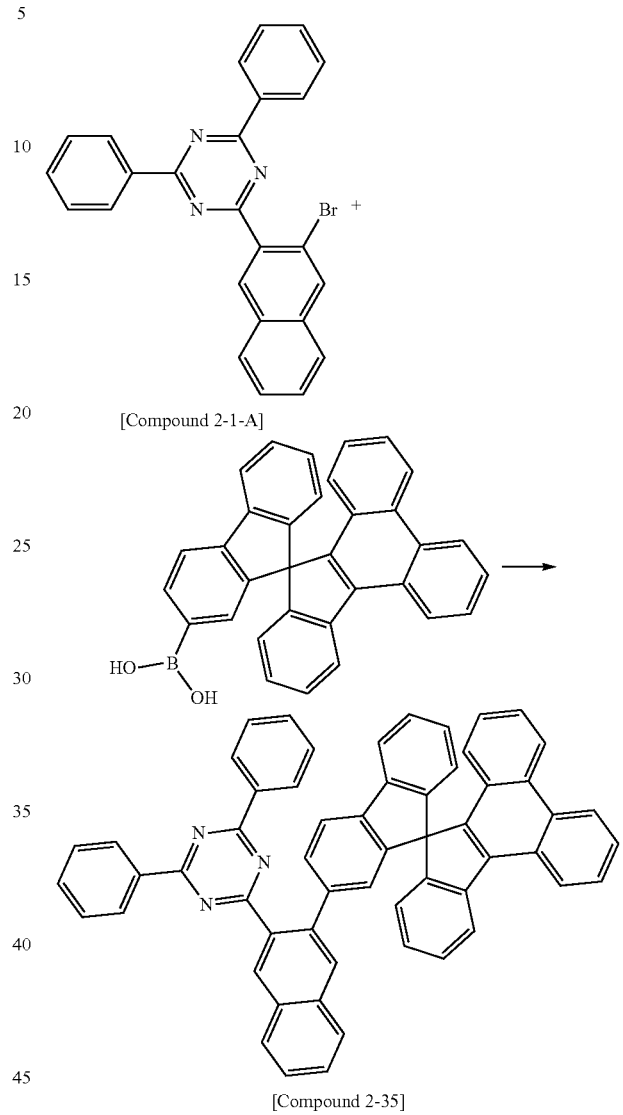

Compound 2-35 was obtained in the same manner as in the method for preparing Compound 1-1, except that [Compound 2-1-A] was used instead of [Compound 1-1-A], and spiro[fluoren-9,13'-indeno[1,2-yl]phenanthren]-2-yl]boronic acid was used instead of (4-(6-phenylpyridazin-3-yl)phenyl)boronic acid.

MS: [M+H]$^+$=773

<Preparation Example 14> Synthesis of Compound 3-16

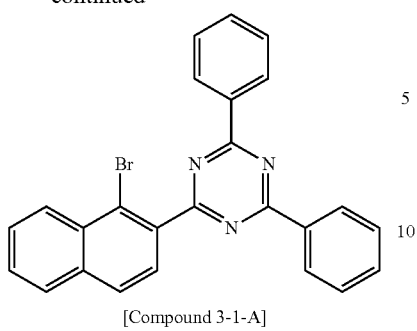

[Compound 3-1-A]

Compound 3-1-A was obtained in the same manner as in the method for preparing Compound 1-1-A, except that 1-bromo-2-naphthaldehyde was used instead of 2-bromo-1-naphthaldehyde.

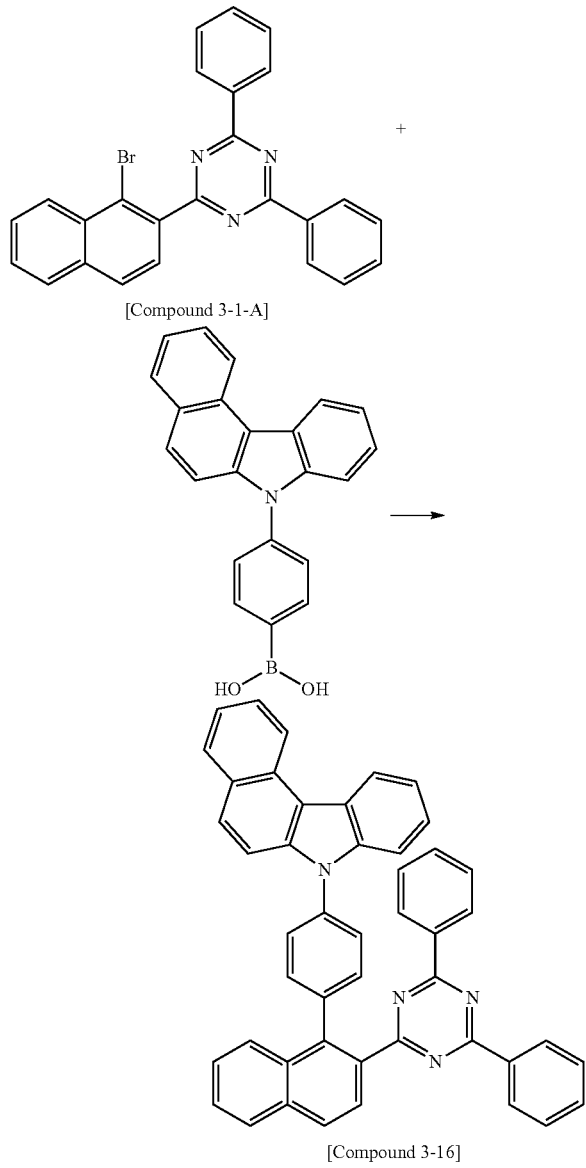

[Compound 3-16]

Compound 3-16 was obtained in the same manner as in the method for preparing Compound 1-1, except that [Compound 3-1-A] was used instead of [Compound 1-1-A], and (4-(7H-benzo[c]carbazol-7-yl)phenyl)boronic acid was used instead of (4-(6-phenylpyridazin-3-yl)phenyl)boronic acid.

MS: [M+H]$^+$=650

<Preparation Example 15> Synthesis of Compound 3-22

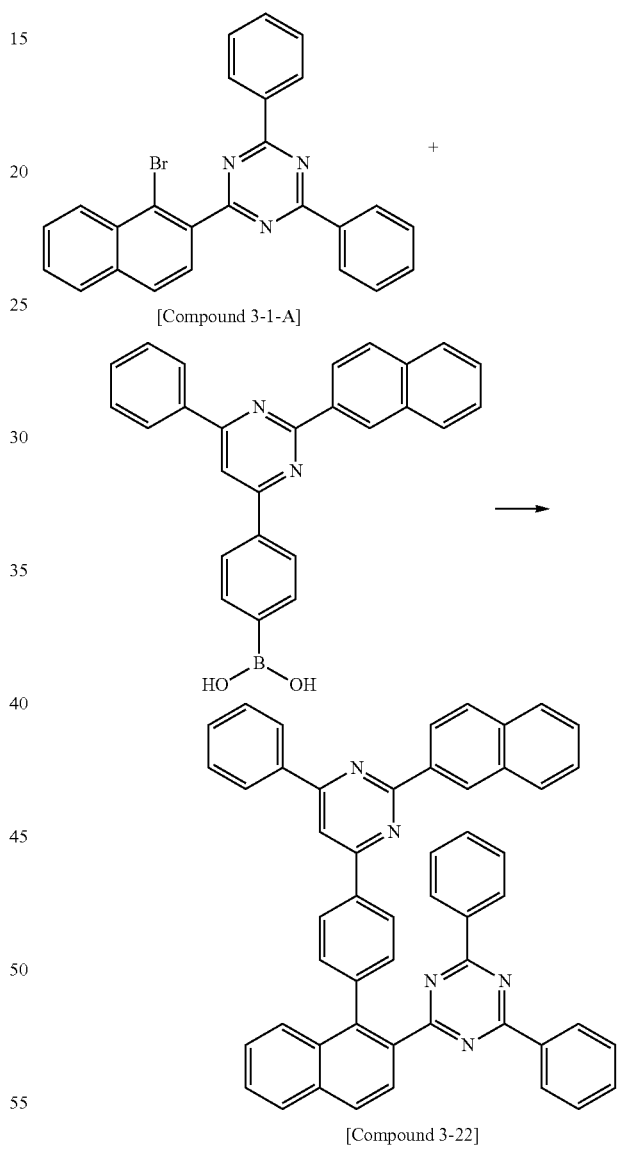

[Compound 3-22]

Compound 3-22 was obtained in the same manner as in the method for preparing Compound 1-1, except that [Compound 3-1-A] was used instead of [Compound 1-1-A], and (4-(2-(naphthalen-2-yl)-6-phenylpyrimidin-4-yl)phenyl)boronic acid was used instead of (4-(6-phenylpyridazin-3-yl)phenyl)boronic acid.

MS: [M+H]$^+$=715

<Preparation Example 16> Synthesis of Compound 3-33

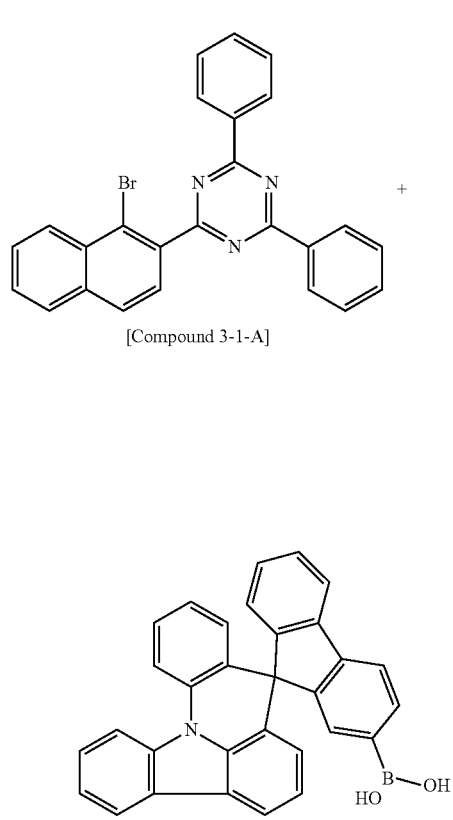

[Compound 3-1-A]

[Compound 3-33]

Compound 3-33 was obtained in the same manner as in the method for preparing Compound 1-1, except that [Compound 3-1-A] was used instead of [Compound 1-1-A], and spiro[fluoren-9,8'-indolo[3,2,1-de]acridin]-2-yl boronic acid was used instead of (4-(6-phenylpyridazin-3-yl)phenyl)boronic acid.

MS: [M+H]$^+$=762

<Preparation Example 17> Synthesis of Compound 3-34

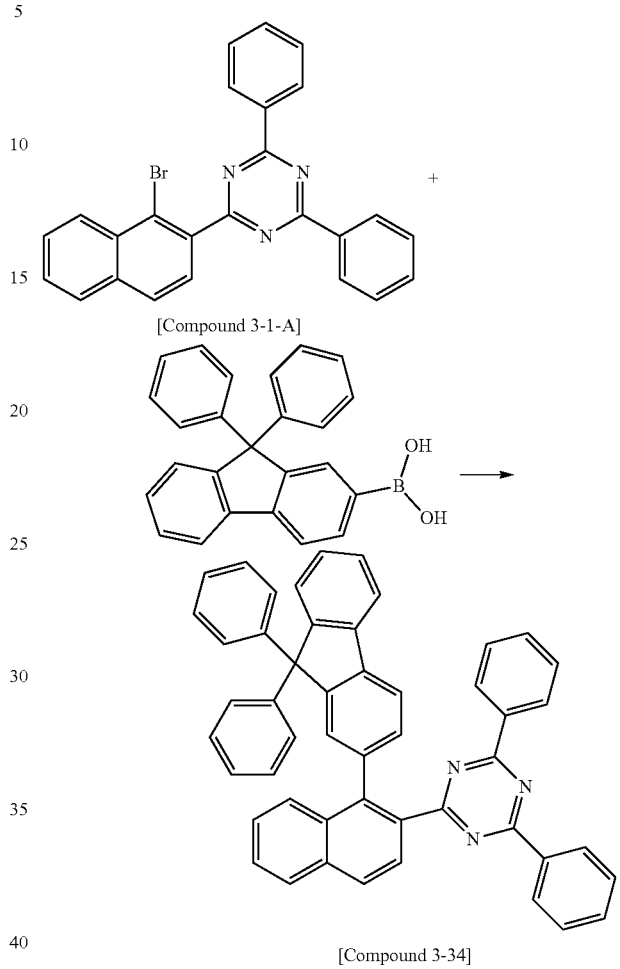

[Compound 3-1-A]

[Compound 3-34]

Compound 3-34 was obtained in the same manner as in the method for preparing Compound 1-1, except that [Compound 3-1-A] was used instead of [Compound 1-1-A], and (9,9-diphenyl-9H-fluoren-2-yl)boronic acid was used instead of (4-(6-phenylpyridazin-3-yl)phenyl)boronic acid.

MS: [M+H]$^+$=675

<Preparation Example 18> Synthesis of Compound 3-35

[Compound 3-1-A]

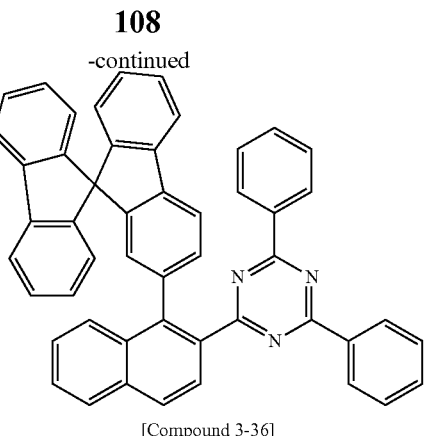

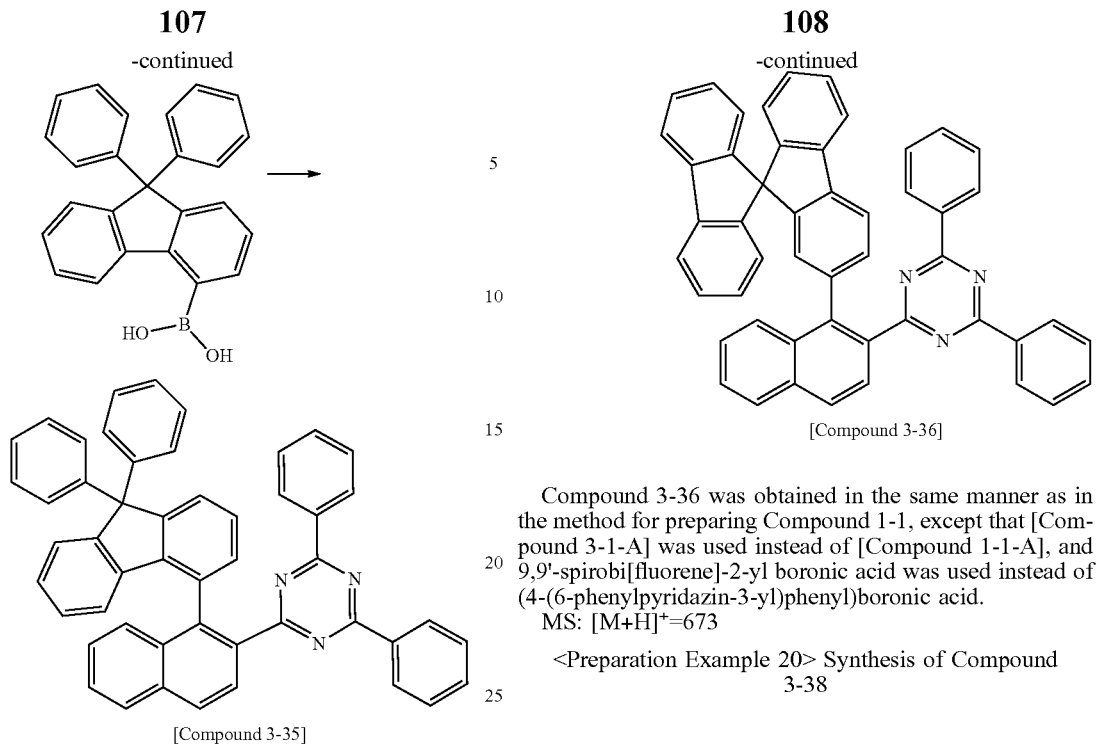

[Compound 3-35]

Compound 3-35 was obtained in the same manner as in the method for preparing Compound 1-1, except that [Compound 3-1-A] was used instead of [Compound 1-1-A], and (9,9-diphenyl-9H-fluoren-4-yl)boronic acid was used instead of (4-(6-phenylpyridazin-3-yl)phenyl)boronic acid.

MS: [M+H]$^+$=675

<Preparation Example 19> Synthesis of Compound 3-36

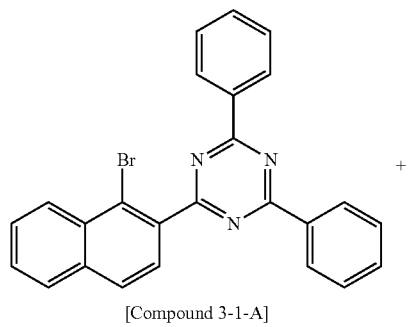

[Compound 3-36]

Compound 3-36 was obtained in the same manner as in the method for preparing Compound 1-1, except that [Compound 3-1-A] was used instead of [Compound 1-1-A], and 9,9'-spirobi[fluorene]-2-yl boronic acid was used instead of (4-(6-phenylpyridazin-3-yl)phenyl)boronic acid.

MS: [M+H]$^+$=673

<Preparation Example 20> Synthesis of Compound 3-38

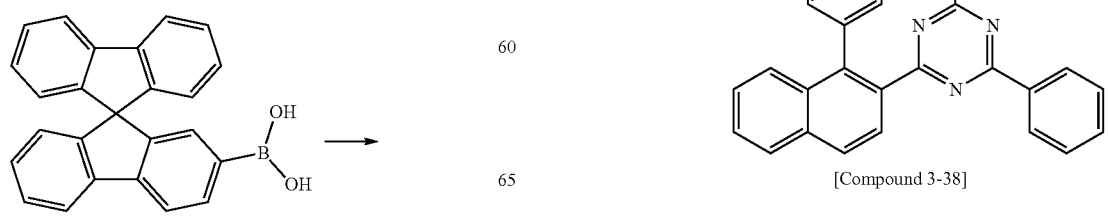

[Compound 3-38]

Compound 3-38 was obtained in the same manner as in the method for preparing Compound 1-1, except that [Compound 3-1-A] was used instead of [Compound 1-1-A], and triphenylene-2-yl boronic acid was used instead of (4-(6-phenylpyridazin-3-yl)phenyl)boronic acid.

MS: [M+H]$^+$=585

<Preparation Example 21> Synthesis of Compound 3-39

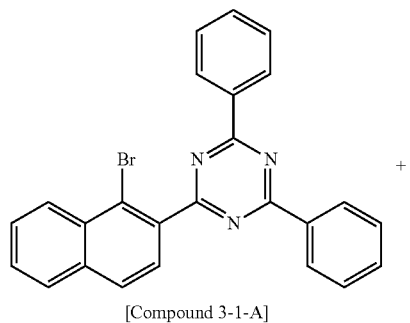

[Compound 3-1-A]

+

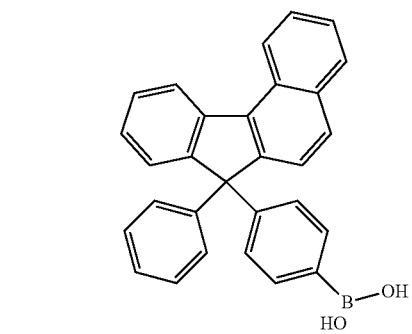

→

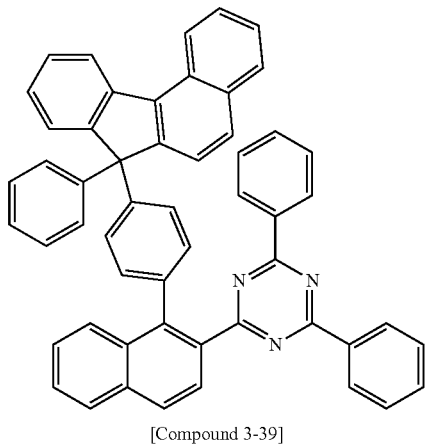

[Compound 3-39]

Compound 3-39 was obtained in the same manner as in the method for preparing Compound 1-1, except that [Compound 3-1-A] was used instead of [Compound 1-1-A], and (4-(7-phenyl-7H-benzo[c]fluoren-7-yl)phenyl)boronic acid was used instead of (4-(6-phenylpyridazin-3-yl)phenyl)boronic acid.

MS: [M+H]$^+$=725

<Preparation Example 22> Synthesis of Compound 3-47

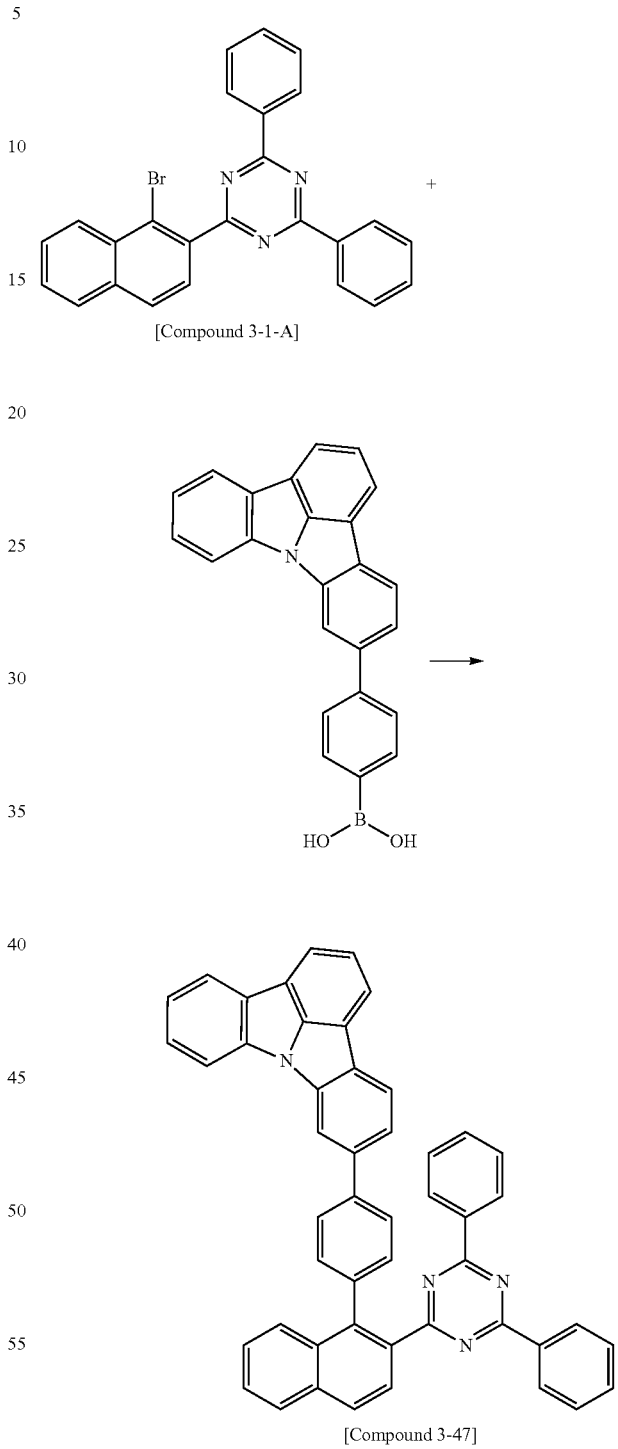

Compound 3-47 was obtained in the same manner as in the method for preparing Compound 1-1, except that [Compound 3-1-A] was used instead of [Compound 1-1-A], and (4-(indolo[3,2,1-jk]carbazol-10-yl)phenyl)boronic acid was used instead of (4-(6-phenylpyridazin-3-yl)phenyl)boronic acid.

MS: [M+H]$^+$=674

‹Preparation Example 23› Synthesis of Compound 4-4

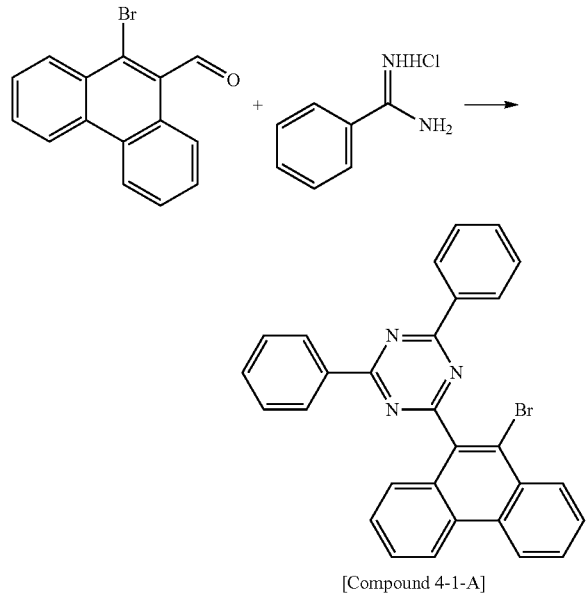

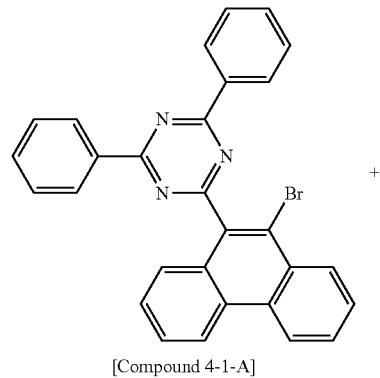

[Compound 4-1-A]

Compound 4-1-A was obtained in the same manner as in the method for preparing Compound 1-1-A, except that 10-bromophenanthrene-9-carbaldehyde was used instead of 2-bromo-1-naphthaldehyde.

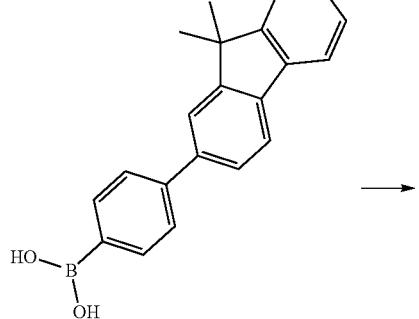

[Compound 4-1-A]

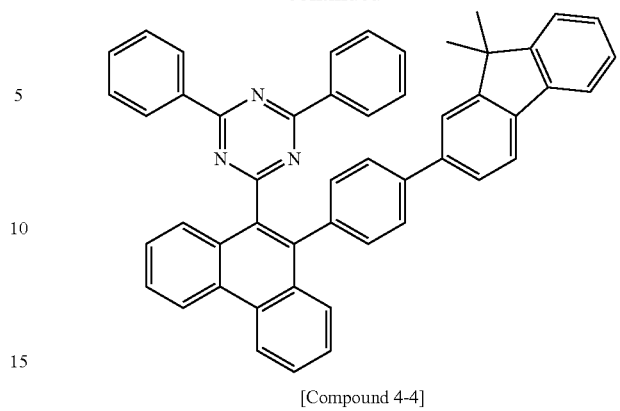

[Compound 4-4]

Compound 4-4 was obtained in the same manner as in the method for preparing Compound 1-1, except that [Compound 4-1-A] was used instead of [Compound 1-1-A], and (4-(9,9-dimethyl-9H-fluoren-2-yl)phenyl)boronic acid was used instead of (4-(6-phenylpyridazin-3-yl)phenyl)boronic acid.

MS: [M+H]$^+$=677

‹Preparation Example 24› Synthesis of Compound 4-12

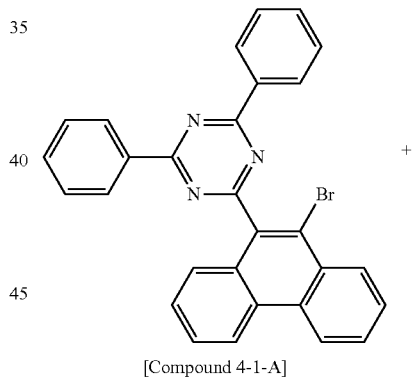

[Compound 4-1-A]

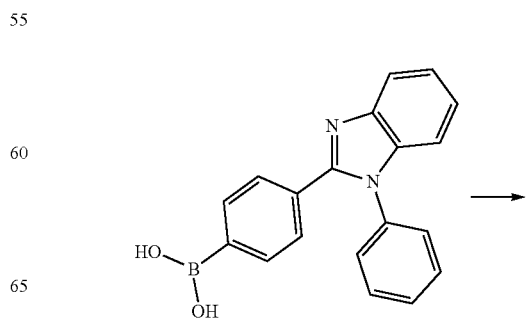

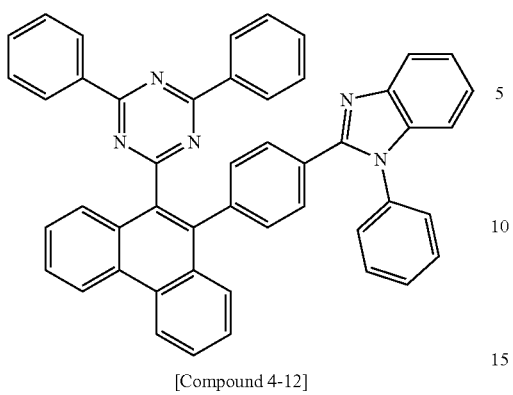

[Compound 4-12]

Compound 4-12 was obtained in the same manner as in the method for preparing Compound 1-1, except that [Compound 4-1-A] was used instead of [Compound 1-1-A], and (4-(1-phenyl-1H-benzo[d]imidazol-2-yl)phenyl)boronic acid was used instead of (4-(6-phenylpyridazin-3-yl)phenyl)boronic acid.

MS: [M+H]⁺=677

<Preparation Example 25> Synthesis of Compound 4-37

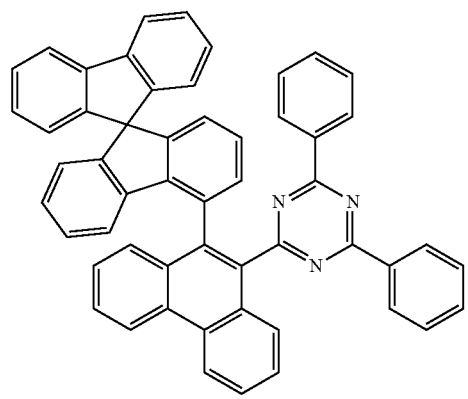

[Compound 4-37]

Compound 4-37 was obtained in the same manner as in the method for preparing Compound 1-1, except that [Compound 4-1-A] was used instead of [Compound 1-1-A], and 9,9'-spirobi[fluorene]-4-yl boronic acid was used instead of (4-(6-phenylpyridazin-3-yl)phenyl)boronic acid.

MS: [M+H]⁺=723

<Preparation Example 26> Synthesis of Compound 4-51

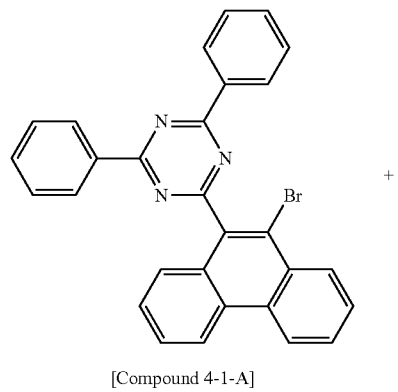

[Compound 4-1-A]

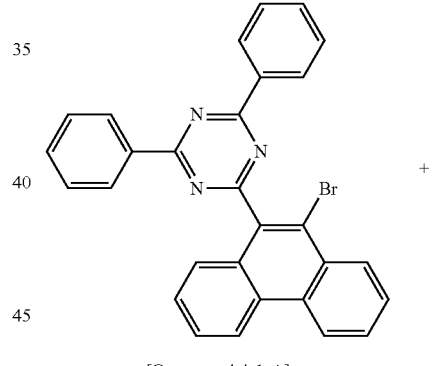

[Compound 4-1-A]

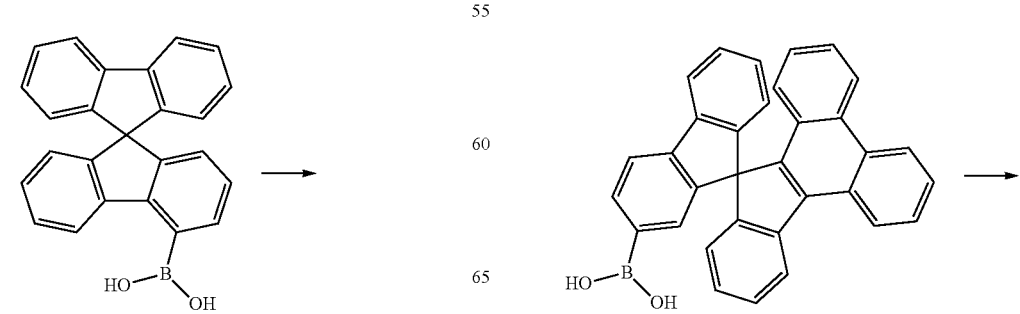

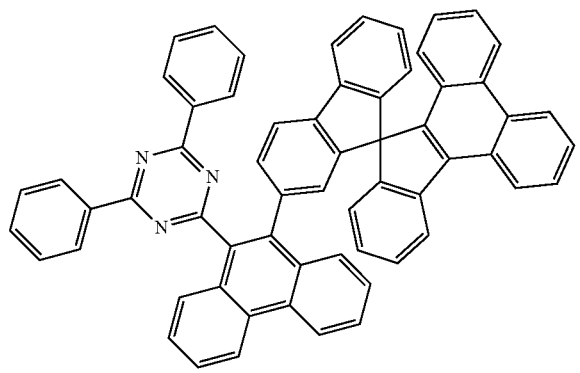

[Compound 4-51]

Compound 4-51 was obtained in the same manner as in the method for preparing Compound 1-1, except that [Compound 4-1-A] was used instead of [Compound 1-1-A], and spiro[fluoren-9,9'-indeno[2,1-1]phenanthren]-2-yl boronic acid was used instead of (4-(6-phenylpyridazin-3-yl)phenyl)boronic acid.

MS: [M+H]$^+$=823

<Preparation Example 27> Synthesis of Compound 5-10

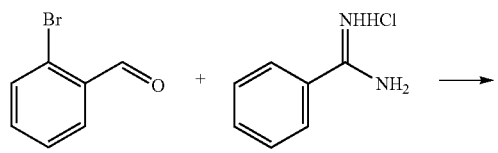

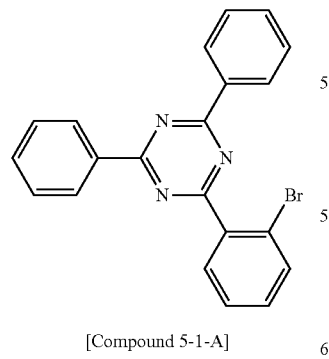

[Compound 5-1-A]

Compound 5-1-A was obtained in the same manner as in the method for preparing Compound 1-1-A, except that 2-bromobenzaldehyde was used instead of 2-bromo-1-naphthaldehyde.

[Compound 5-1-A]

[Compound 5-10]

Compound 5-10 was obtained in the same manner as in the method for preparing Compound 1-1, except that [Compound 5-1-A] was used instead of [Compound 1-1-A], and (6-(1-methyl-1H-benzo[d]imidazol-2-yl)naphthalen-2-yl)boronic acid was used instead of (4-(6-phenylpyridazin-3-yl)phenyl)boronic acid.

MS: [M+H]$^+$=565

<Preparation Example 28> Synthesis of Compound 5-28

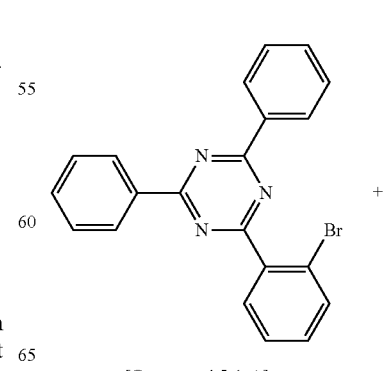

[Compound 5-1-A]

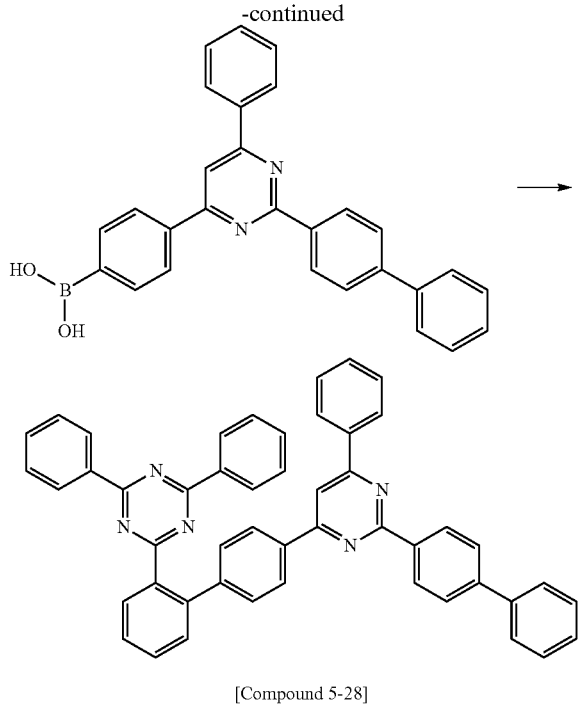

[Compound 5-28]

Compound 5-28 was obtained in the same manner as in the method for preparing Compound 1-1, except that [Compound 5-1-A] was used instead of [Compound 1-1-A], and (4-(2-([1,1'-biphenyl]-4-yl)-6-phenylpyrimidin-4-yl)phenyl)boronic acid was used instead of (4-(6-phenylpyridazin-3-yl)phenyl)boronic acid.

MS: [M+H]⁺=691

<Preparation Example 29> Synthesis of Compound 5-52

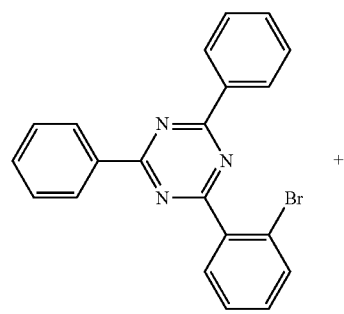

[Compound 5-1-A]

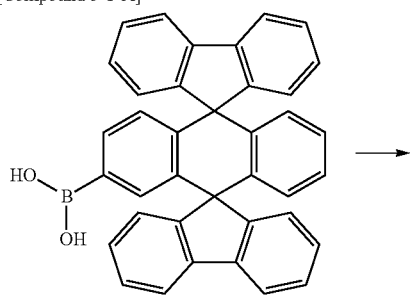

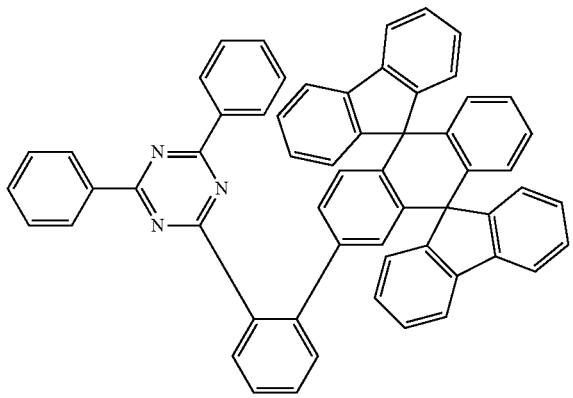

[Compound 5-52]

Compound 5-52 was obtained in the same manner as in the method for preparing Compound 1-1, except that [Compound 5-1-A] was used instead of [Compound 1-1-A], and dispiro[fluoren-9,9'-anthracen-10',9'-fluoren]-2'-yl boronic acid was used instead of (4-(6-phenylpyridazin-3-yl)phenyl)boronic acid.

MS: [M+H]⁺=787

<Preparation Example 30> Synthesis of Compound 3-48

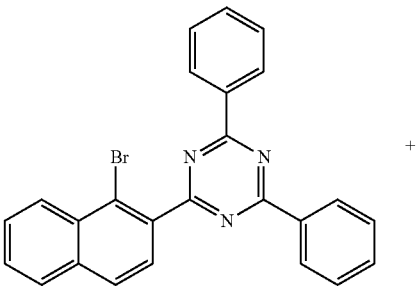

[Compound 3-1-A]

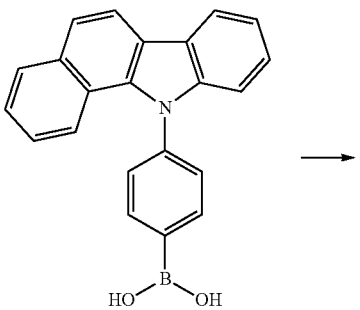

119
-continued

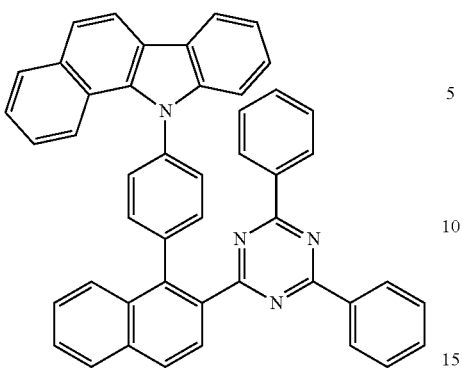

[Compound 3-48]

Compound 3-48 was obtained in the same manner as in the method for preparing Compound 1-1, except that [Compound 3-1-A] was used instead of [Compound 1-1-A], and (4-(11H-benzo[a]carbazol-11-yl)phenyl boronic acid was used instead of (4-(6-phenylpyridazin-3-yl)phenyl)boronic acid.

MS: [M+H]$^+$=650

<Preparation Example 31> Synthesis of Compound 3-50

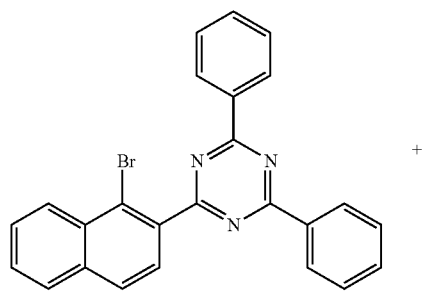

[Compound 3-1-A]

120
-continued

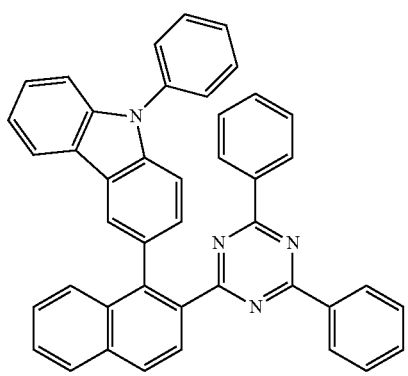

[Compound 3-50]

Compound 3-50 was obtained in the same manner as in the method for preparing Compound 1-1, except that [Compound 3-1-A] was used instead of [Compound 1-1-A], and (9-phenyl-9H-carbazol-3-yl)boronic acid was used instead of (4-(6-phenylpyridazin-3-yl)phenyl)boronic acid.

MS: [M+H]$^+$=600

<Preparation Example 32> Synthesis of Compound 1-17

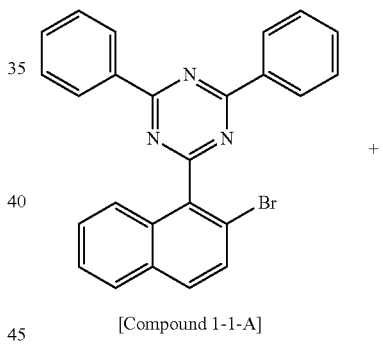

[Compound 1-1-A]

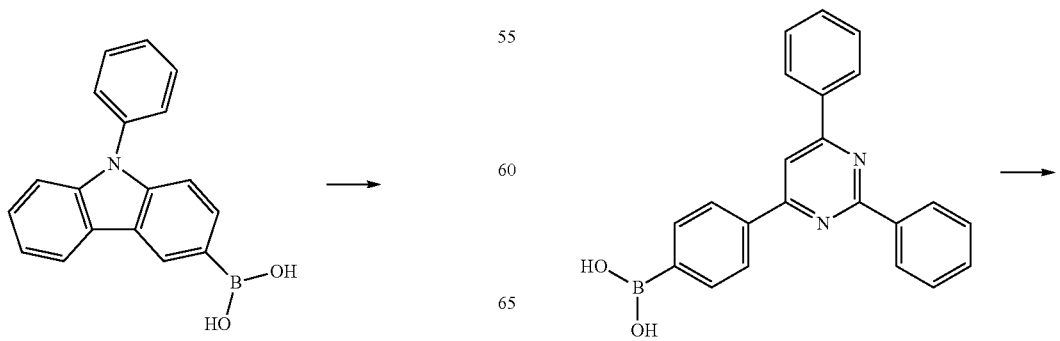

-continued

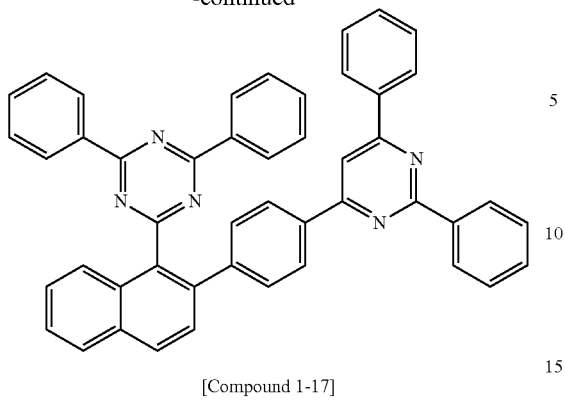

[Compound 1-17]

Compound 1-17 was obtained in the same manner as in the method for preparing Compound 1-1, except that (4-(2,6-diphenylpyrimidin-4-yl)phenyl)boronic acid was used instead of (4-(6-phenylpyridazin-3-yl)phenyl)boronic acid.

MS: $[M+H]^+=665$

EXAMPLE

Example 1

A glass substrate (Corning 7059 glass) thinly coated with ITO (indium tin oxide) to have a thickness of 1,000 Å was put into distilled water in which a dispersant was dissolved, and ultrasonically washed.

A product manufactured by Fischer Co., was used as the detergent, and distilled water twice filtered using a filter manufactured by Millipore Co., was used as the distilled water. After the ITO was washed for 30 minutes, ultrasonic washing was conducted twice repeatedly using distilled water for 10 minutes. After the washing using distilled water was completed, ultrasonic washing was conducted using isopropyl alcohol, acetone, and methanol solvents in this order, and drying was then conducted.

Hexanitrile hexaazatriphenylene was thermally vacuum deposited to have a thickness of 500 Å on a transparent ITO electrode, which was thus prepared, thereby forming a hole injection layer. HT1 (400 Å), which is a material for transporting holes, was vacuum deposited thereon, and then a compound of a host H1 and a dopant D1 was vacuum deposited as a light emitting layer to have a thickness of 300 Å. Compound 1-3 prepared in Preparation Example 1 and lithium quinolate (LiQ) were vacuum deposited at a weight ratio of 1:1 on the light emitting layer, thereby forming an electron injection and transport layer having a thickness of 350 Å.

Lithium fluoride (LiF) and aluminum were sequentially deposited on the electron injection and transport layer to have a thickness of 12 Å and 2,000 Å, respectively, thereby forming a negative electrode.

An organic light emitting device was manufactured.

In the aforementioned procedure, the deposition rate of the organic material was maintained at 0.4 to 0.7 Å/sec, the deposition rates of lithium fluoride and aluminum of the negative electrode were maintained at 0.3 Å/sec and at 2 Å/sec, respectively, and the degree of vacuum during the deposition was maintained at $2\times10^{-7}$ to $5\times10^{-6}$ torr, thereby manufacturing an organic light emitting device.

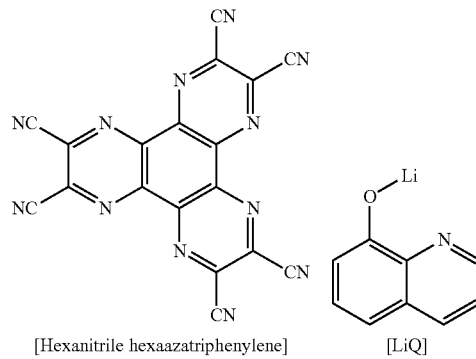

[Hexanitrile hexaazatriphenylene]     [LiQ]

[HT1]

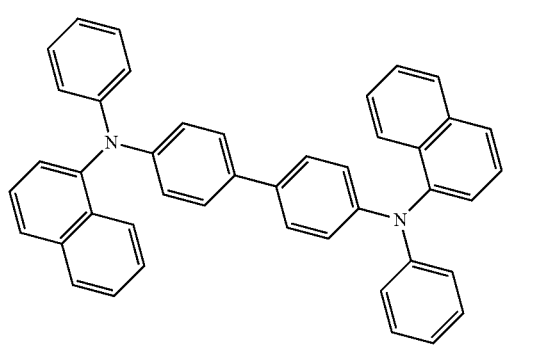

[H1]

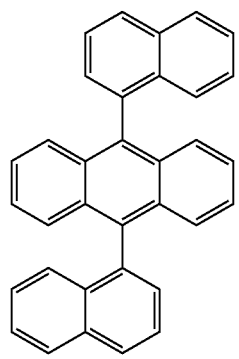

[D1]

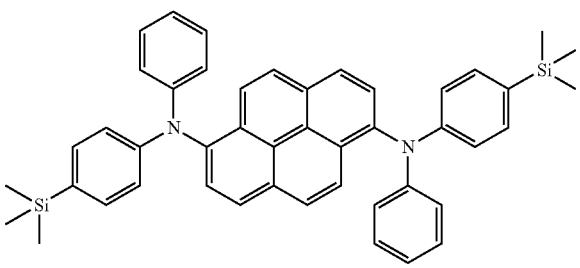

Example 2

An experiment was performed in the same manner as in Example 1, except that as the electron transport layer, Compound 1-4 was used instead of Compound 1-3.

Example 3

An experiment was performed in the same manner as in Example 1, except that as the electron transport layer, Compound 1-16 was used instead of Compound 1-3.

Example 4

An experiment was performed in the same manner as in Example 1, except that as the electron transport layer, Compound 2-31 was used instead of Compound 1-3.

Example 5

An experiment was performed in the same manner as in Example 1, except that as the electron transport layer, Compound 3-33 was used instead of Compound 1-3.

Example 6

An experiment was performed in the same manner as in Example 1, except that as the electron transport layer, Compound 3-34 was used instead of Compound 1-3.

Example 7

An experiment was performed in the same manner as in Example 1, except that as the electron transport layer, Compound 3-36 was used instead of Compound 1-3.

Example 8

An experiment was performed in the same manner as in Example 1, except that as the electron transport layer, Compound 3-38 was used instead of Compound 1-3.

Example 9

An experiment was performed in the same manner as in Example 1, except that as the electron transport layer, Compound 3-39 was used instead of Compound 1-3.

Example 10

An experiment was performed in the same manner as in Example 1, except that as the electron transport layer, Compound 3-47 was used instead of Compound 1-3.

Example 11

An experiment was performed in the same manner as in Example 1, except that as the electron transport layer, Compound 4-12 was used instead of Compound 1-3.

Example 12

An experiment was performed in the same manner as in Example 1, except that as the electron transport layer, Compound 5-28 was used instead of Compound 1-3.

Example 13

An experiment was performed in the same manner as in Example 1, except that as the electron transport layer, Compound 3-48 was used instead of Compound 1-3.

Example 14

An experiment was performed in the same manner as in Example 1, except that as the electron transport layer, Compound 3-50 was used instead of Compound 1-3.

Example 15

An experiment was performed in the same manner as in Example 1, except that as the electron transport layer, Compound 1-17 was used instead of Compound 1-3.

Comparative Example 1

An experiment was performed in the same manner as in Example 1, except that as the electron transport layer, the following compound ET1 was used instead of Compound 1-3.

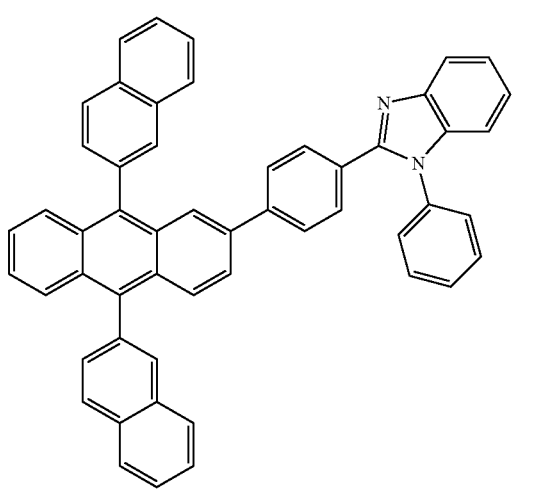

[ET1]

Comparative Example 2

An experiment was performed in the same manner as in Example 1, except that as the electron transport layer, the following compound ET2 was used instead of Compound 1-3.

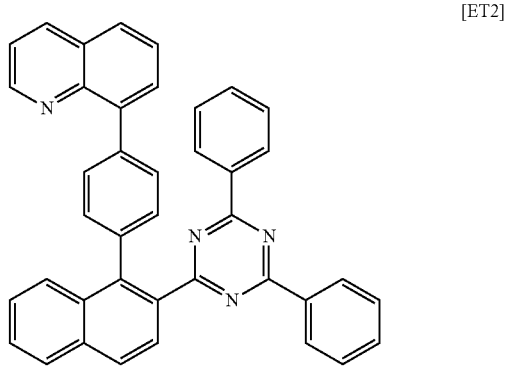 [SMILES: c1ccc(-c2nc(-c3ccccc3)nc(-c3ccc4ccccc4c3-c3ccc(-c4cccc5cccnc45)cc3)n2)cc1]

[ET2]

Comparative Example 3

An experiment was performed in the same manner as in Example 1, except that as the electron transport layer, the following compound ET3 was used instead of Compound 1-3.

[ET3]

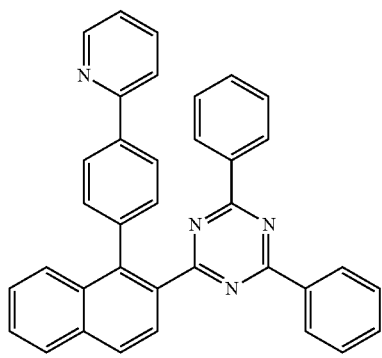

Comparative Example 4

An experiment was performed in the same manner as in Example 1, except that as the electron transport layer, the following compound ET4 was used instead of Compound 1-3.

[ET4]

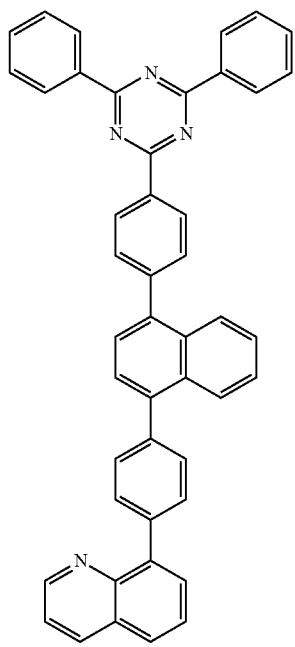

Comparative Example 5

An experiment was performed in the same manner as in Example 1, except that as the electron transport layer, the following compound ET5 was used instead of Compound 1-3.

[ET5]

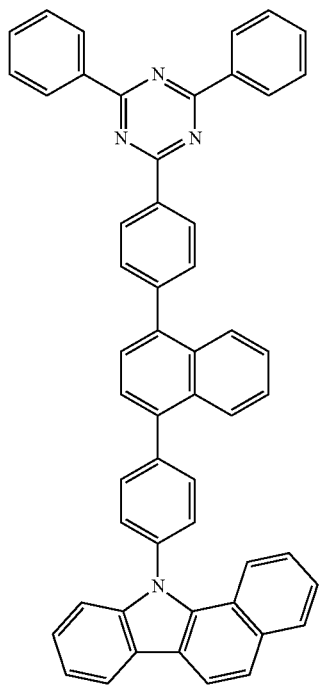

Comparative Example 6

An experiment was performed in the same manner as in Example 1, except that as the electron transport layer, the following compound ET6 was used instead of Compound 1-3.

[ET6]

Comparative Example 7

An experiment was performed in the same manner as in Example 1, except that as the electron transport layer, the following compound ET7 was used instead of Compound 1-3.

[ET7]

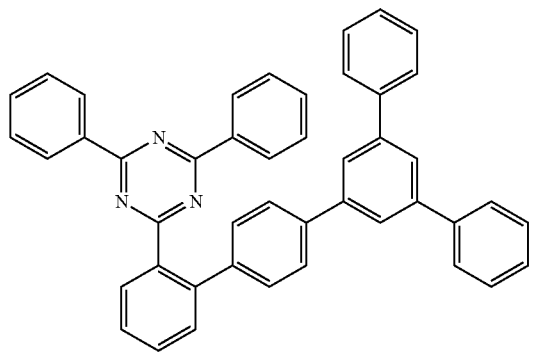

For the organic light emitting devices of Examples 1 to 15 and Comparative Examples 1 to 7, the driving voltage and the light emitting efficiency were measured at a current density of 10 mA/cm2, and a time (LT98) for reaching a 98% value compared to the initial luminance was measured at a current density of 20 mA/cm2. The results are shown in the following Table 1.

TABLE 1

| Example 10 mA/cm² | Compound | Voltage (V) | Current efficiency (cd/A) | Color coordinate (x, y) | Life Time (98 at 20 mA/cm²) |
|---|---|---|---|---|---|
| Example 1 | 1-3 | 3.84 | 5.19 | (0.137, 0.127) | 41 |
| Example 2 | 1-4 | 3.76 | 5.30 | (0.137, 0.127) | 39 |
| Example 3 | 1-16 | 3.81 | 5.27 | (0.138, 0.127) | 42 |
| Example 4 | 2-31 | 3.79 | 5.41 | (0.137, 0.126) | 40 |
| Example 5 | 3-33 | 3.83 | 5.42 | (0.136, 0.127) | 44 |
| Example 6 | 3-34 | 3.81 | 5.45 | (0.136, 0.126) | 46 |
| Example 7 | 3-36 | 3.83 | 5.42 | (0.136, 0.126) | 45 |
| Example 8 | 3-38 | 3.81 | 5.46 | (0.136, 0.127) | 48 |
| Example 9 | 3-39 | 3.82 | 5.45 | (0.136, 0.126) | 41 |
| Example 10 | 3-47 | 3.84 | 5.27 | (0.137, 0.127) | 39 |
| Example 11 | 4-12 | 3.91 | 5.19 | (0.137, 0.127) | 40 |
| Example 12 | 5-28 | 3.90 | 5.21 | (0.136, 0.127) | 39 |
| Example 13 | 3-48 | 3.89 | 5.19 | (0.137, 0.126) | 43 |
| Example 14 | 3-50 | 3.85 | 5.25 | (0.137, 0.127) | 42 |
| Example 15 | 1-17 | 3.90 | 5.24 | (0.136, 0.127) | 40 |
| Comparative Example 1 | ET 1 | 4.13 | 4.89 | (0.140, 0.129) | 26 |
| Comparative Example 2 | ET 2 | 4.07 | 5.11 | (0.139, 0.130) | 20 |
| Comparative Example 3 | ET 3 | 4.02 | 5.18 | (0.139, 0.130) | 21 |
| Comparative Example 4 | ET 4 | 3.96 | 5.02 | (0.140, 0.130) | 19 |
| Comparative Example 5 | ET 5 | 4.05 | 4.99 | (0.139, 0.130) | 22 |
| Comparative Example 6 | ET 6 | 4.01 | 4.98 | (0.139, 0.130) | 23 |
| Comparative Example 7 | ET 7 | 4.02 | 4.90 | (0.139, 0.130) | 21 |

In Table 1, it could be seen that the compounds in Examples 1 to 15 where the compound of Chemical Formula 1 according to an exemplary embodiment of the present specification was used as an electron transport layer of an organic light emitting device had low driving voltage, high current efficiency, and a long lifetime compared to the compounds in Comparative Examples 1 to 7. In particular, it could be seen that in Chemical Formula 1 according to an exemplary embodiment of the present specification, the compounds in Examples 1 to 15, which are prepared by using a heterocyclic group (Har) except for an aryl group in which Ar3 is fused (fused Ar) or pyridine, quinoline, and the like, had low driving voltage, high current efficiency, and a long lifetime compared to the compounds in Comparative Examples 2 and 3 in which triazine is linked to Ar3 through pyridine and quinoline as in ET2 and ET3.

The invention claimed is:

1. A compound represented by the following Chemical Formula 1:

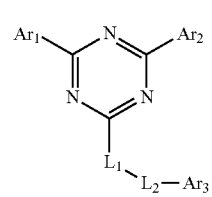

[Chemical Formula 1]

in Chemical Formula 1,

Ar$_1$ and Ar$_2$ are the same as or different from each other, and are each independently a substituted or unsubstituted aryl group; or a substituted or unsubstituted heterocyclic group, L$_1$ is represented by Chemical Formulae 2 or 5,

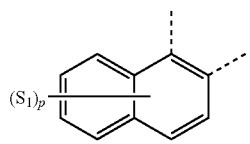

[Chemical Formula 2]

S$_1$ is deuterium; a halogen group; a substituted or unsubstituted alkyl group; a substituted or unsubstituted aryl group; or a substituted or unsubstituted heterocyclic group, p is an integer of 0 to 6, and when p is an integer of 2 or more, each occurrence of S$_1$ is the same as or different from each other,

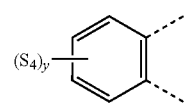

[Chemical Formula 5]

S₄ is deuterium; a halogen group; a substituted or unsubstituted alkyl group; a substituted or unsubstituted aryl group; or a substituted or unsubstituted heterocyclic group, y is an integer of 0 to 4, and when y is an integer of 2 or more, each occurrence of S₄ is each the same as or different from each other, in Chemical Formulae 2 and 5, a dotted line "- - - - -" is each a moiety bonded to a triazine group or L₂ of Chemical Formula 1, L₂ is a direct bond; or a substituted or unsubstituted arylene group, and Ar₃ is represented by a substituted phenyl group; a substituted or unsubstituted fluorenyl group; a substituted or unsubstituted benzofluorenyl group; a substituted or unsubstituted spirobifluorenyl group; a substituted or unsubstituted spirofluoreneindenophenanthrene group; a substituted or unsubstituted dispirofluoreneanthracenefluorene group; a substituted or unsubstituted triphenylene group; a heterocyclic group including S or O, which is unsubstituted or substituted; an unsubstituted carbazole group; or any one of the following Chemical Formulae 6 to 9, 10-1 and 10-2, when L₁ is Chemical Formula 2, provided that the compound is not

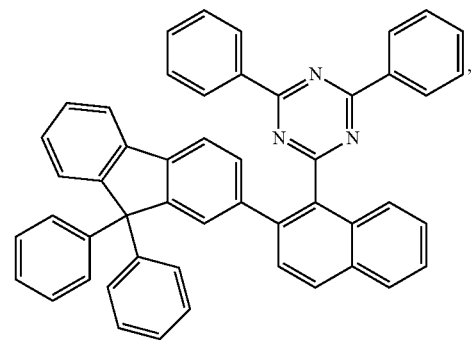,

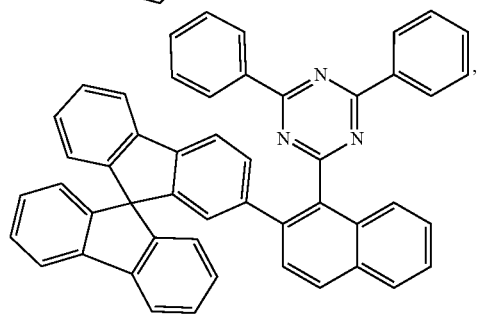,

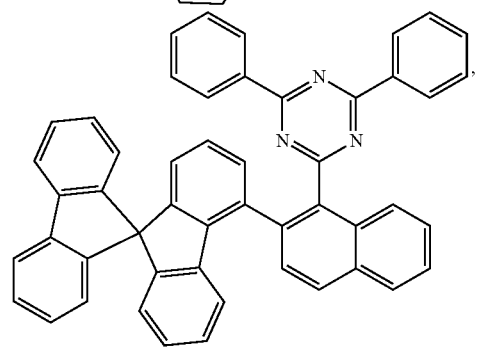 or

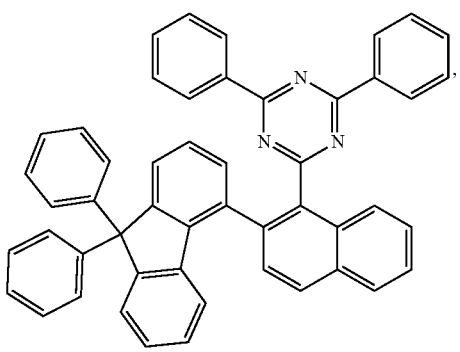, and provided that when Ar₃ is a fluorenyl substituted with an alkyl group, L₂ is a substituted or unsubstituted arylene group, Ar₃ is represented by a cyano-substituted phenyl group; a substituted or unsubstituted fluorenyl group, wherein adjacent substituents of the fluorenyl group do not combine with each other to form a ring; a substituted or unsubstituted benzofluorenyl group; a substituted spirobifluorenyl group, wherein the substitutions of spirobifluorenyl group do not combine with each other to form a 5-membered to 8-membered hetero ring; a substituted or unsubstituted spirofluoreneindenophenanthrene group; a substituted or unsubstituted dispirofluoreneanthracenefluorene group; an unsubstituted dibenzofuran group; an unsubstituted dibenzothiophene group; a substituted or unsubstituted benzonaphthofuran group; a substituted or unsubstituted benzonaphthothiophene group; or any one of Chemical Formulae 6, 9, 10-1 and 10-2, when L₁ is Chemical Formula 5,

[Chemical Formula 6]

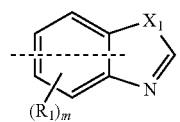

[Chemical Formula 7]

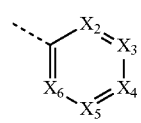

[Chemical Formula 8]

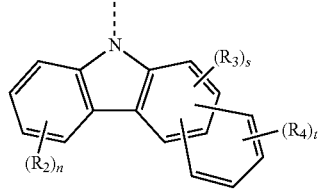

[Chemical Formula 9]

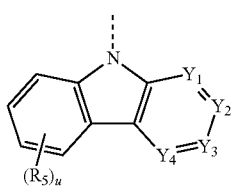

[Chemical Formula 10-1]

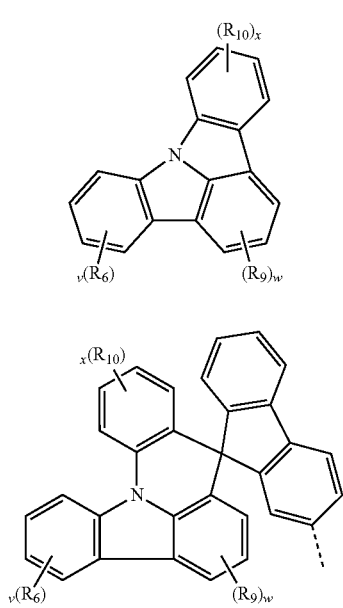

[Chemical Formula 10-2]

in Chemical Formulae 6 to 9, 10-1 and 10-2, $X_1$ is O, S, or NR, at least two of $X_2$ to $X_6$ are N, and the others are each independently CR', R and R' are each independently hydrogen; deuterium; a halogen group; a substituted or unsubstituted alkyl group; or a substituted or unsubstituted aryl group, $R_1$ to $R_6$, $R_9$, and $R_{10}$ are each independently deuterium; a halogen group; a substituted or unsubstituted alkyl group; a substituted or unsubstituted aryl group; or a substituted or unsubstituted heterocyclic group, at least one of $Y_1$ to $Y_4$ is N, and the others are CR", R" is each independently hydrogen or deuterium, m, n, t, u, v, and x are each independently an integer of 0 to 4, w is an integer of 0 to 3, and when m, n, t, u, v, w, and x are each an integer of 2 or more, $R_1$ to $R_6$, $R_9$, and $R_{10}$ in each occurrence are the same as or different from each other, respectively, s is an integer of 0 to 2, and when s is 2, two $R_3$s are the same as or different from each other, and "- - - - -" means a moiety bonded to $L_2$ of Chemical Formula 1, and the bonding moiety of Chemical Formula 10-1 is R6, R9, or R10.

2. The compound of claim 1, wherein $L_2$ is a direct bond; or a substituted or unsubstituted $C_6$ to $C_{20}$ arylene group.

3. The compound of claim 1, wherein $Ar_3$ is a substituted phenyl group; a substituted or unsubstituted fluorenyl group; a substituted or unsubstituted benzofluorenyl group; a substituted or unsubstituted spirobifluorenyl group; a substituted or unsubstituted spirofluoreneindenophenanthrene group; a substituted or unsubstituted dispirofluoreneanthracenefluorene group; a substituted or unsubstituted triphenylene group; a substituted or unsubstituted pyrimidyl group; a substituted or unsubstituted pyridazinyl group; a substituted or unsubstituted triazinyl group; a substituted or unsubstituted benzocarbazolyl group; a substituted or unsubstituted benzimidazole group; a substituted or unsubstituted benzoxazole group; a substituted or unsubstituted benzothiazole group; a substituted or unsubstituted dibenzofuran group; a substituted or unsubstituted dibenzothiophene group; a substituted or unsubstituted benzonaphthofuran group; or a substituted or unsubstituted benzonaphthothiophene group, when $L_1$ is Chemical Formula 2, provided that the compound is not

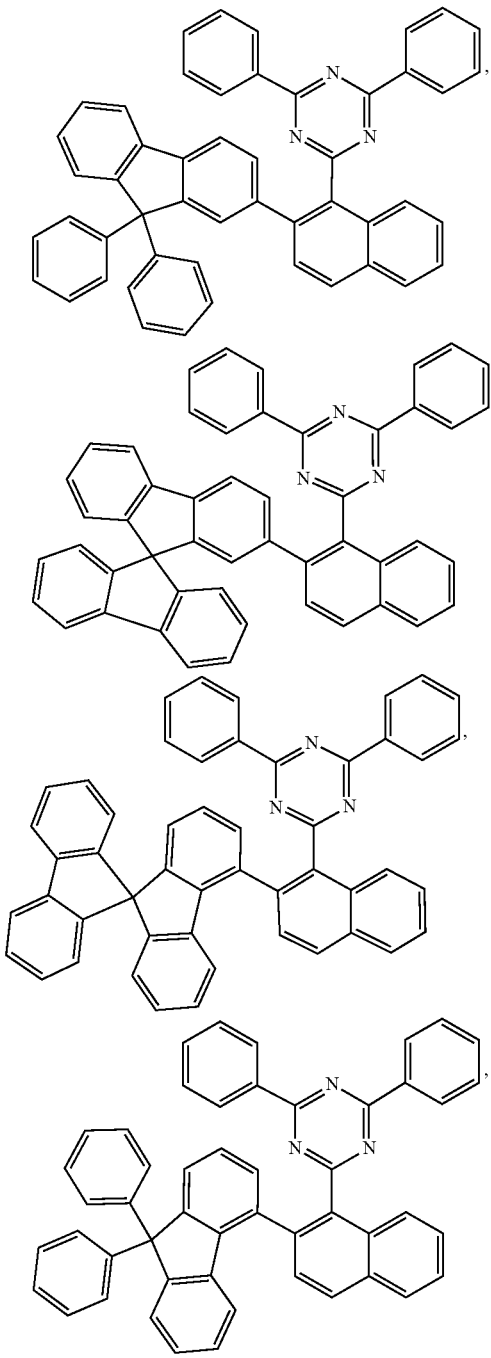

and $Ar_3$ is a cyano-substituted phenyl group; a substituted or unsubstituted fluorenyl group, wherein adjacent substituents of the fluorenyl group do not combine with each other to form a ring; a substituted or unsubstituted benzofluorenyl group; a substituted spirobifluorenyl group; a substituted or unsubstituted spirofluoreneindenophenanthrene group; a substituted or unsubstituted dispirofluoreneanthracenefluorene group; a substituted or unsubstituted benzimidazole group; a substituted or unsubstituted benzoxazole group; a substituted or unsubstituted benzothiazole group; an unsubstituted dibenzofuran group; an unsubstituted dibenzothiophene group; a substituted or unsubstituted benzonaphthofuran group; or a substituted or unsubstituted benzonaphthothiophene group, when $L_1$ is Chemical Formula 5.

4. The compound of claim 1, wherein $Ar_1$ and $Ar_2$ are the same as or different from each other, and are each independently a substituted or unsubstituted $C_6$ to $C_{20}$ aryl group.

5. A compound represented by the following structural formulae:

Compound 1-1

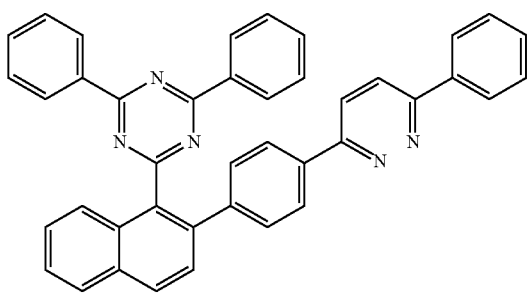

Compound 1-2

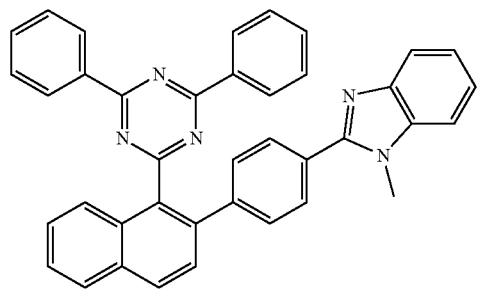

Compound 1-3

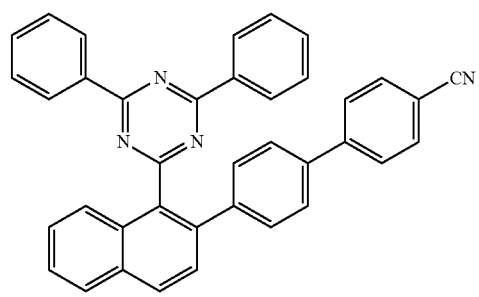

Compound 1-4

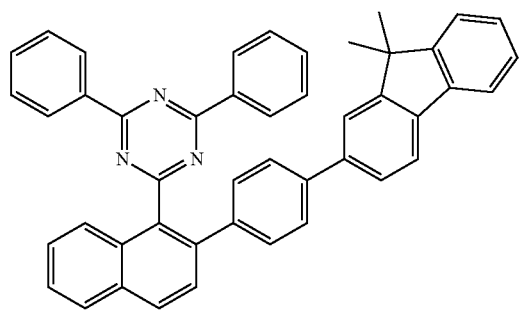

-continued

Compound 1-5

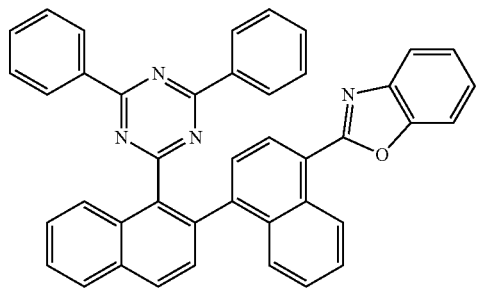

Compound 1-6

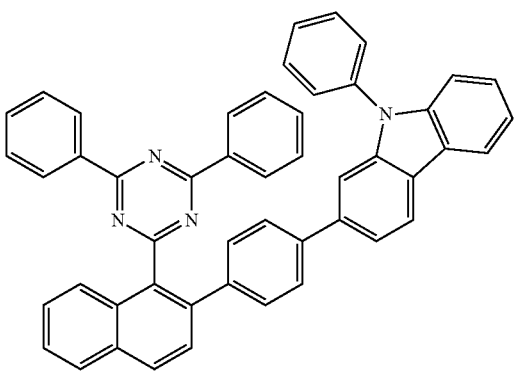

Compound 1-7

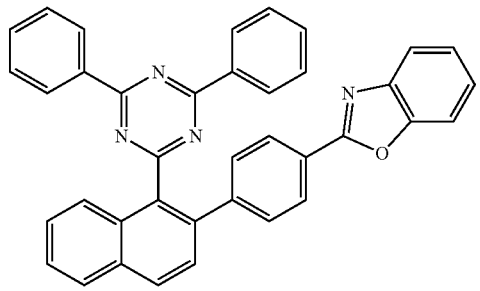

Compound 1-8

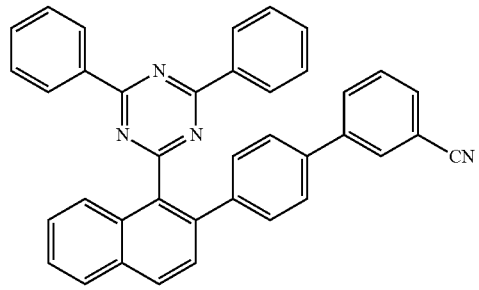

Compound 1-9
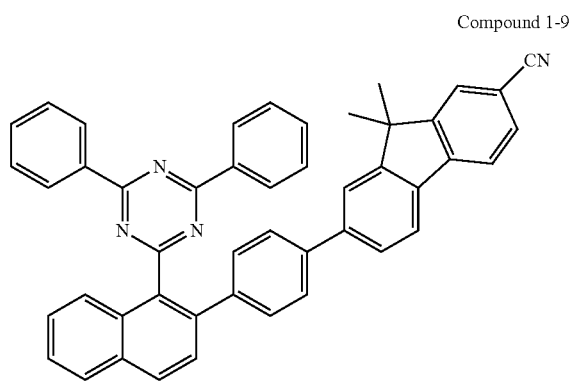
Compound 1-10
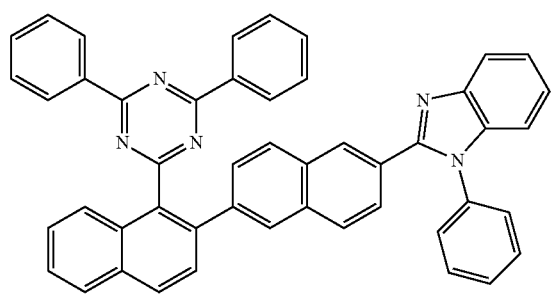
Compound 1-11
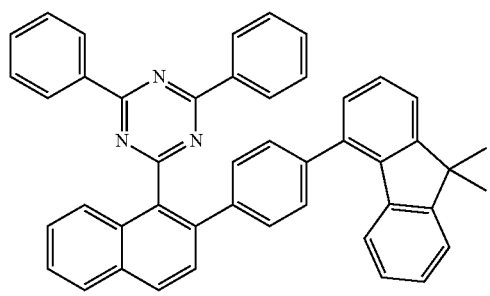
Compound 1-12
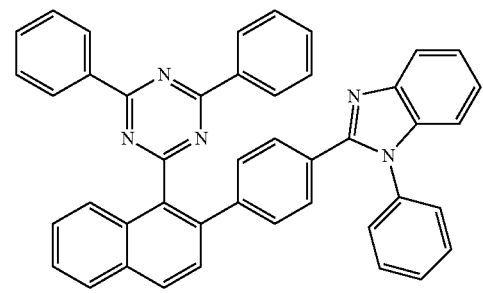
Compound 1-13
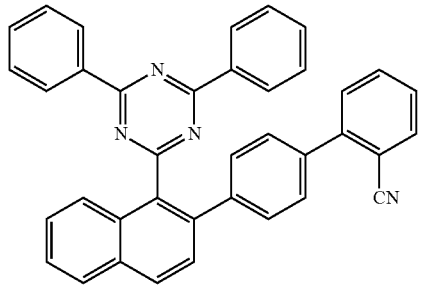
Compound 1-14
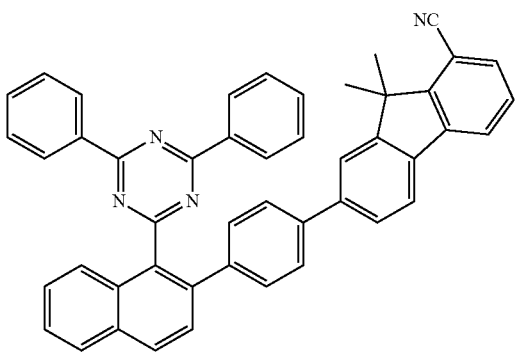
Compound 1-15
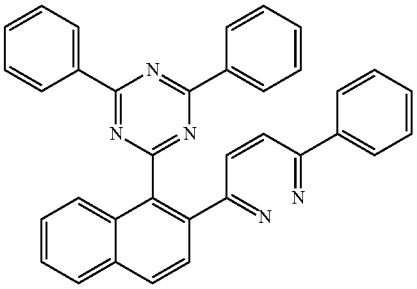
Compound 1-16
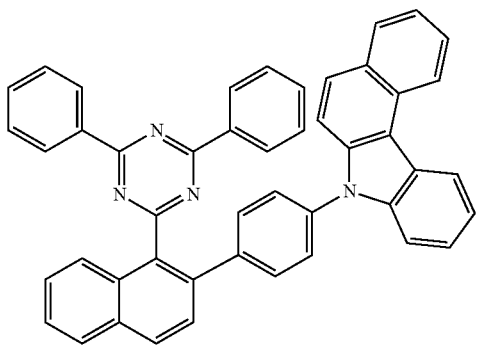
Compound 1-17
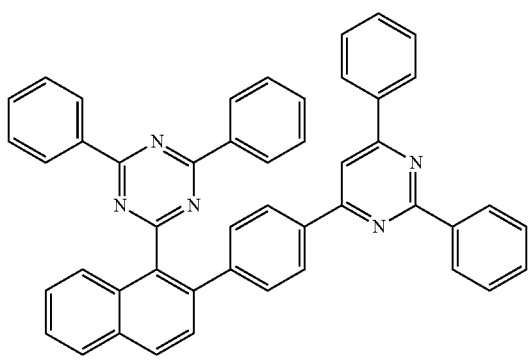

Compound 1-18
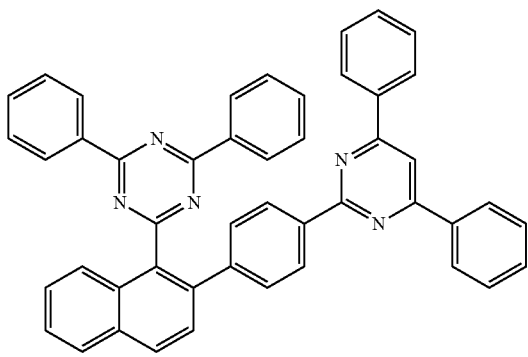
Compound 1-19
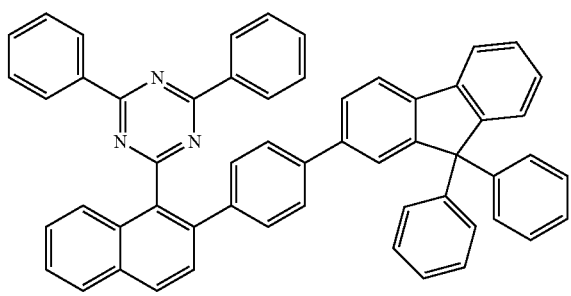
Compound 1-20
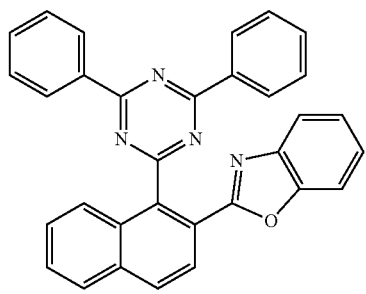
Compound 1-21
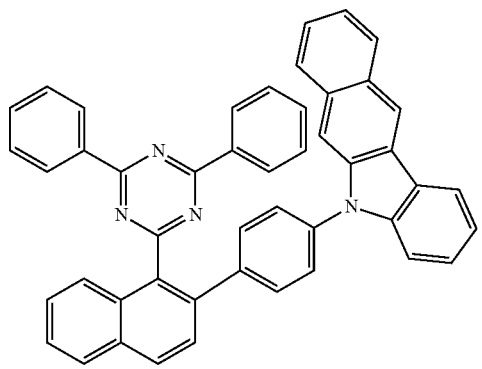
Compound 1-22
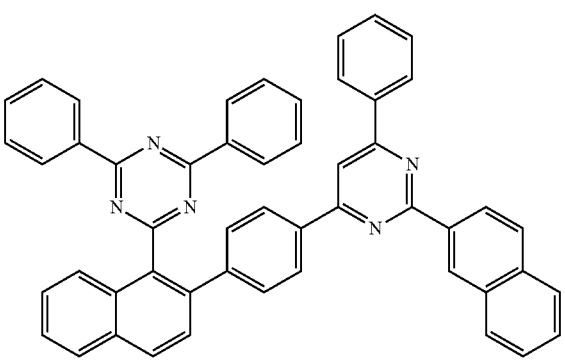
Compound 1-23
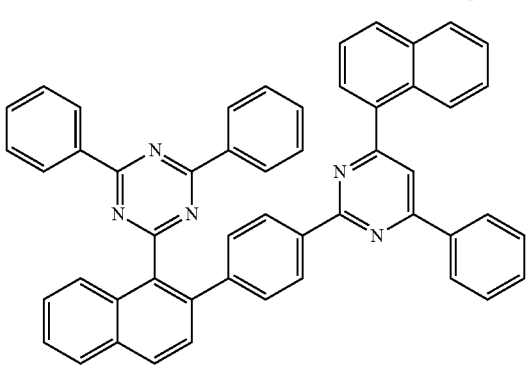
Compound 1-24
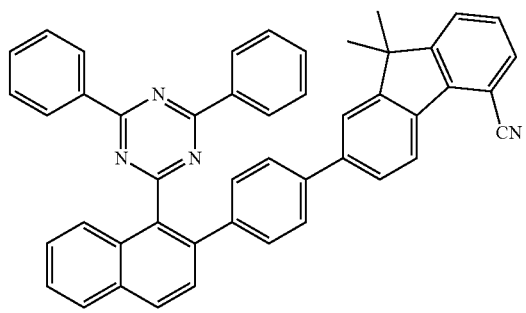
Compound 1-25
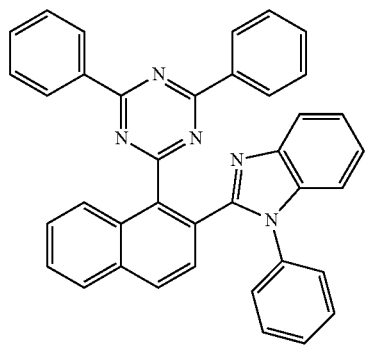

-continued
Compound 1-26
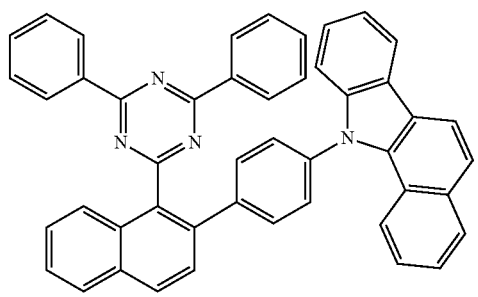
Compound 1-27
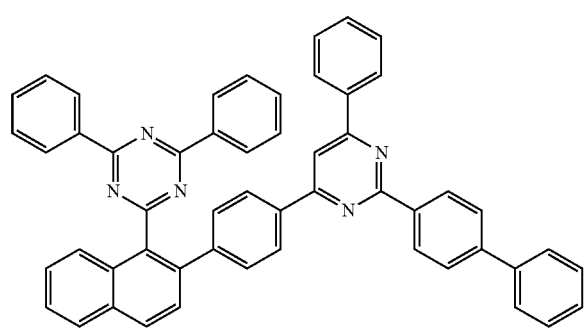
Compound 1-28
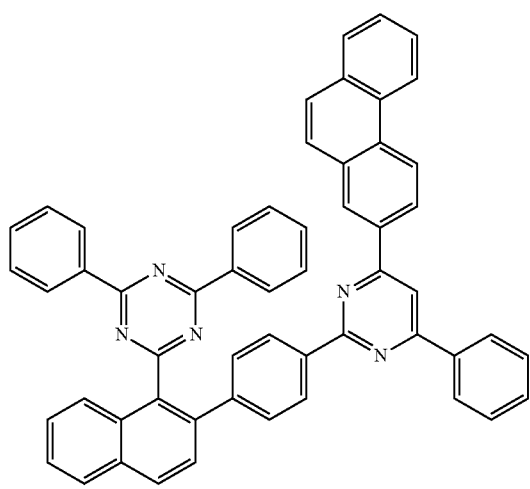
Compound 1-29
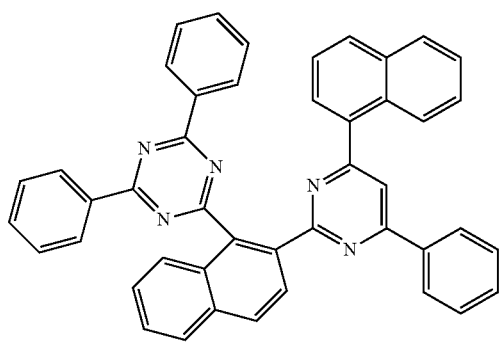
-continued
Compound 1-30
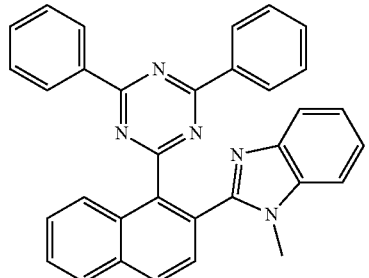
Compound 1-31
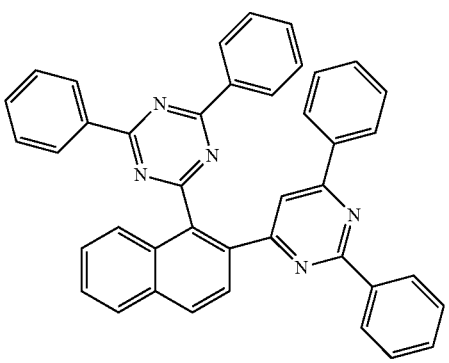
Compound 1-32
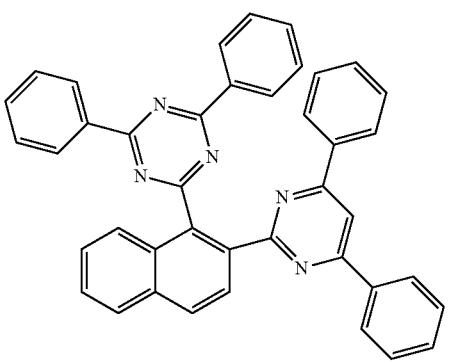
Compound 1-33
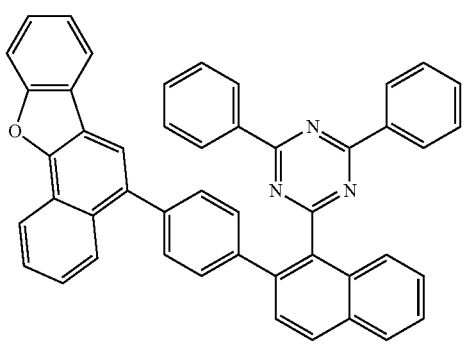

Compound 1-34
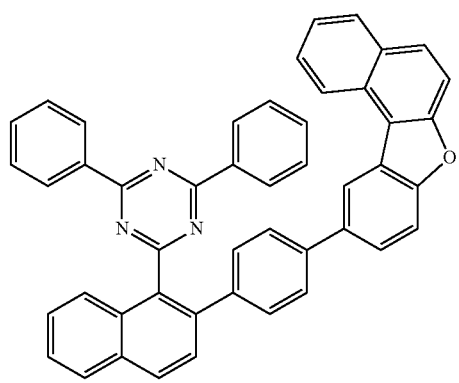
Compound 1-35
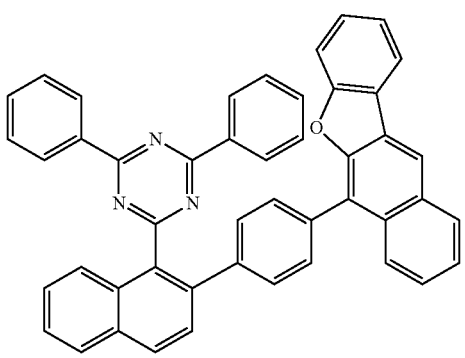
Compound 1-36
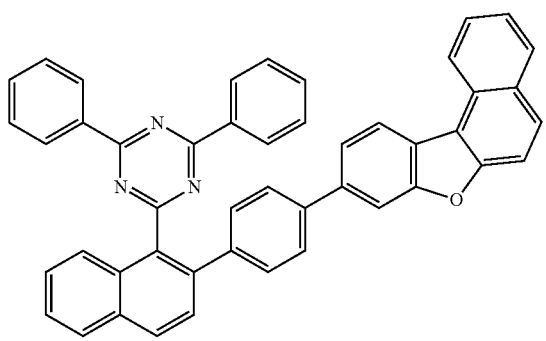
Compound 1-37
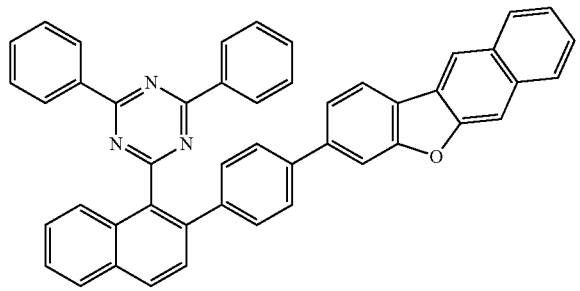
Compound 1-38
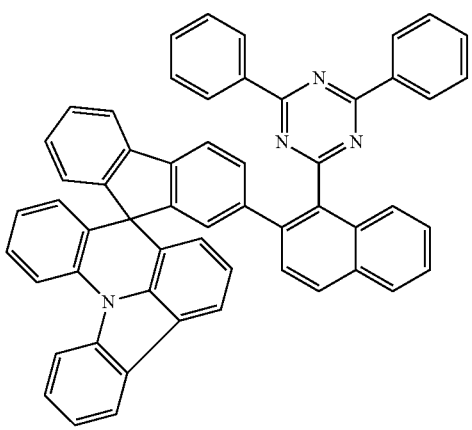
Compound 1-43
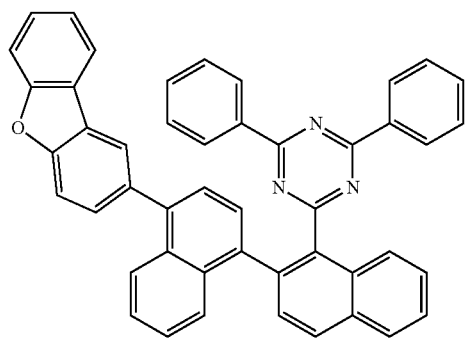
Compound 1-44
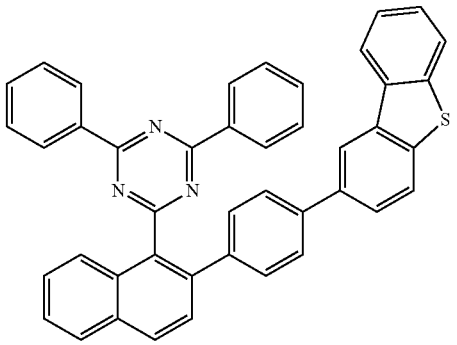
Compound 1-45
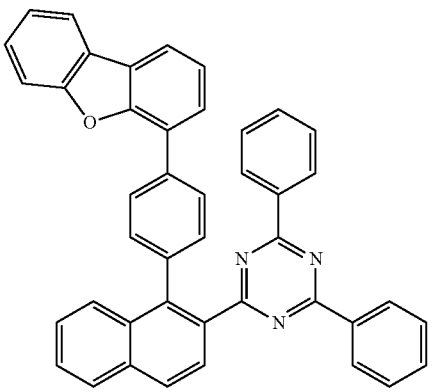

Compound 1-46
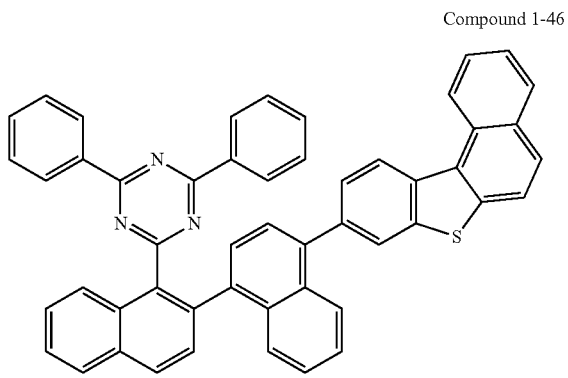
Compound 1-47
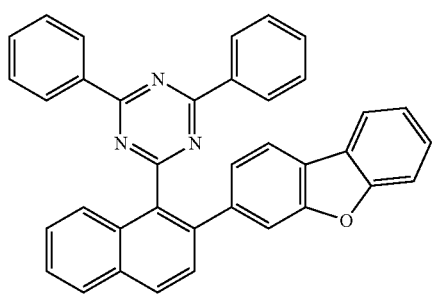
Compound 1-48
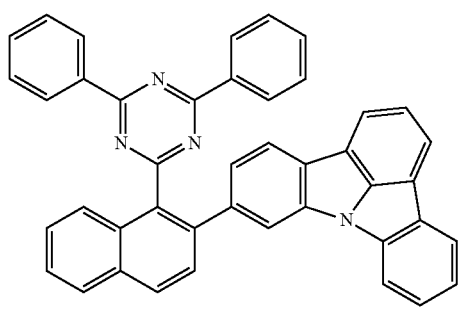
Compound 1-49
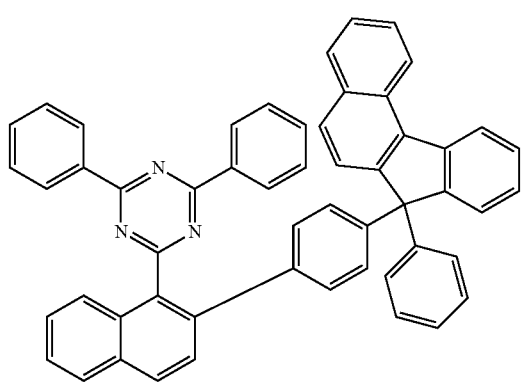
Compound 1-50
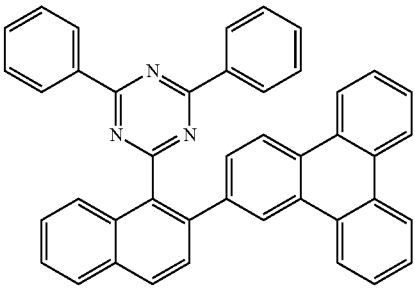
Compound 1-51
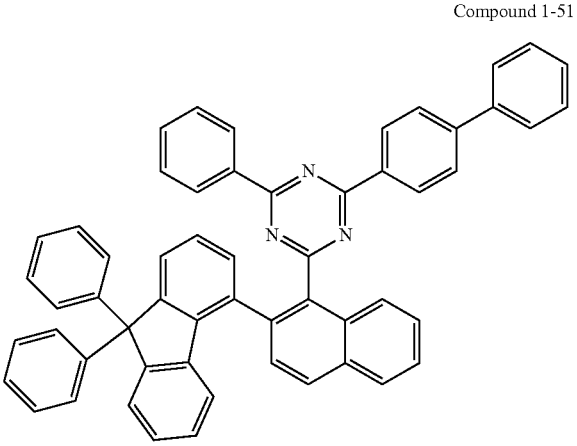
Compound 1-52
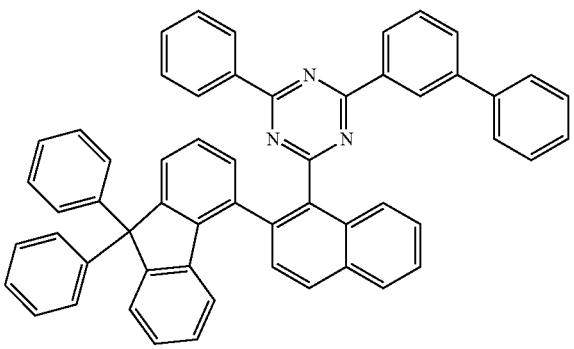
Compound 1-53
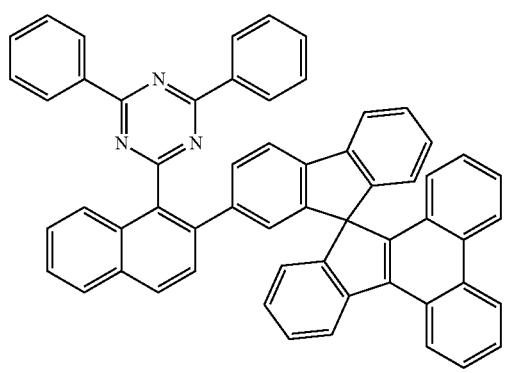

Compound 1-54
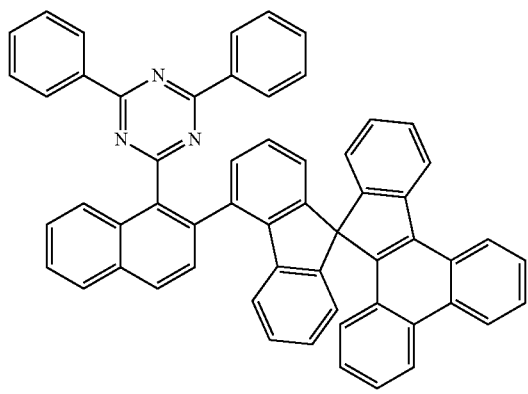
Compound 1-55
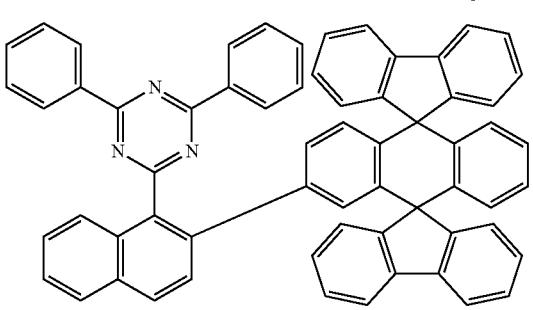
Compound 1-56
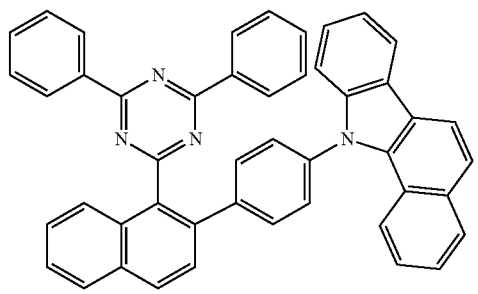
Compound 1-57
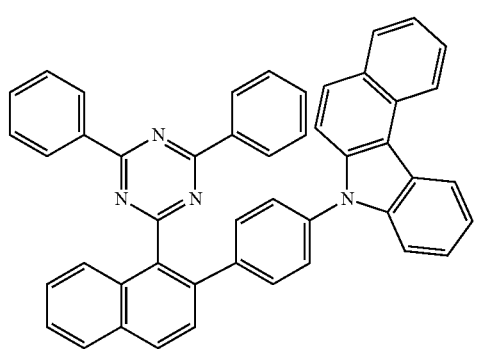
Compound 3-1
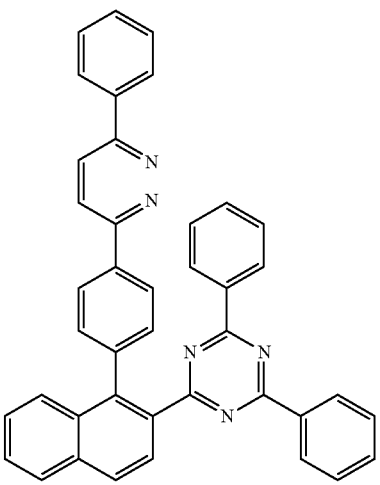
Compound 3-2
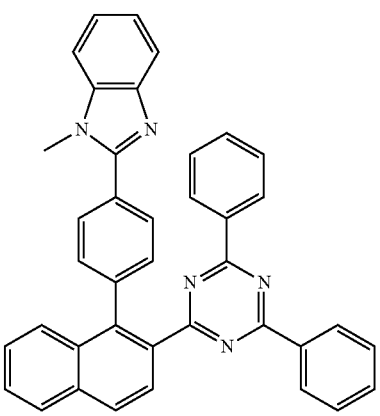
Compound 3-3
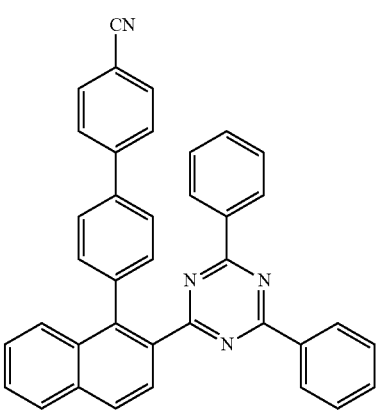

Compound 3-4
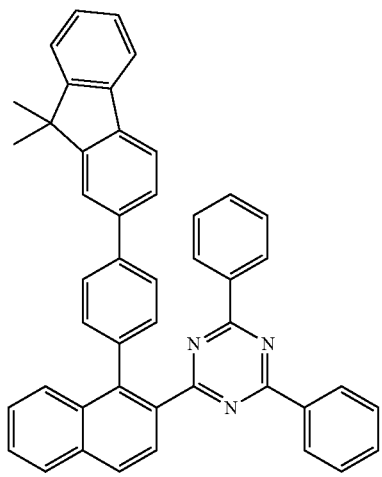
Compound 3-7
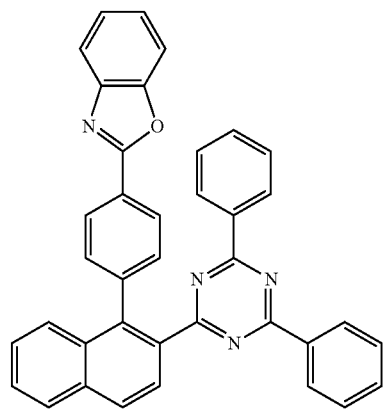
Compound 3-5
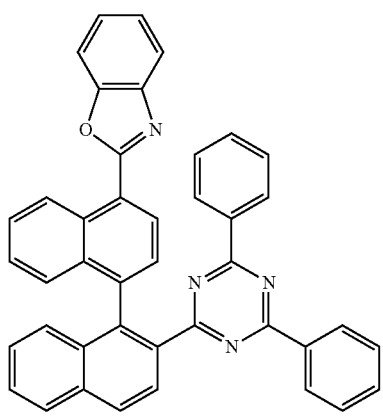
Compound 3-8
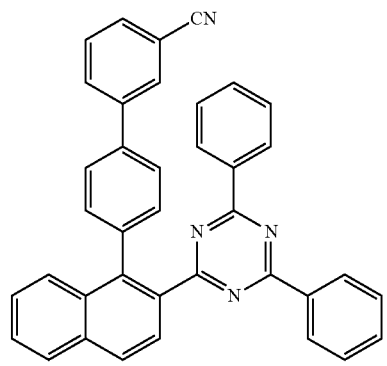
Compound 3-6
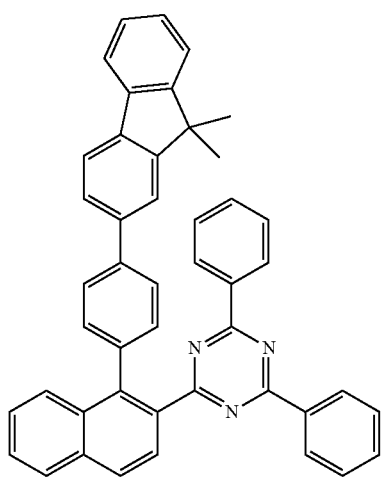
Compound 3-9
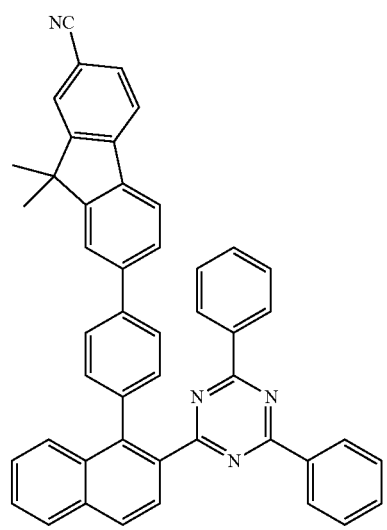

Compound 3-10
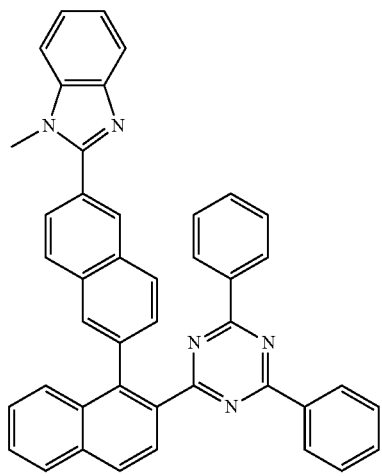
Compound 3-13
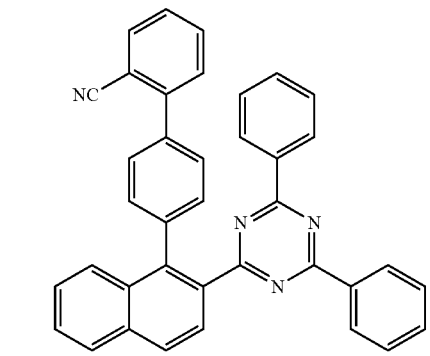
Compound 3-14
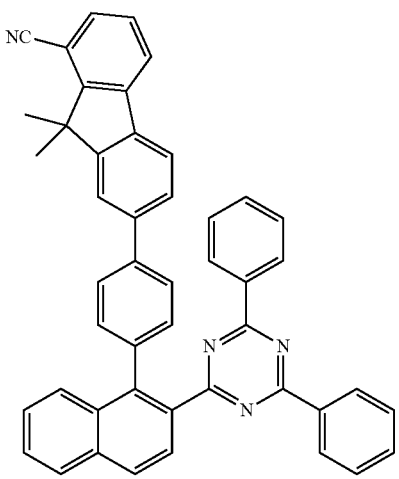
Compound 3-11
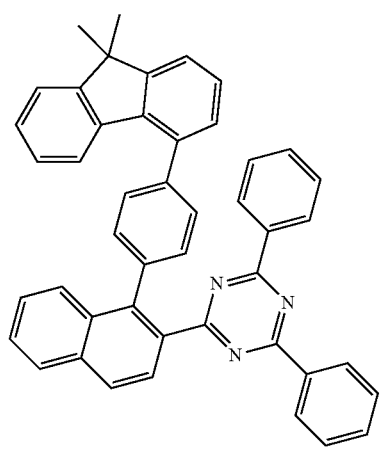
Compound 3-15
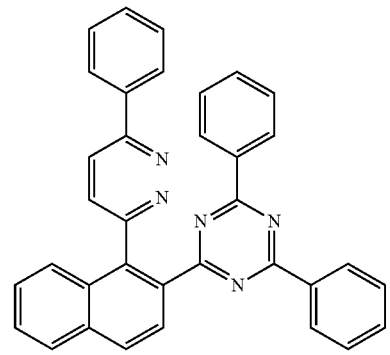
Compound 3-12
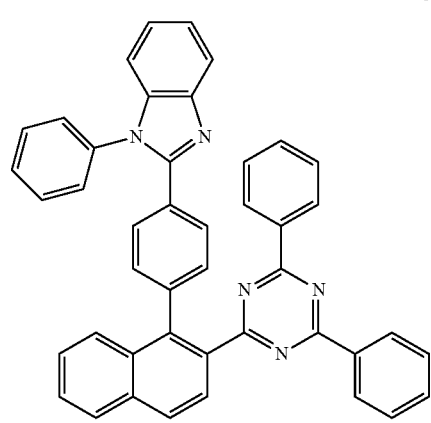
Compound 3-16
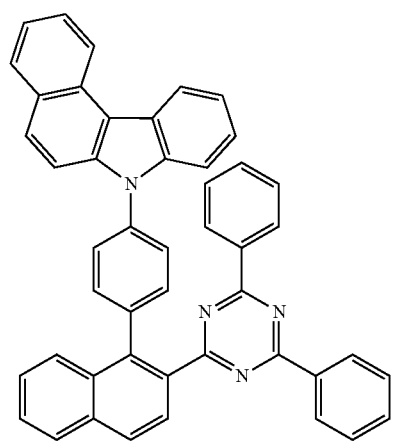

Compound 3-17
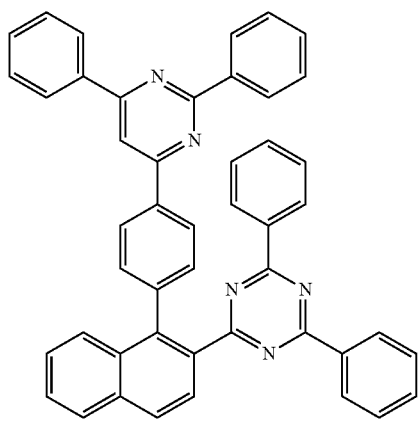
Compound 3-18
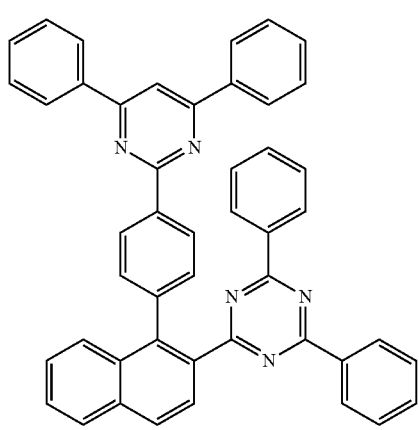
Compound 3-19
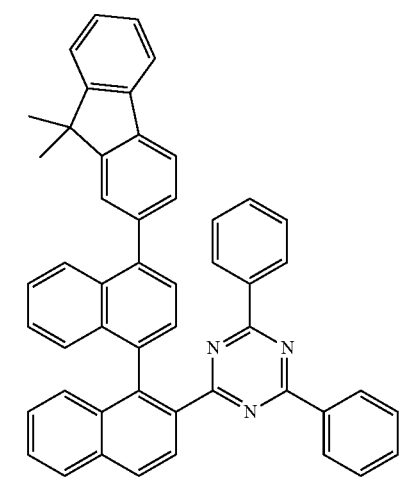
Compound 3-20
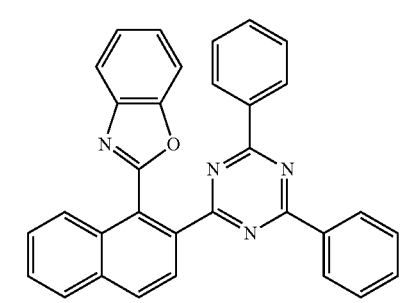
Compound 3-21
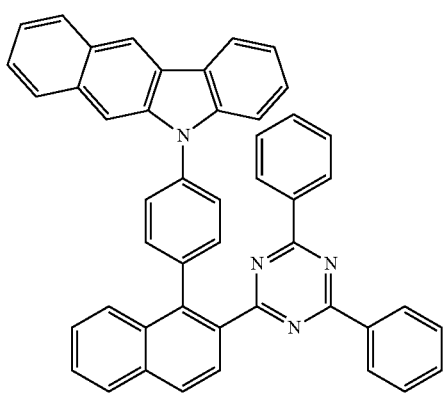
Compound 3-22
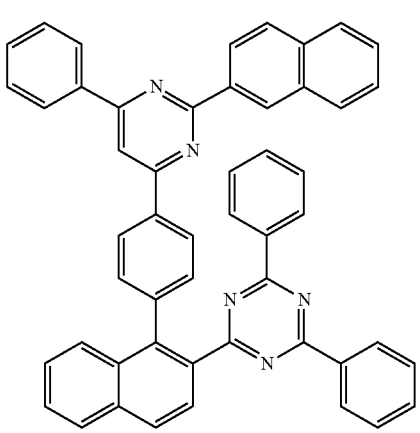
Compound 3-23
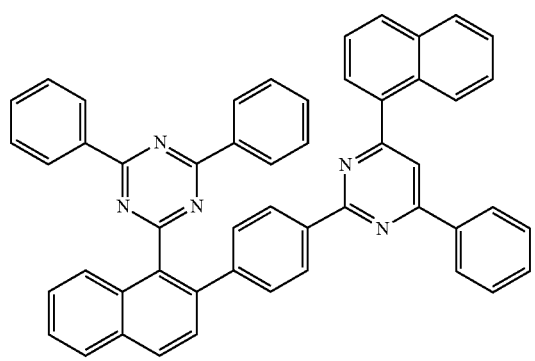

Compound 3-24
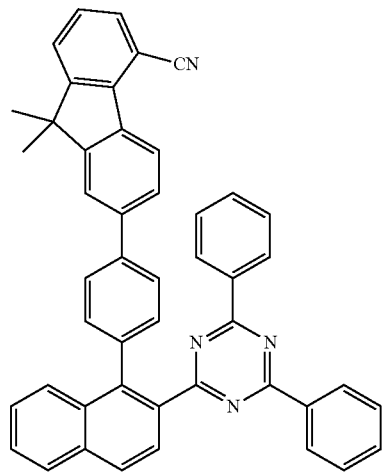
Compound 3-27
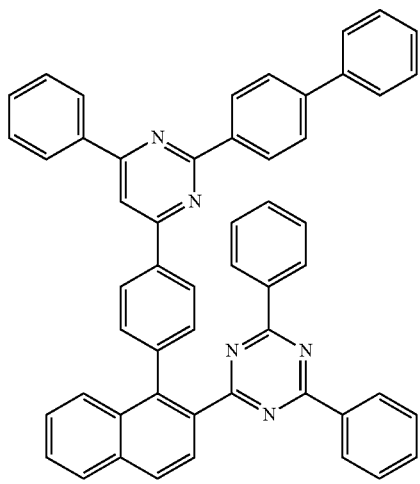
Compound 3-25
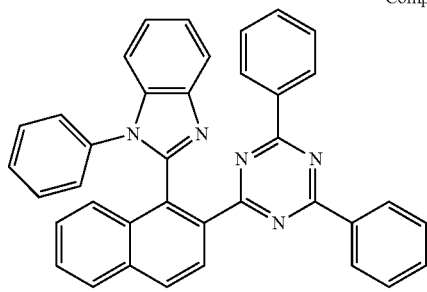
Compound 3-28
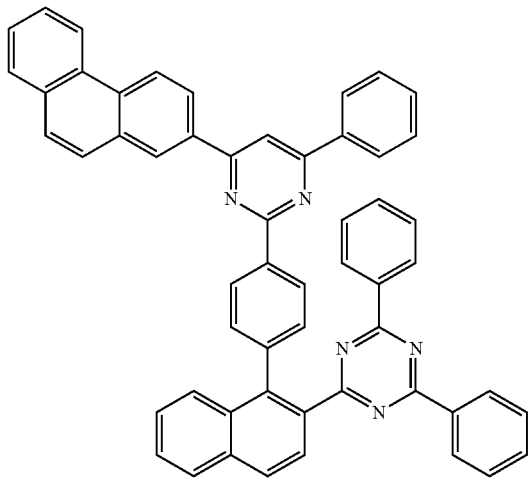
Compound 3-26
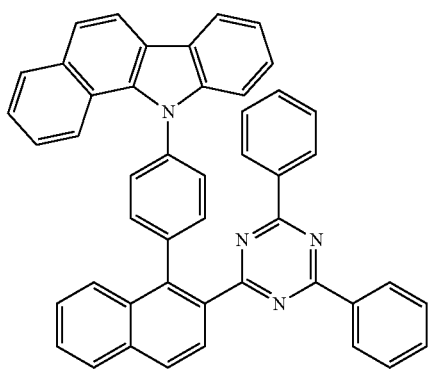
Compound 3-29
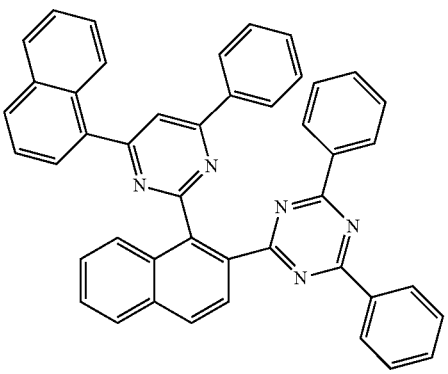

Compound 3-30
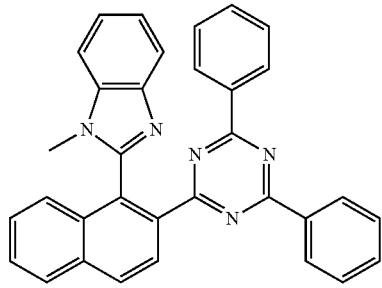
Compound 3-31
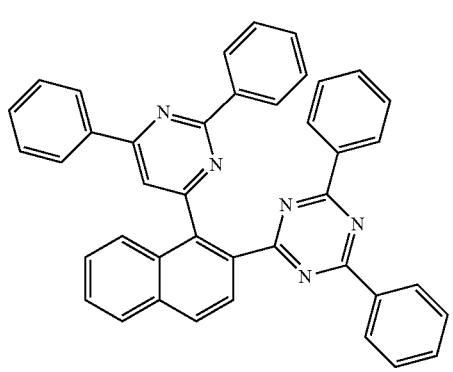
Compound 3-32
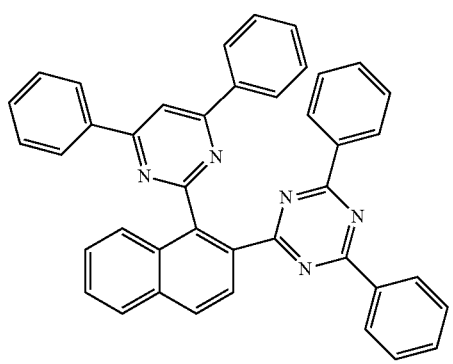
Compound 3-33
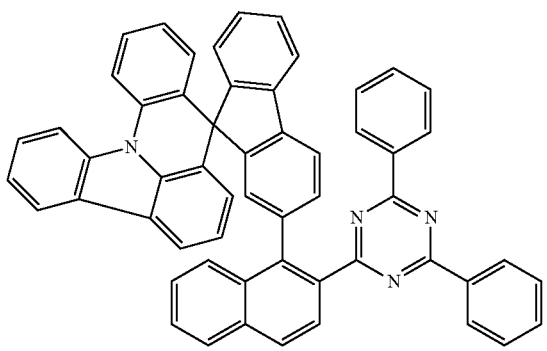
Compound 3-34
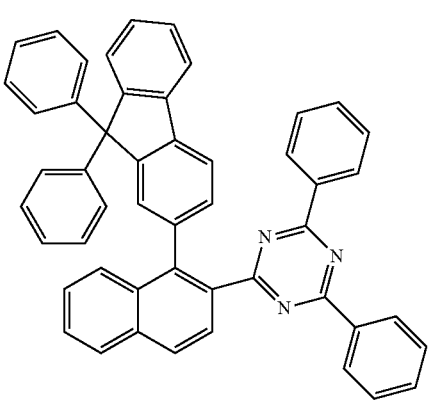
Compound 3-35
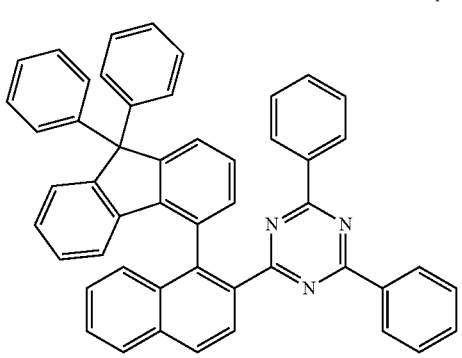
Compound 3-36
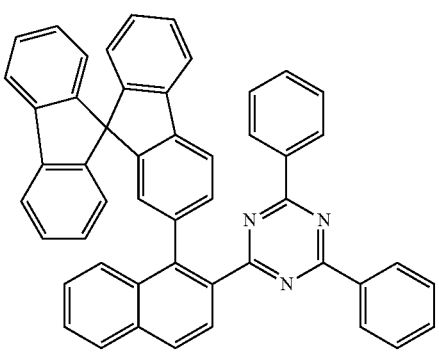
Compound 3-37
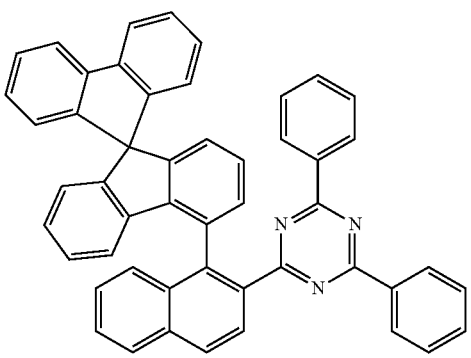

Compound 3-38
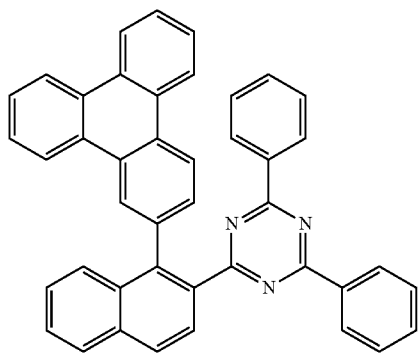
Compound 3-39
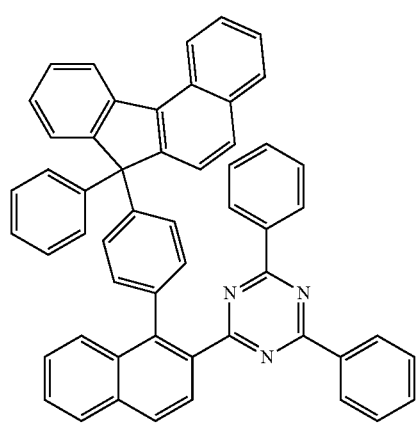
Compound 3-40
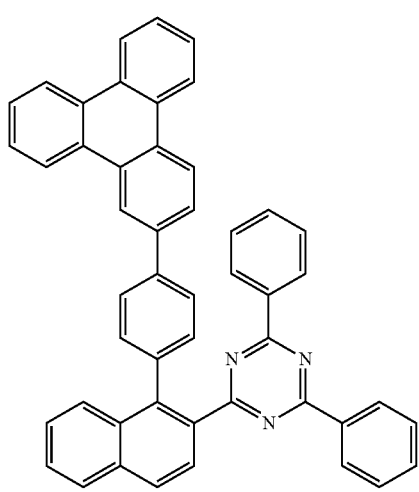
Compound 3-41
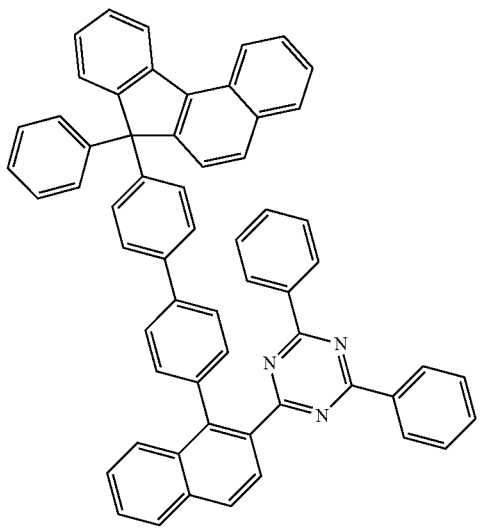
Compound 3-42
Compound 3-43
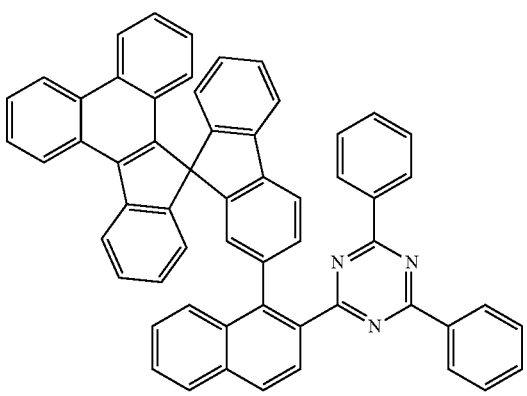

Compound 3-44

Compound 3-45

Compound 3-46

Compound 3-47

Compound 3-48

Compound 3-49

Compound 3-50
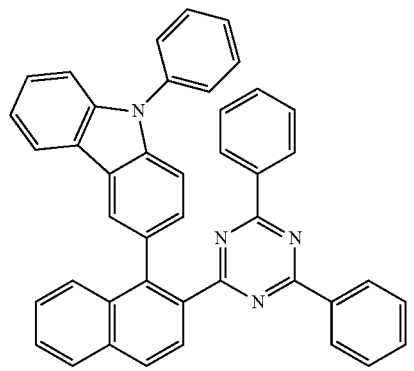
Compound 5-1
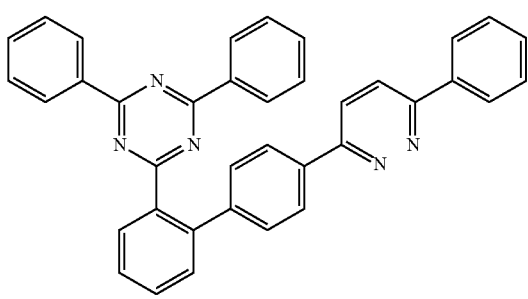
Compound 5-2
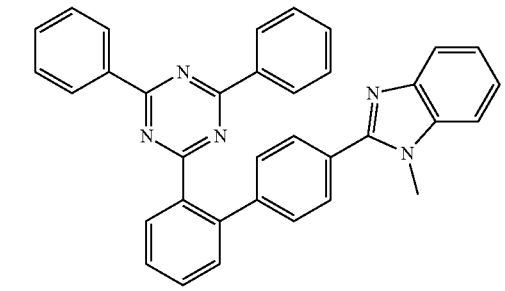
Compound 5-3
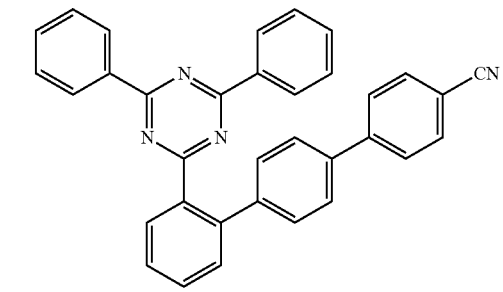
Compound 5-4
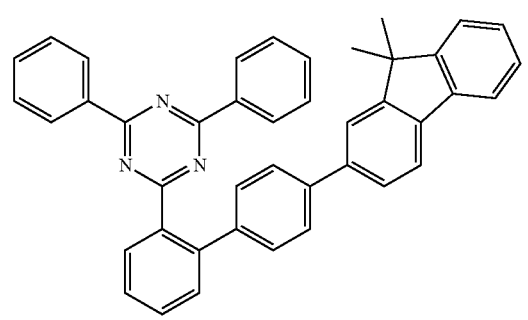
Compound 5-5
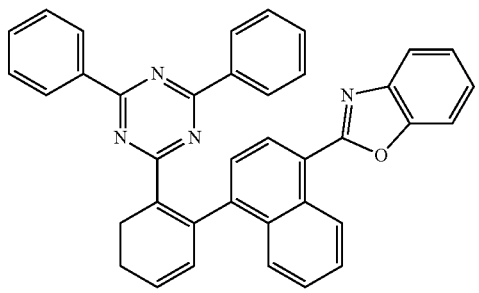
Compound 5-7
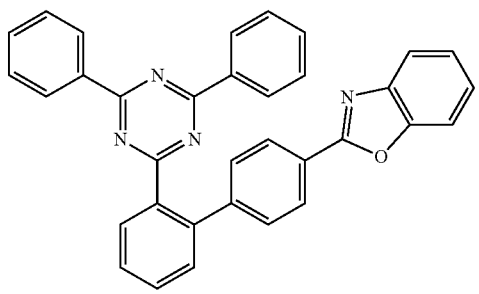
Compound 5-8
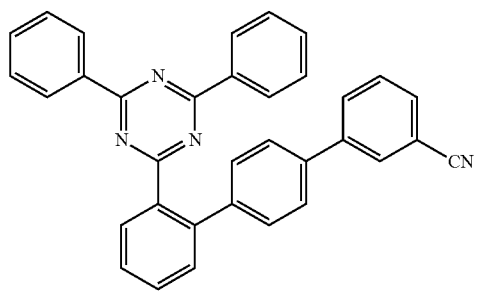
Compound 5-9
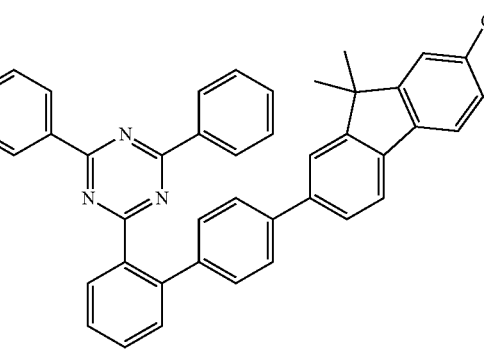
Compound 5-10
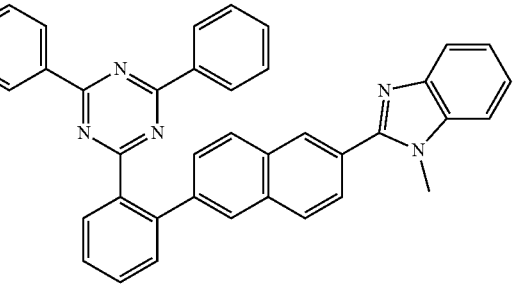

Compound 5-11
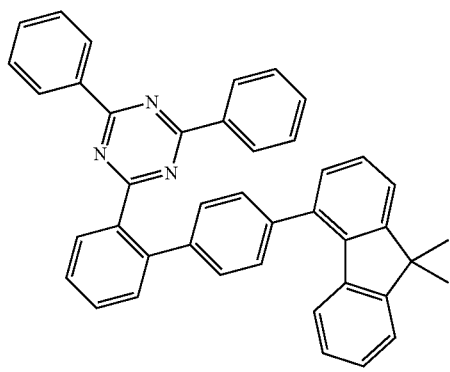
Compound 5-12
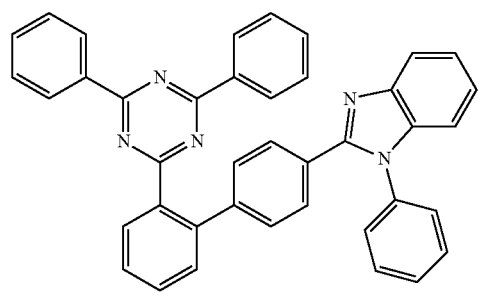
Compound 5-13
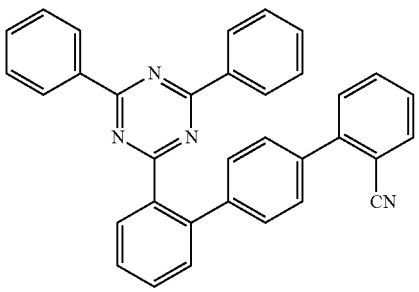
Compound 5-14
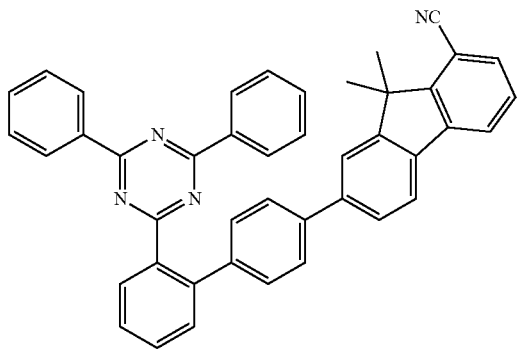
Compound 5-15
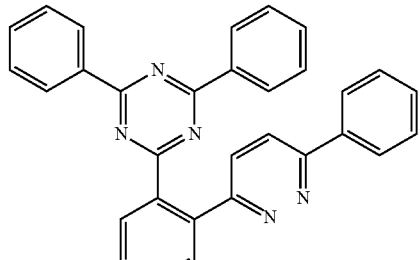
Compound 5-17
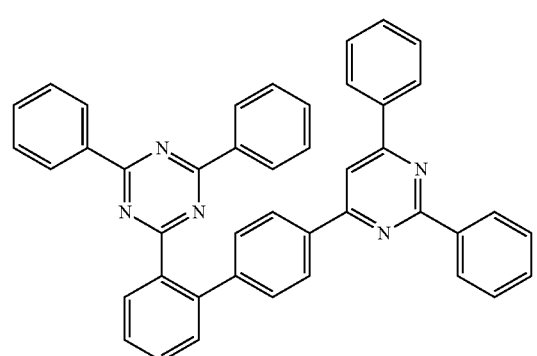
Compound 5-18
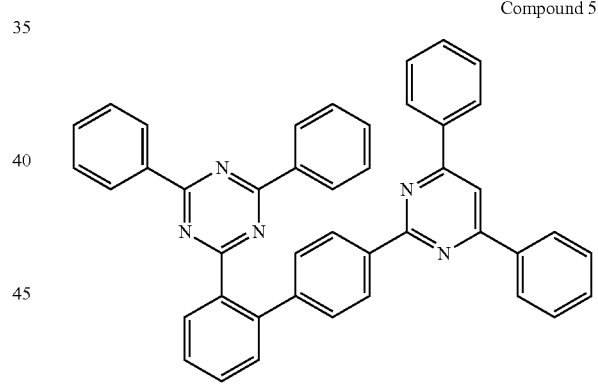
Compound 5-20
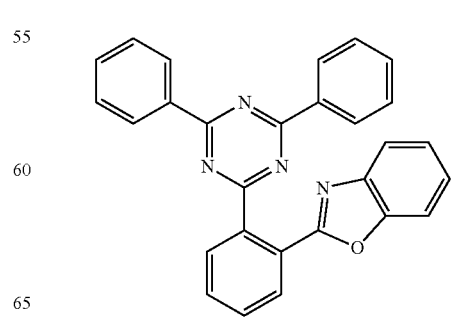

Compound 5-22
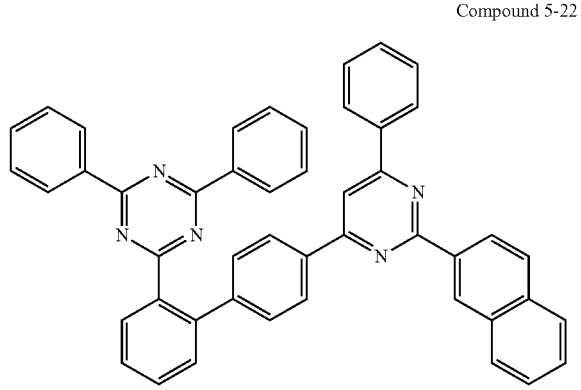
Compound 5-23
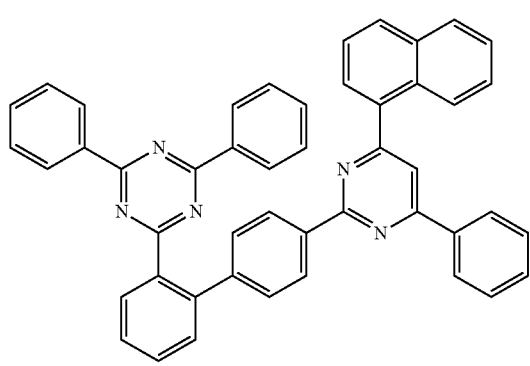
Compound 5-24
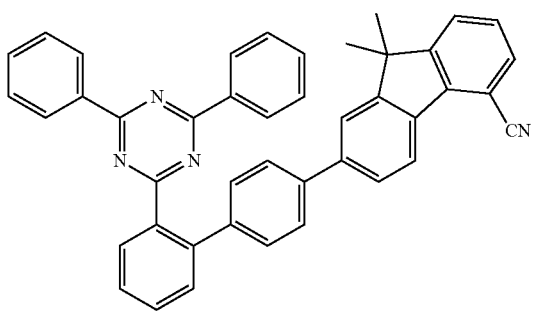
Compound 5-25
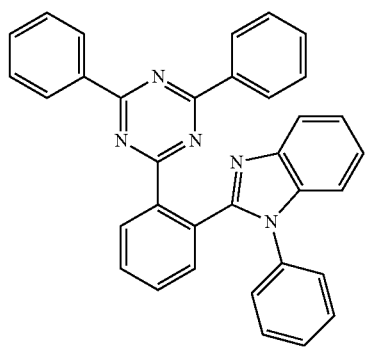
Compound 5-26
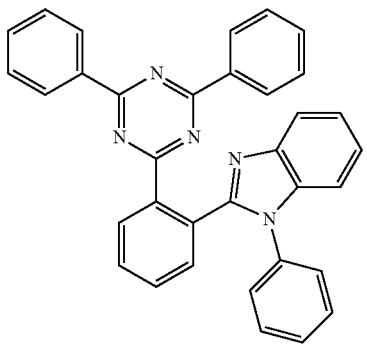
Compound 5-28
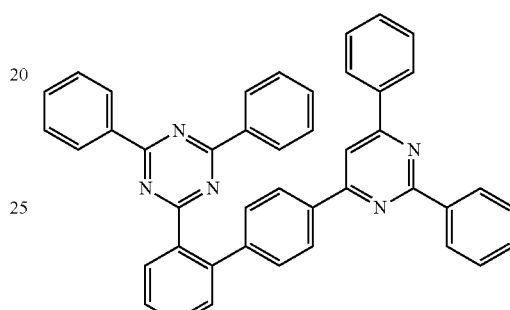
Compound 5-29
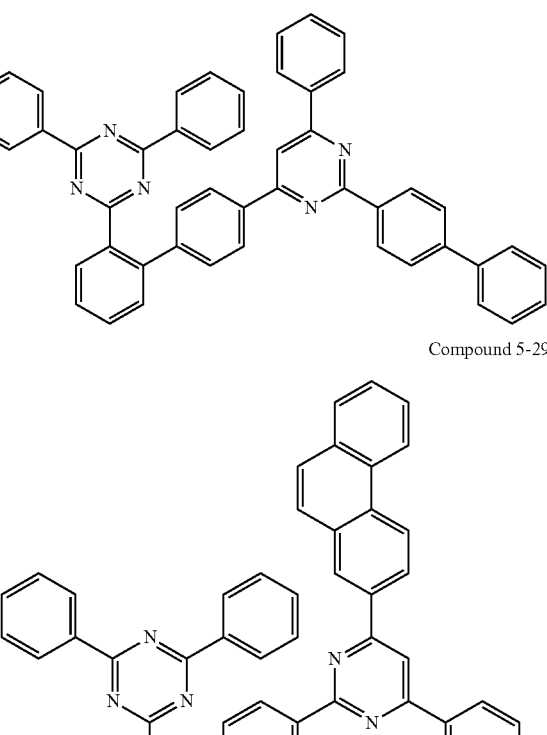
Compound 5-30
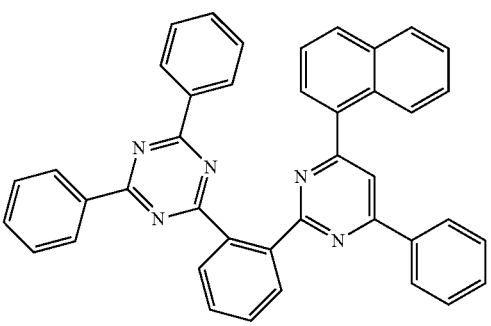

Compound 5-31
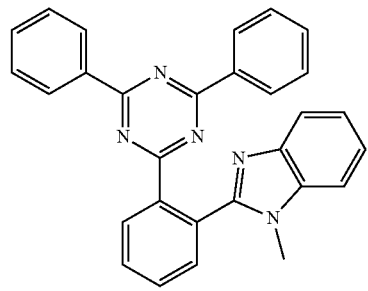
Compound 5-32
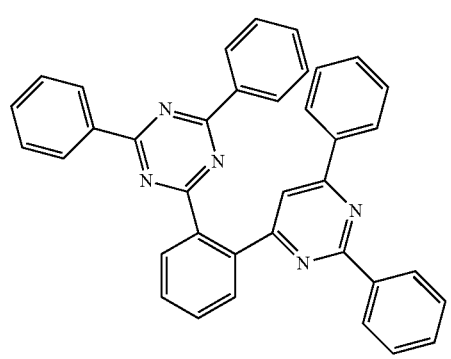
Compound 5-33
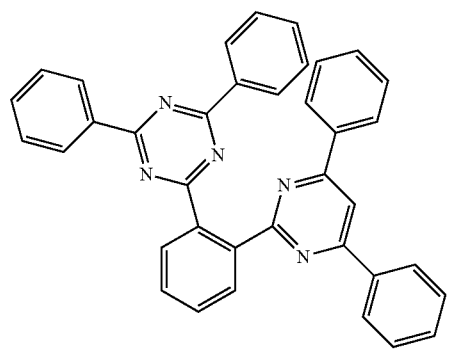
Compound 5-34
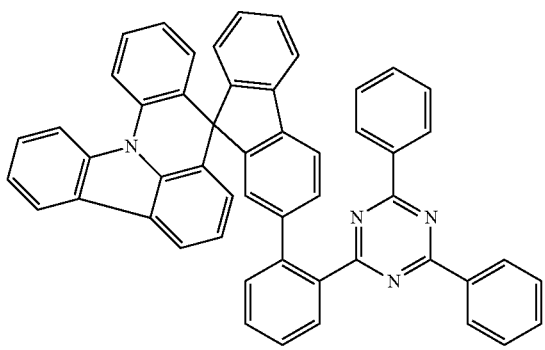
Compound 5-39
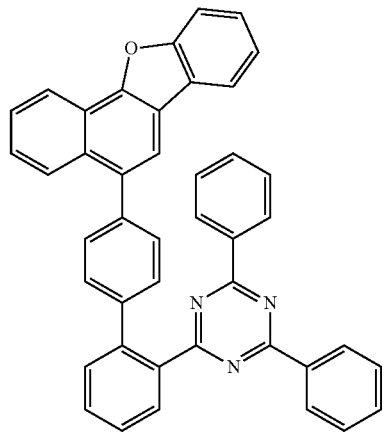
Compound 5-40
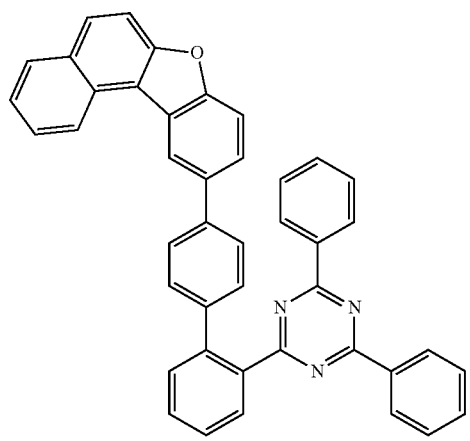
Compound 5-41
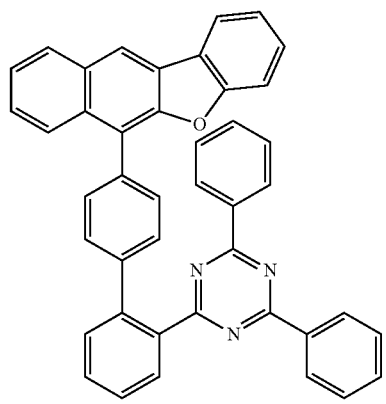

Compound 5-42
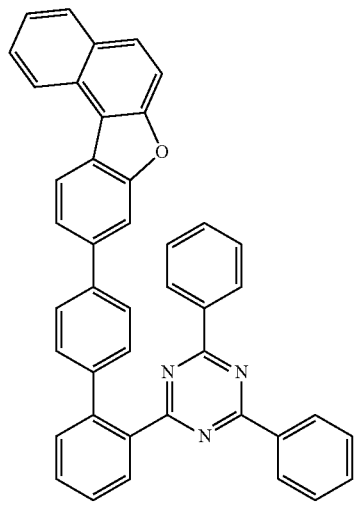
Compound 5-45
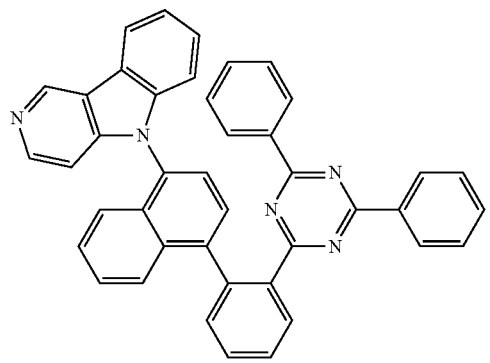
Compound 5-43
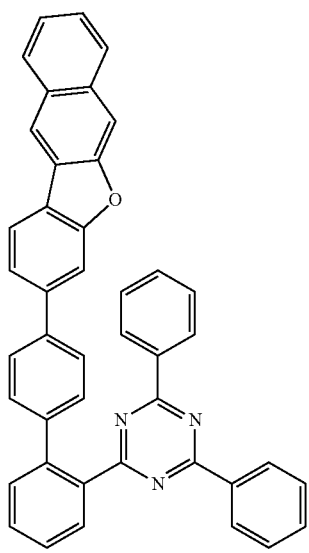
Compound 5-46
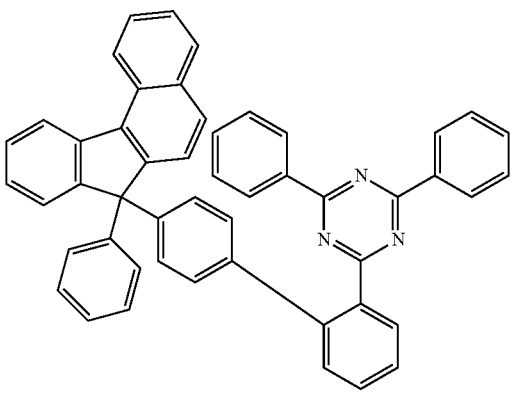
Compound 5-47
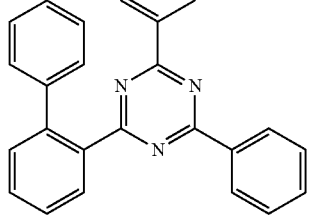
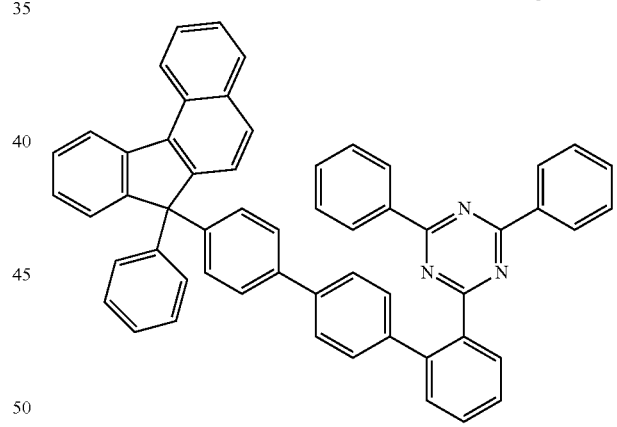
Compound 5-44
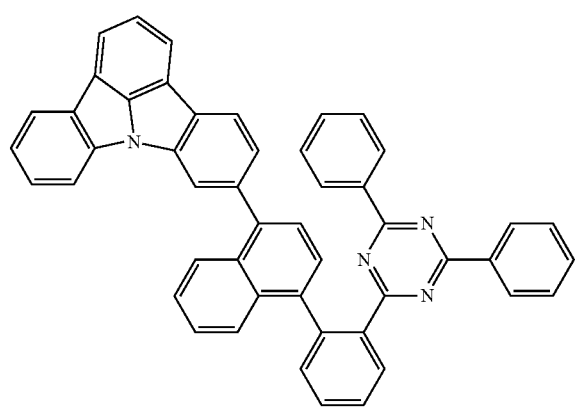
Compound 5-50
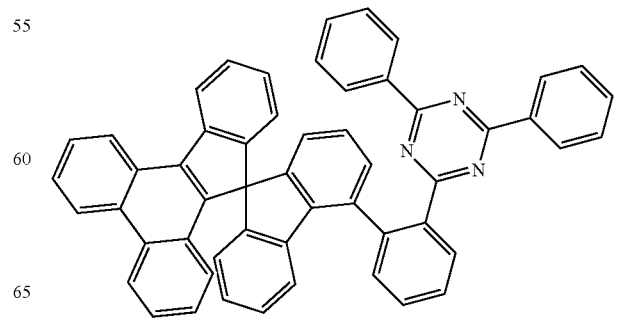

-continued

Compound 5-51

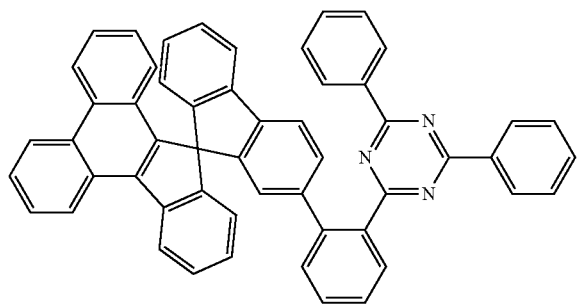

Compound 5-52

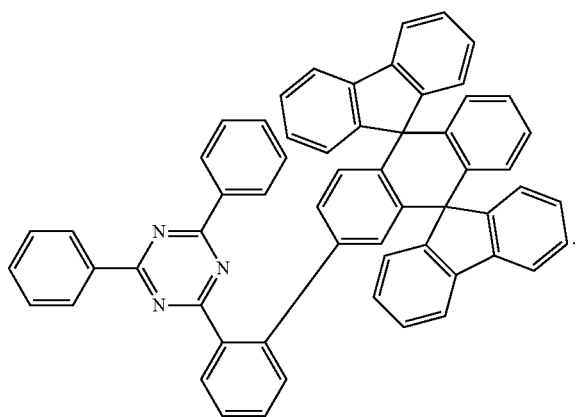

6. An organic light emitting device comprising:
 a first electrode;
 a second electrode provided to face the first electrode; and
 one or more organic material layers provided between the first electrode and the second electrode,
 wherein the one or more organic material layers comprise the compound of claim 1.

7. The organic light emitting device of claim 6, wherein the one or more organic material layers comprise an electron transport layer or an electron injection layer, and
 the electron transport layer or the electron injection layer comprises the compound.

8. The organic light emitting device of claim 6, wherein the one or more organic material layers comprise a light emitting layer, and
 the light emitting layer comprises the compound.

9. The organic light emitting device of claim 6, wherein the one or more organic material layers comprise a hole injection layer or a hole transport layer, and
 the hole injection layer or the hole transport layer comprises the compound.

10. The organic light emitting device of claim 6, wherein the one or more organic material layers comprise an electron transport layer, and the electron transport layer comprises the compound, and the one or more organic material layers further comprise one or two or more layers selected from a group consisting of a hole injection layer, a hole transport layer, a light emitting layer, an electron injection layer, an electron blocking layer, and a hole blocking layer.

* * * * *